(12) United States Patent
Frederick et al.

(10) Patent No.: US 7,596,427 B1
(45) Date of Patent: Sep. 29, 2009

(54) MEDICAL ITEM STORAGE CABINET AND METHOD

(75) Inventors: David T. Frederick, North Huntington, PA (US); James A. Michael, Cranberry Township, PA (US); R. Michael McGrady, Baden, PA (US)

(73) Assignee: AutoMed Technologies, Inc., Chesterbrook, PA (US)

( * ) Notice: Subject to any disclaimer, the term of this patent is extended or adjusted under 35 U.S.C. 154(b) by 511 days.

(21) Appl. No.: 11/031,351

(22) Filed: Jan. 7, 2005

Related U.S. Application Data

(60) Continuation-in-part of application No. 10/725,913, filed on Dec. 1, 2003, now Pat. No. 6,963,791, which is a division of application No. 09/848,633, filed on May 3, 2001, now Pat. No. 6,658,322.

(60) Provisional application No. 60/202,508, filed on May 5, 2000, provisional application No. 60/535,216, filed on Jan. 9, 2004.

(51) Int. Cl.
*G06F 17/00* (2006.01)
(52) U.S. Cl. ............... 700/243; 700/231; 700/232; 700/242; 312/209
(58) Field of Classification Search ......... 700/231–244; 220/264; 221/1–312 C; 312/209
See application file for complete search history.

(56) References Cited

U.S. PATENT DOCUMENTS

| | | | | |
|---|---|---|---|---|
| 3,827,569 A | * | 8/1974 | Canning | ........... 211/7 |
| 4,518,208 A | | 5/1985 | Marder | |
| 5,172,829 A | * | 12/1992 | Dellicker, Jr. | ........... 221/13 |
| 5,346,297 A | * | 9/1994 | Colson et al. | ........... 312/215 |
| 5,593,267 A | * | 1/1997 | McDonald et al. | ........... 414/273 |
| 5,745,366 A | | 4/1998 | Higham et al. | |
| 5,790,409 A | * | 8/1998 | Fedor et al. | ........... 700/232 |
| 5,805,455 A | | 9/1998 | Lipps | |
| 5,805,456 A | * | 9/1998 | Higham et al. | ........... 700/236 |
| 5,848,593 A | * | 12/1998 | McGrady et al. | ........... 128/897 |
| 5,905,653 A | | 5/1999 | Higham et al. | |
| 5,927,540 A | | 7/1999 | Godiewski | |
| 5,940,306 A | | 8/1999 | Gardner et al. | |
| 5,993,046 A | * | 11/1999 | McGrady et al. | ........... 700/231 |
| 6,011,999 A | | 1/2000 | Holmes | |
| 6,039,467 A | | 3/2000 | Holmes | |
| 6,109,774 A | | 8/2000 | Holmes et al. | |
| 6,116,461 A | | 9/2000 | Broadfield et al. | |

(Continued)

*Primary Examiner*—Gene Crawford
*Assistant Examiner*—Michael K Collins
(74) *Attorney, Agent, or Firm*—Ralph E. Jocke; Daniel D. Wasil; Walker & Jocke

(57) ABSTRACT

The system for controlling and tracking medical items (830) includes a plurality of medical item storage cabinets (878). Each cabinet includes a plurality of doors (888-894). The doors control access to shelves (902, 904) and support modules (1210). Shelves and support modules include user interfaces (938, 1214). Authorized users desiring to take medical items from storage locations in cabinets for use in treating patients are enabled to provide inputs through a display terminal (880) adjacent to cabinets and/or interfaces to indicate the taking of medical items. Storage cabinets include visual indicators so that users may be guided to find a selected medical item for which information is input at an associated display terminal. Alternatively, authorized users gain access to the interior of the cabinet and indicate through appropriate inputs through interfaces on the shelves the types and quantities of items being taken.

20 Claims, 40 Drawing Sheets

U.S. PATENT DOCUMENTS

| | | |
|---|---|---|
| 6,151,536 A | 11/2000 | Arnold et al. |
| 6,272,394 B1 | 8/2001 | Lipps |
| 6,283,565 B1 * | 9/2001 | Kohler et al. ............... 312/326 |
| 6,339,732 B1 | 1/2002 | Phoon et al. |
| 6,385,505 B1 | 5/2002 | Lipps |
| 6,401,991 B1 | 6/2002 | Eannone |
| 6,600,656 B1 * | 7/2003 | Mori et al. .................. 361/724 |
| 7,258,249 B1 * | 8/2007 | Frederick et al. ............ 221/282 |

* cited by examiner

| Restock | | | | |
|---|---|---|---|---|
| Position Description | Material Name | Unit of Issue | Item Code | Qty |

| Prev Page | Nursing Name | | Select | Help |
|---|---|---|---|---|
| NextPage | Supply Position | Below Min | Print | Close |

PATIENT USAGE BROWSER ⎯1084

| PAT_USAGE | | | | |
|---|---|---|---|---|
| Nursing Name | Size | Qty Form | Status | Date/Time UserName |
| Erthromyclyn | | 1 | Taken | 20 Aug 07:30 Frederick |

| Prev Page | Material Name | | Return | Help |
| Next Page | Sort by Supply | | Waste | Close |

User Count
- Supply Position
- Material Name
- Nursing Name

Actual Supply Position Quantity

| 1 | 2 | 3 |
| 4 | 5 | 6 |
| 7 | 8 | 9 |
| 0 | Clear |
| Accept | Help |
| Cancel Dispense | Close |

FIG. 29

| Stockit | | | | |
|---|---|---|---|---|
| Position Description | Trade Name | | Unit of Issue | Qty |

| Prev Page | Nursing Name | Keypad | Accept | Help |
|---|---|---|---|---|
| Next Page | Supply Position | Discrepancy | | Cancel |

1178 (top), 1182 (Accept)

| Patient Browser - [NO PATIENT SELECTED] | | | |
|---|---|---|---|
| Room | Bed | Sex | Patient Name | Patient ID |
| keithk-loc | 01 | M | YOUNG, WILLIAM | 000000209262 |

Administration
Find / Add
Patient Info
Patient Usage
Sort by Room
Display Visit ID Inventory Functions
Restock
Audit
StockIt Supply Functions
FindIt
Procedure
TakeIt Prev Page
Next Page
Edit
Help
Logout 1238
1240

FIG. 40

| Audit (KeithK Tower 1) - [KEITHK - SSP, in keithk-ssp] | | | | |
|---|---|---|---|---|
| Position Description | Material Name* | Unit of Issue | Last Audit | Qty |
| Keith K Tower 1 Shelf 3 Bin 1 -1 | 141 Suction Cath | Each | 07/16/2003 | 8 |
| KeithK Tower 1 Shelf 1 Bin 2 - 1 | 3x3 Sponges | Pack | | |
| KeithK Tower 1 Shelf 1 Bin 1 - 1 | Ace Bandage 6" | Each | | 0 |
| Keith Tower 1 Shelf 2 Bin 1 - 1 | Adult Non-rebreather Mask | Each | | |

1246

1248

Nursing Name
Supply Position

Audit All

PrevPage
NextPage

Cancel
Accept

FIG. 41

MEDICAL ITEM STORAGE CABINET AND METHOD

CROSS REFERENCE TO RELATED APPLICATION

This application claims benefit pursuant to 35 U.S.C. § 119(e) of Provisional Application Ser. No. 60/535,216 filed Jan. 9, 2004. This application is also a Continuation in Part application of U.S. application Ser. No. 10/725,913 filed Dec. 1, 2003, which is a Divisional application of Ser. No. 09/848,633 filed May 3, 2001, which claims benefit pursuant to 35 U.S.C. § 119(e) of Provisional Application Ser. No. 60/202,508 filed May 5, 2000. The disclosures of each of these prior applications is incorporated herein by reference as if fully rewritten herein.

TECHNICAL FIELD

This invention relates to devices, systems and methods for controlling and tracking medical items such as medical and surgical supplies. Particularly this invention relates to apparatus and methods for controlling and tracking medical items in hospitals, clinics or other health care settings.

BACKGROUND ART

The treatment of patients in hospitals, clinics and other health care settings usually involves receipt by the patient of medical items. These items may include prescription items such as drugs and medications. Medical treatment may also involve other nonprescription medical items such as medical and surgical supplies, as well as consumable medical equipment. To serve the needs of patients in a health care setting, sufficient stocks of such medical items must be kept available for use. Because such items may be relatively high in cost and/or relatively large quantities of such items may be consumed, it is important for the health care provider to accurately control and track the use of such items and to accurately allocate the charges associated with the use of such items to patients.

Systems and methods for tracking the use of medical items have been previously developed. Examples of such systems and methods are disclosed in U.S. Pat. Nos. 5,404,384; 5,533,079; 5,790,409; 5,848,593; 5,912,818; 5,993,046; 6,019,249; 6,073,834; 6,112,506; 6,141,942; and 6,163,737, the disclosures of all of which are incorporated by reference as if fully rewritten herein.

While the previously developed systems provide useful devices and methods for tracking the use of medical items, further improvements are possible. Specifically, persons who must obtain medical and surgical supply items from storage may wish to do so more quickly while still maintaining adequate security and tracking of the items. In addition, persons who are taking such medical items from storage may often know exactly where a particular desired item is located and may benefit by being able to access and take the item with a minimum of delay. In other cases, persons may be unfamiliar with the location of a particular desired item. In such situations a person may benefit by having a system which guides the user to a particular item that they have indicated that they wish to find. In other situations, persons may wish to take from adjacent storage locations a number of different types of medical items. In such cases the medical professional taking such items may wish to take the items during a single occasion when a lockable storage cabinet or other controlled storage location has been opened. In such cases it may be useful for the person to indicate to the system the types and quantities of each medical item they are taking as quickly as possible.

Thus there exists a need for improved methods and systems for controlling and tracking the taking of medical items.

DISCLOSURE OF INVENTION

It is an object of an exemplary form of the present invention to provide a system for controlling and tracking medical items.

It is a further object of an exemplary form of the present invention to provide a system for controlling and tracking medical items that can be used to track the use of medical and surgical supplies.

It is a further object of an exemplary form of the present invention to provide a system for controlling and tracking medical items that enables an authorized user to take items from storage and record such taking quickly.

It is a further object of an exemplary form of the present invention to provide a system for controlling and tracking medical items that enables a user to be guided to a storage location where a particular type medical item desired by the user is stored.

It is a further object of an exemplary form of the present invention to provide a system for controlling and tracking medical items that enables an authorized user to take and indicate the taking of a plurality of different types of medical items.

It is a further object of an exemplary form of the present invention to provide a method for controlling and tracking medical items which enables a user to indicate the taking of additional items or to change the indication of the types of items being taken after the user has gained access to a controlled access storage location.

It is a further object of an exemplary form of the present invention to provide a system for controlling and tracking medical items that includes a user interface that is readily used and operated by users taking medical items from controlled storage areas.

It is a further object of an exemplary form of the present invention to provide a system for controlling and tracking medical items that includes a storage cabinet with configurable shelves, which shelves include storage locations that may be correlated to input devices on a user interface.

It is a further object of an exemplary form of the present invention to provide a system for controlling and tracking medical items that includes a versatile storage cabinet structure.

It is a further object of an exemplary form of the present invention to provide a method for controlling and tracking the taking of medical items from controlled access storage areas within a storage cabinet.

It is a further object of an exemplary form of the present invention to provide a method for controlling and tracking the taking of medical items from a storage cabinet that enables users to indicate the types and quantities of medical items being taken proximate to the time of such taking.

It is a further object of an exemplary form of the present invention to provide a method for controlling and tracking the taking of medical items from a storage cabinet that includes the capabilities of guiding a user to a storage location for a requested type of medical item.

It is a further object of an exemplary form of the present invention to provide a method for controlling and tracking the taking of medical items from a storage cabinet that enables a user to indicate and change the types and quantities of medical items being taken once access to the cabinet has been gained.

It is a further object of an exemplary form of the present invention to provide a method for controlling and tracking the taking of medical items from a cabinet that provides fast and efficient tracking and removal of medical items.

Further objects of exemplary forms of the present invention will be made apparent in the following Best Modes For Carrying Out Invention and the appended claims.

The foregoing objects are accomplished in an exemplary form of the present invention through use of a method and system which includes a storage cabinet for holding medical items such as medical and surgical supplies. The storage cabinet includes a plurality of lockable doors which control access to the interior thereof.

The cabinet includes a plurality of shelves in supporting connection with the interior of the cabinet. In some embodiments of the invention the shelves may be stationary shelves, and in others, pullout type shelves, and in others a combination. The shelves include storage locations or areas for storing medical items.

Certain shelves in exemplary embodiments of the invention include a shelf interface located adjacent a front portion of a storage shelf. The shelf interface comprises a user interface that includes a plurality of push buttons. The shelf interface further includes a plurality of visual indicators, each such indicator being uniquely associated with one of the plurality of buttons.

The shelf interface of the exemplary embodiment further includes a numerical keypad for manually inputting numerical values. The shelf interface further includes a shelf display for providing a visual output including quantity values. The exemplary embodiment of the shelf interface further includes a clear indicator that may be used for clearing inputs previously made to the system through input devices.

In the exemplary embodiment storage locations are correlated with particular buttons on the shelf interface. This is done in an exemplary embodiment by applying indicia such as corresponding self-adhesive labels to a storage location and to the corresponding button which may be used to indicate to the system the removal or addition of medical items stored in the storage location.

The exemplary embodiment further includes a terminal that is accessible externally relative to the cabinet. The terminal may be a display terminal of the type described in connection with the incorporated patent disclosures. The terminal enables users to provide inputs to and receive outputs generated through operation of one or more processors operating in connection with the system. In the exemplary embodiment the terminal may be used by a user to input user identifying information. The terminal in the exemplary embodiment may also be used for providing inputs from a user including selections related to patients, medical items, quantities or other values pertinent to the tracking of the medical items stored in the cabinet.

In the exemplary embodiment, an authorized user is enabled to obtain medical items from the cabinet and to record the taking thereof in at least two ways. In accordance with a first approach, a user after being identified as authorized to use the system, indicates their desire to generally access medical items stored in the storage cabinet. In response to an indicative input to the terminal, doors on the cabinet which control access items to which the particular user is authorized to have access, are unlocked. In the exemplary embodiment a visual indication is given to indicate which doors are unlocked. The user may then open these doors and take the medical items from the storage locations. To record the taking of each medical item, the user in the exemplary embodiment touches the button on the shelf interface corresponding to the storage location on the shelf from which a medical item is being taken to identify the particular type of medical item to the system. The user also inputs the quantity of the type medical item being taken from the identified storage location through the numerical keypad on the corresponding shelf interface. When the user inputs such a value, the value is displayed on the shelf display.

If the user should make a mistake in indicating the type or number of medical item being taken, the user may clear the incorrect input by pressing the clear indicator. The user may then enter correct type and quantity data. The user may repeat this process for a plurality of medical items located in different storage locations. Once the user has provided inputs to indicate the taking of medical items from the cabinet, the taking of such items is recorded in a data store.

Alternatively in the exemplary embodiment, a user may input information corresponding to a particular type medical item (or a plurality of types) that the user wishes to find within the cabinet. In response to an authorized user providing such inputs, the cabinet door (or doors) controlling access to the shelf or shelves, in which the selected medical items are stored, will unlock. The unlocking of the doors in the exemplary embodiment is indicated through activation of visual indicators associated with the doors. While taking such medical items, the visual indicators corresponding to the storage location identifying buttons will be activated to indicate to the user where the selected medical item or items are located. In the exemplary embodiment color-coding is used as the visual indicia, which correlates the buttons and the storage locations. This enables the user to quickly find the requested medical items even though each storage location is generally not in proximity to its corresponding visual indicator.

In the exemplary embodiment when the user is requesting of the system to "find" medical items, the quantity of each particular item requested is displayed through the shelf display. In cases where multiple items from the same shelf have been selected, the user can verify the quantity of each item that they have previously selected through the display terminal by touching the particular button corresponding to the item. This causes the selected quantity to be output through the display. Further in the exemplary embodiment, in the event that the user determines once they have accessed a storage location that they wish to take different quantities or other types of medical items, they may do so through use of the clear indicator and the buttons and numerical keypad on the shelf interface. Such approaches enable a user to modify or add to the types and quantities of medical items being notified to the system as taken during the course of a single occasion when the particular storage shelf is accessed. Once the user has provided the corresponding inputs and taken all of the desired medical items, the taking of such items is recorded in a database.

In some alternative embodiments one or more processors may operate in the system so a user can be guided to "find" items in the manner previously described. However, in addition to the user being given access to the particular cabinet or shelf where the designated items are located, access is provided to all the items to which the user is authorized to have access. In this way the user is guided by the visual indicators to the medical item(s) that the user specifically wanted to find, but in addition, the user can take other medical items that the user knows the locations for, and the user can indicate the types and numbers of such items in the manner previously described. Of course this approach is exemplary of approaches that may be used.

In alternative embodiments cabinets may include storage locations for hanging articles such as catheters. Such items are suspended from supports on a module. In an exemplary embodiment the module includes an interface similar to the shelf interface. The interface enables users to locate items in a "find" mode and to indicate items taken in a "take" mode. In the exemplary embodiment the supports can be mounted in either a left or right hand configuration to facilitate ease of operation and the mounting of cabinet doors in either left hand or right hand configuration.

BRIEF DESCRIPTION OF DRAWINGS

FIGS. 23-31 are views of exemplary screen outputs presented on a display terminal in connection with the operation of the exemplary supply cabinet as represented in FIGS. 19-22.

FIG. 36 is an alternative screen output associated with the flow diagram shown in FIG. 35.

FIGS. 38-41 are views of exemplary screen outputs presented on a display terminal in connection with the exemplary audit function corresponding to the flow chart in FIG. 37.

BEST MODES FOR CARRYING OUT INVENTION

Figure 1:
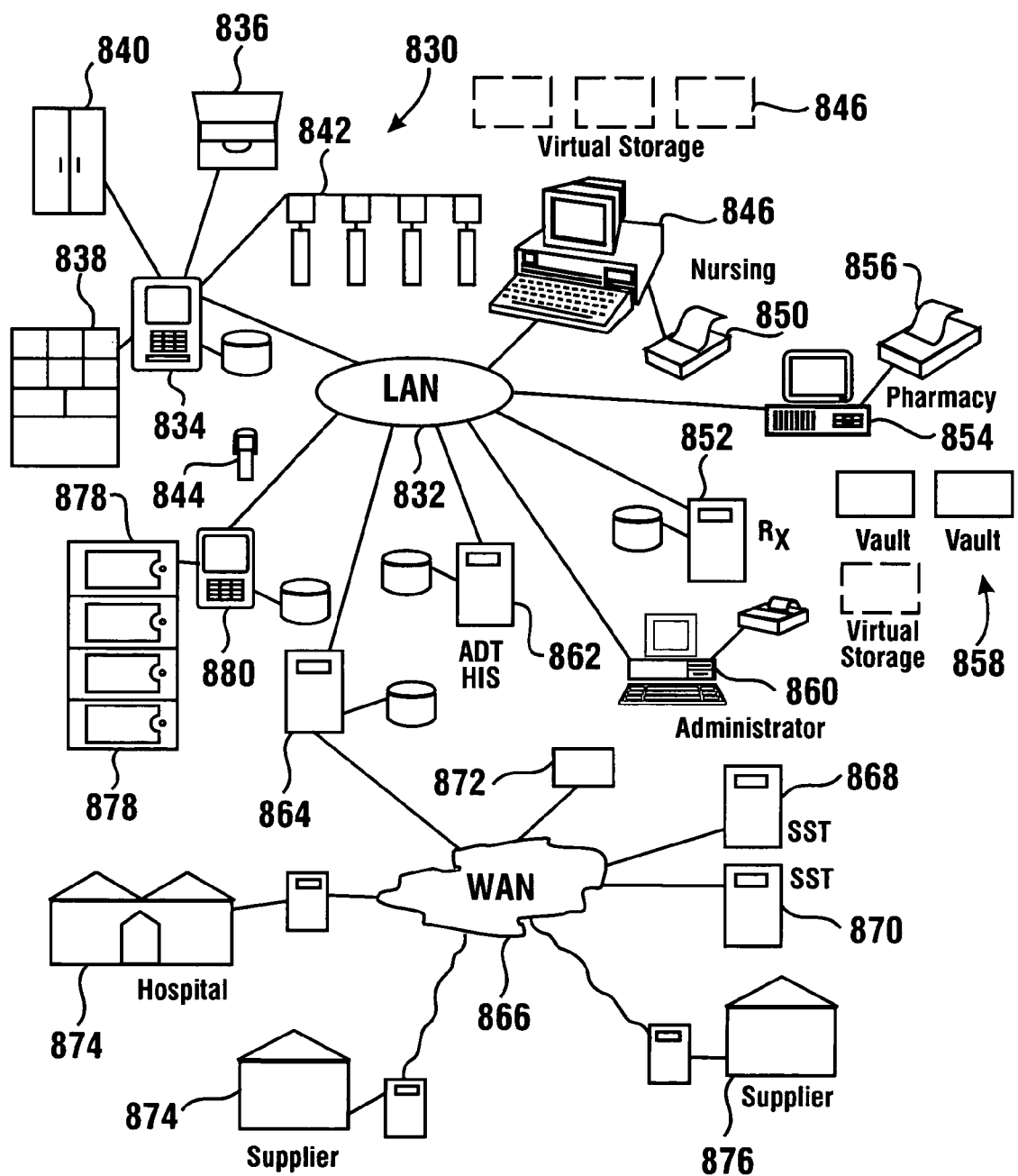
FIG. 1 is a schematic view of an exemplary form of a system of the present invention that includes features for tracking and controlling the taking of medical items from a supply cabinet.

Referring now to the drawings and particularly to FIG. 1, there is shown a system generally indicated 830 including an exemplary embodiment of the present invention. System 830 is generally similar to system 322 shown in FIG. 40 of U.S. Pat. Nos. 6,112,501 and 5,912,818, the disclosures of which patents are incorporated herein. Components and features discussed in each of these previously described systems may be used in connection with system 830. It should be understood that in some embodiments these components may be included and may operate in system 830 in a manner similar to that described in the incorporated disclosures. Various combinations of components and features described in such incorporated disclosures may be used in connection with system 830 even though not schematically represented in FIG. 1.

System 830 includes a local area network 832 that provides for electronic communication between components of the system. It should be understood that local area network 832 may be one or more interconnected systems which enable devices to communicate. Local area network 832 may extend within a single facility such as a single hospital or a clinic. Alternatively, local area network 832 may be a private network that extends between a group of facilities in which various components of the system are positioned.

In connection with local area network 832 are a plurality of display terminals schematically represented by a display terminal 834. Display terminal 834 in exemplary embodiments may be similar to display terminals 76, 98, 102, 338 described in the incorporated patent disclosures. Display terminal 834 has in connection therewith one or more computer memories which are alternatively referred to as data stores schematically shown, which hold information and/or programs. Display terminal 834 is operatively connected to devices for controlling access to medical items. These devices are schematically represented as a medication dispenser 836, an electronic lock drawer 838, an electronic lock cabinet 840 and hook registers 842. Of course, various types of other devices, which include storage locations for medical items, may be used in connection in embodiments of the system. Reading devices such as reading device 844 which may be similar to reading device 348 of the incorporated patent disclosure and/ or other reading devices may also be used in connection with the system. Such devices may include for example devices which can read radio frequency radiation such as RF backscatter devices or RFID tags.

Local area network 832 is also in connection with other computers such as nursing station computer 846. Nursing station computer 846 is representative of the computers that may be placed at nursing stations in a hospital or similar facility. Such computers may be used to provide inputs to the system concerning activities involving the treatment of patients. Nursing computer 846 may be used to also receive information such as information relating to medications and treatments which have been prescribed for various patients within the institution. Nursing station computer 846 may in some embodiments be used as an alternative to display terminal 834, and may also be used for tracking medical items in situations where automated types of storage and dispensing devices are not available. Nursing station computer 846 may be used to provide information concerning items taken or replaced in storage areas adjacent to the nursing station. The system may record the status of storage locations which users can access adjacent to the nursing station computer. The system may keep track of medical items stored in such storage locations in a manner similar to that used to track medical items which are removed from or added to other storage locations in the system. The tracking of medical items in such storage locations are represented in FIG. 1 as virtual storage areas 848. Nursing station computer 846 may also have in connection therewith an output device such as a printer 850 for purposes of printing reports related to activities occurring or scheduled to occur.

Local area network 832 in the exemplary embodiment is also in connection with one or more additional computers. Such computers which are sometimes referred to herein as processors may include, for example, computer 852. Computer 852 in the exemplary embodiment is operative to input, store and process information concerning medical items in storage locations, patients and medications prescribed for such patients, authorized users of the system, the taking and giving of medications for patients, as well as other information of the types discussed in the incorporated patent disclosures. In addition in the exemplary embodiment computer 852 is operative to store information concerning activities in the pharmacy. One or more pharmacy terminals 854 is in connection with the local area network 832 for purposes of communicating information with appropriately connected computers. Pharmacy terminal 854 includes output devices such as a printer 856. Printer 856 may be used for printing reports. Storage enclosures or facilities such as vaults 858 are also schematically indicated in the pharmacy. The storage vaults may include access controlled storage areas. Such storage vaults may be manually controlled by the system or electronically controlled to limit access to authorized persons.

Exemplary system 830 further includes administrative terminals schematically represented by an administrative terminal 860. Administrative terminal 860 in the exemplary embodiment may be used for programming the system, setting up storage locations, inputting data corresponding to authorized users of the system, inputting data concerning the medical items users are allowed to access, enabling users to selectively operate aspects of the system, monitoring activities and for engaging in other types of activities such as those discussed in the incorporated patent disclosures.

Network 832 is also in operative connection with one or more other computers schematically represented 862. Computer 862 may be used in the exemplary embodiment to process other information such as information in the facility's hospital information system (HIS) or in a facility's admission discharge and transfer (ADT) system. Data may be input through input devices connected to processors in these systems, data corresponding to patients who may be subject to treatment in the facility. Of course in other embodiments many other types of systems may be in connection with network 832.

System 830 further includes one or more computers schematically indicated 864 which serve as a gateway to other systems. In the exemplary embodiment, computer 864 serves as a firewall for limiting access to and from network 832. As schematically indicated in FIG. 1, computer 864 enables access to a wide area network 866 such as the Internet.

Wide area network 866 is schematically shown connected to a variety of other types of exemplary computers and systems. For example, network 866 may be operatively connected to self service medication dispensers 868, 870. Wide area network 866 may also be in connection with other computers such as a financial transaction processing computer 872. Financial transaction processing computers may be operative to settle accounts between various entities connected to the system such as a hospital and its employees and/or suppliers. Alternatively, financial transaction computers may be used for the hospital to receive or make payments from third parties such as insurers or other hospitals such as hospital 874 schematically indicated in FIG. 1. Suppliers who are in communication with network 866 are schematically represented 874 and 876. It should be understood that many additional types of providers of goods or services may be connected through one or more networks to the system 832.

In exemplary system 830 shown in FIG. 1, medical items may be obtained from a supply cabinet schematically indicated 878. Cabinet 878 is in operative connection with a display terminal 880. The display terminal includes one or more processors. Cabinet 878 is used to control access to a plurality of different types of medical items held therein. Items stored in the cabinet are enabled to be accessed by authorized users of the system in response to inputs to the system and/or the display terminal in a manner similar to that previously discussed. It should be understood that a plurality of cabinets 878 may be used in connection with a single display terminal or other adjacent computer.

Figure 2:
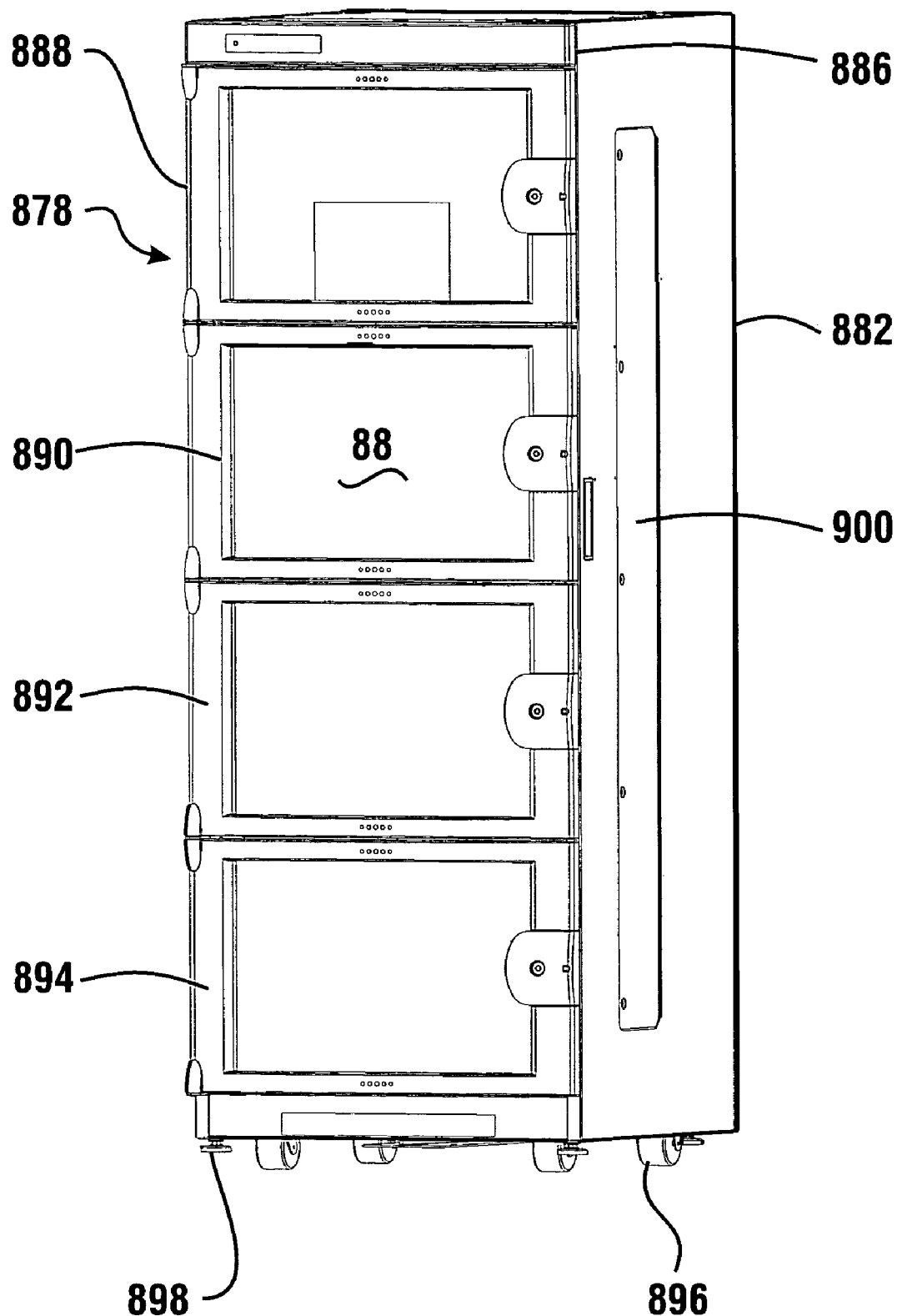
FIG. 2 is an isometric view of an exemplary embodiment of a supply cabinet.

The structure of an exemplary form of the medical item holding cabinet 868 is now described in detail with reference to FIGS. 2-17. As shown in FIG. 2, cabinet 878 includes a generally rectangular housing 882. Housing 882 includes a pair of side walls, top and bottom walls and a back wall which defines an interior area 884. Interior area 884 is accessible through a front opening 886 (see FIG. 3). Opening 886 is divided into regions or areas, each of which may be selectively accessed through corresponding lockable doors 888, 890, 892 and 894. The exemplary embodiment of cabinet 878 includes casters 896 to facilitate occasional but infrequent movement of a cabinet. Cabinet 878 further includes levelers 898. Levelers 898 can be selectively adjusted to engage a surface such as a floor on which the cabinet is supported and to hold the cabinet in a stationary position supported on the levelers instead of or in addition to the casters. Exemplary cabinet 878 further includes a light access door 900. Light access door 900, as later explained, may be used for accessing lighting elements which illuminate the interior area 884 of the cabinet.

Figure 3:
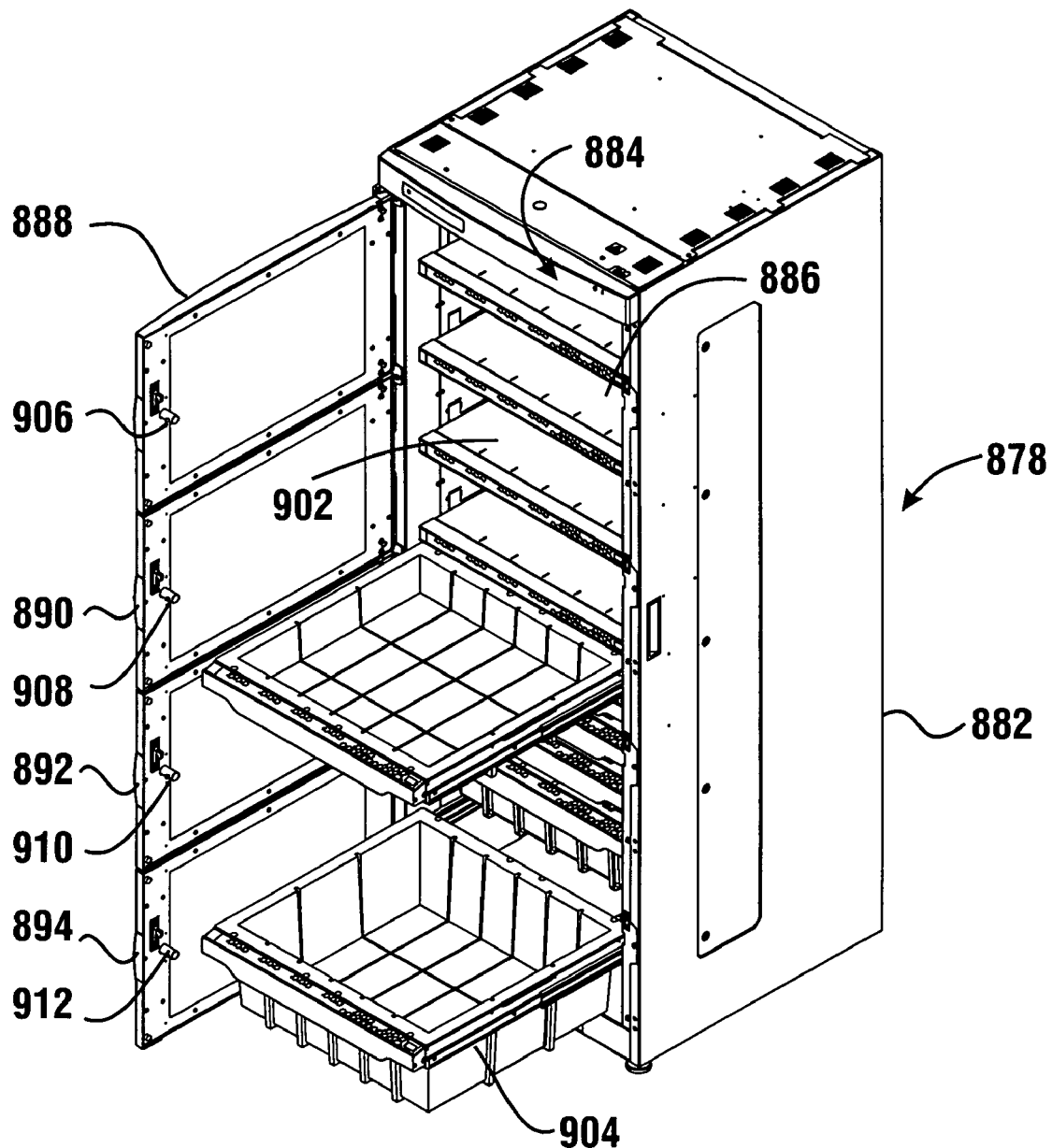
FIG. 3 is an isometric view of the supply cabinet shown in FIG. 2 with the doors open and the pullout shelves extended.

As shown in FIG. 3 in the exemplary embodiment of the cabinet 878, a plurality of shelves are housed in the interior area 884. The shelves may include stationary shelves such as shelf 902 as well as pullout shelves as represented by shelf 904. As used herein, a shelf includes structures adapted to support medical items within the cabinet. Each of the stationary shelves and pullout shelves is positioned in the interior area 884 behind a selected one of the doors 888, 890, 892 or

894. In this way, opening selected ones of the doors enables accessing certain shelves in the interior area, and the medical items stored in storage locations on such shelves.

Each of the doors 888, 890, 892 and 894 in the exemplary embodiment includes both a mechanical lock and an electronic lock. Each door includes a bolt 906, 908, 910 and 912. Each of the bolts operatively engages a strike mechanism later described in detail. The cooperating bolt and strike mechanisms enable selectively holding each door in either a locked or unlocked condition. The display terminal 880 in operative connection with the cabinet 878 enables selectively locking and unlocking the doors electronically so as to control access to medical items which are accessible on shelves positioned behind each respective door.

Figure 4:
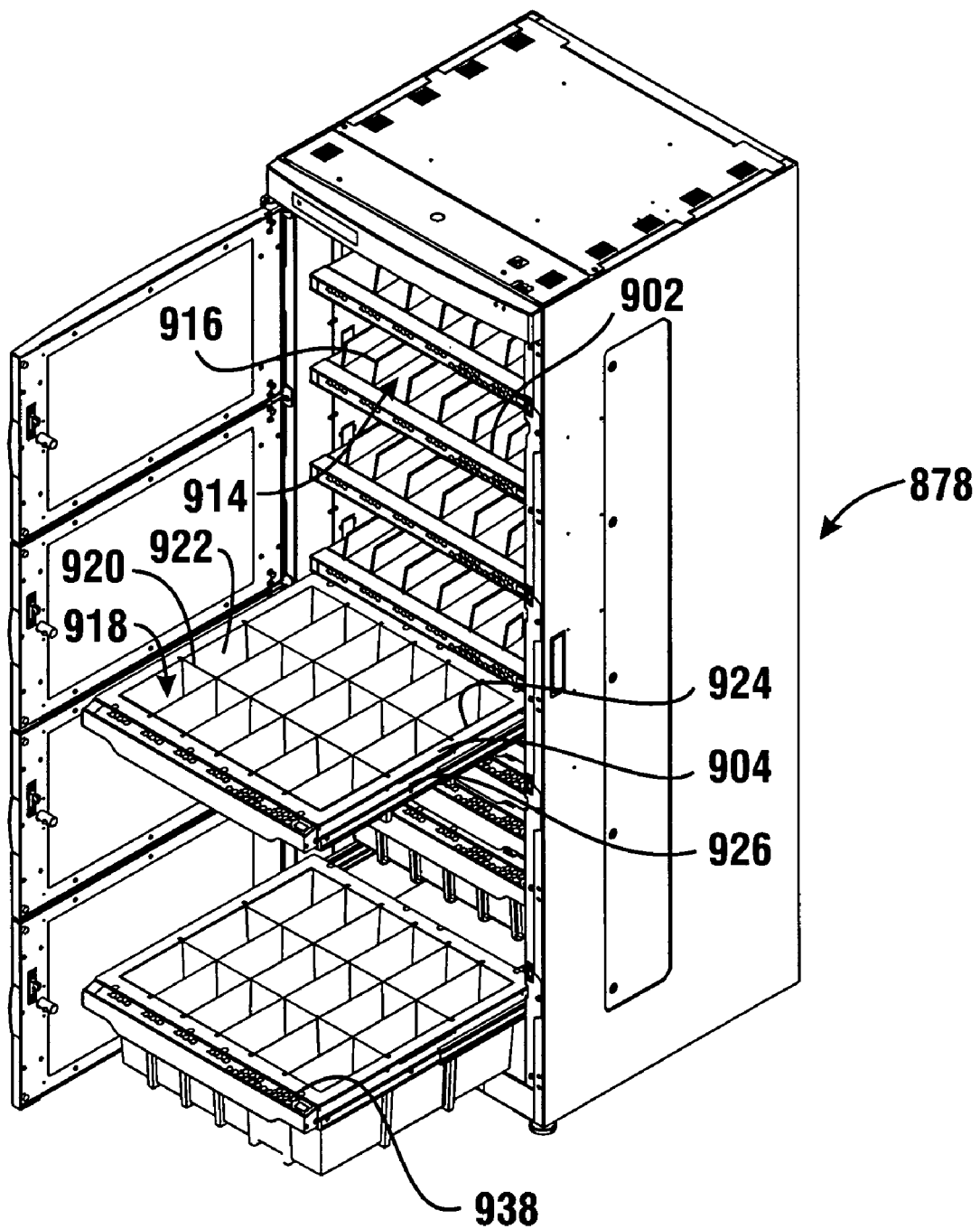
FIG. 4 is a view similar to FIG. 3 showing the shelves and dividers installed in the supply cabinet.

As shown in greater detail in FIG. 4, cabinet 878 has a plurality of storage locations therein. In the exemplary form of the invention, stationary shelves such as shelf 902 include a plurality of transversely spaced storage locations 914. Storage locations 914 are suitable for holding one or more medical items which can be suitably positioned within the elongated storage location. As can be appreciated, a plurality of medical items may be stacked in abutting relation within each storage location. The storage locations 914 are delineated by dividers 916. Dividers 916 may be transversely positioned in varied locations on the shelf so as to accommodate different sized medical items.

In some alternative embodiments additional dividers (not separately shown) may extend perpendicularly between dividers 916. Such perpendicularly extending dividers may be used to form multiple segregated storage locations between an adjacent pair of dividers 916. Further in other alternative embodiments movable holding devices such as a movable liner may be positioned between an adjacent pair of dividers. Such a liner may include one or more internal walls which bound one or more storage positions within the liner. Examples of such storage liners that may be movably positioned between adjacent dividers on shelf 902 are shown and described in U.S. Pat. No. 6,112,502 which is incorporated by reference as if fully rewritten herein. Such movable liners may be positioned in supporting connection with a shelf such as shelf 902, and pulled outward or removed by a user for purposes of observing the storage areas and medical items held therein.

Pullout shelves such as pullout shelf 904 may also include storage locations schematically indicated 918. Storage locations 918 are defined by dividers 920. Dividers 920 extend in a housing 922. Housing 922 is supported in a frame 924. The frame 924 is extendable from the interior area on slides 926.

Figure 6:
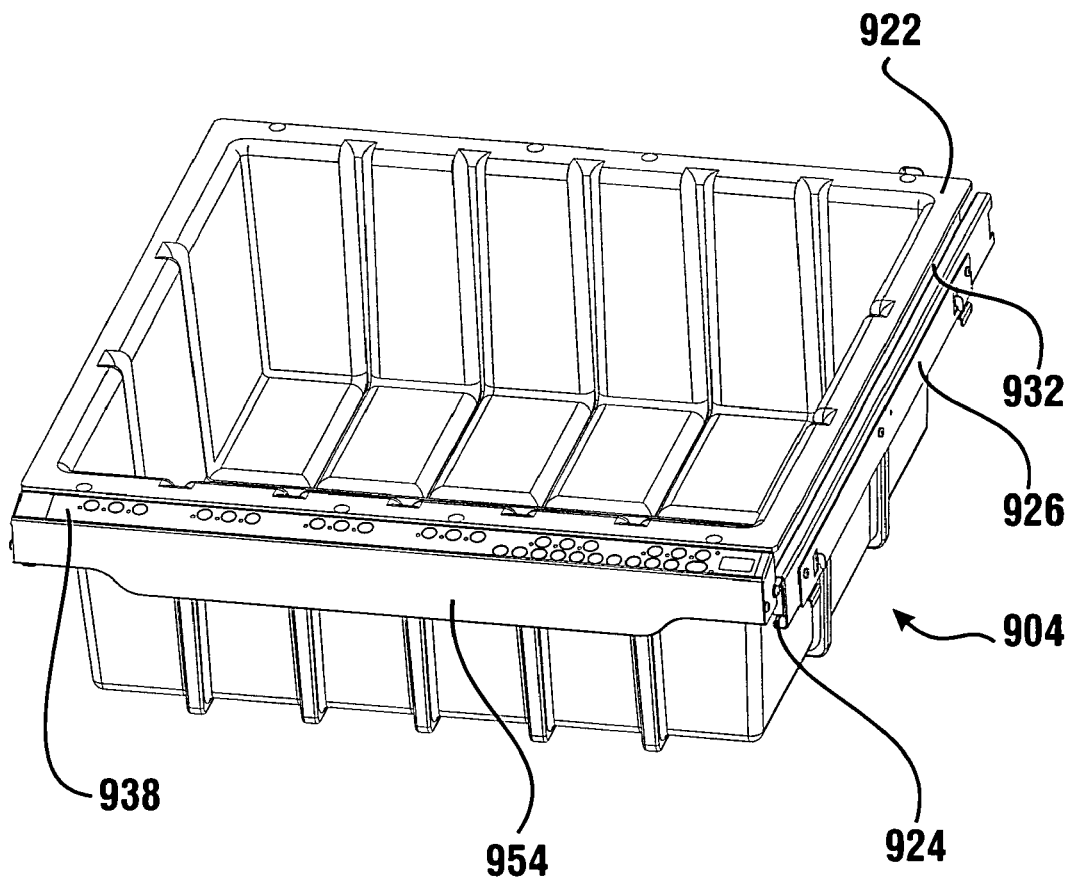
FIG. 6 is an isometric view of an exemplary pullout shelf.
Figure 7:
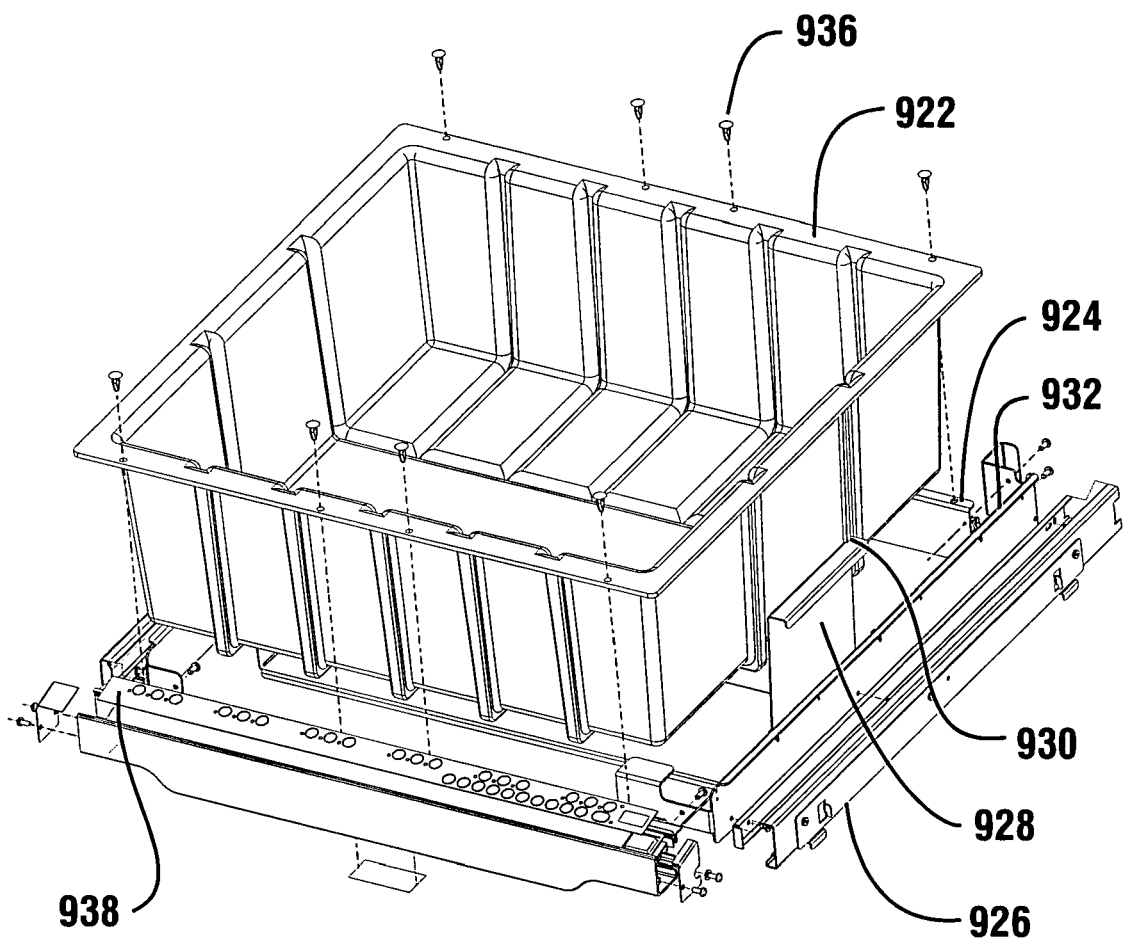
FIG. 7 is an exploded view of the pullout shelf shown in FIG. 6.
Figure 8:
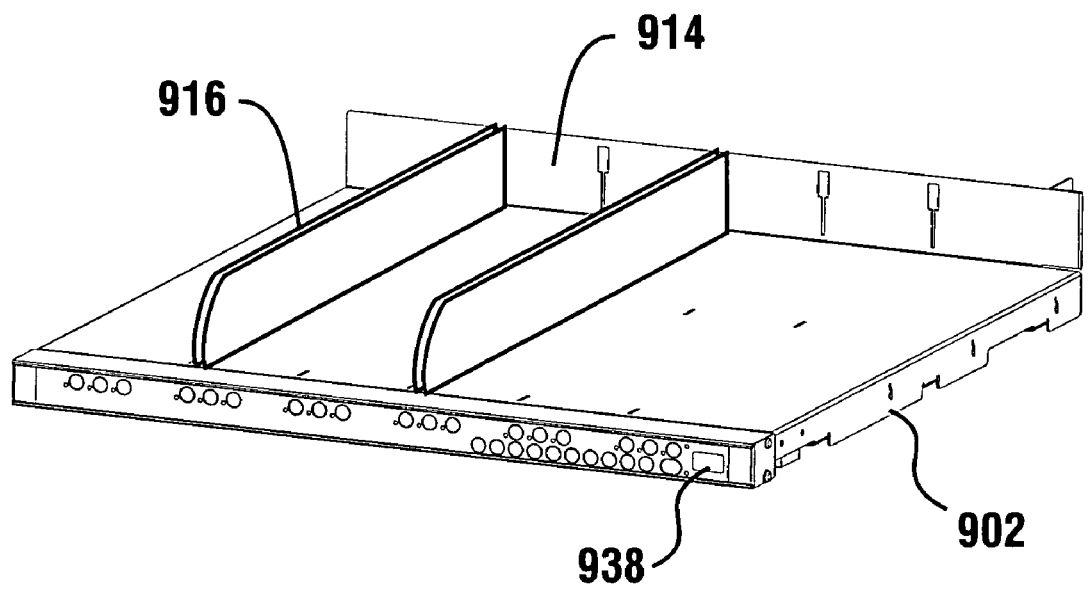
FIG. 8 is an isometric view of a stationary shelf.

As best shown in FIGS. 6 and 7, housing 922 in the exemplary embodiment includes a drop in liner which is supported on the frame 924. The frame includes a support bracket 928 which extends transversely under the housing 922 to provide additional support. The support bracket 928 includes angled engaging portions 930 which extend outward and engage the side members 932 of the frame. It should be understood that for some housings 922 which are not intended to support substantial weight, the support bracket 928 may not need to be used. In such situations, the support bracket need not be installed and the housing is supported by its edges on the frame. As can be appreciated, the construction of the exemplary embodiment facilitates the use of either housings which are intended to hold considerable mass such as the deep housing shown in FIG. 7 or, alternatively, relatively shallow housings for holding lower mass supported in the same type of basic pullout drawer structure. Shelves may have various arrangements of dividers therein. Further as represented by fasteners 936 in FIG. 7, housings 922 may be releasably fastened to the supporting frame 924. Alternatively housings may be supported in the frame without being fastened thereto.

In the exemplary embodiment of the cabinet 878, each of the stationary shelves and rollout shelves include a shelf interface 938. Shelf interface 938 is shown in greater detail in FIG. 5. Shelf interface 938 in the exemplary embodiment includes a user interface with a plurality of finger actuatable push buttons 940. Each push button 940 has a visual indicator 942 associated therewith. In the embodiment shown, the indicators include an LED which illuminates when activated in appropriate circumstances later described, to identify a particular button which button can be correlated with a storage location. In the exemplary embodiment, each shelf interface includes 18 buttons 940 each having an associated indicator 942. Of course, in other embodiments, other numbers and/or types of actuators other than buttons, or indicators other than illumination type indicators may be used.

Exemplary shelf interface 938 further includes a keypad 944. Keypad 944 includes numerals zero (0) through nine (9) which can be manually actuated by a user for purposes which are later discussed. The shelf interface 938 also includes a "clear" button 946. The clear button is used to clear or delete from the system an incorrect input. A display 948 is also included on the exemplary shelf interface. In the embodiment shown, display 948 is a two (2) character display such that it may output a two-digit value. Shelf interface 938 also includes a "take" indicator 950 and a "return" indicator 952 positioned adjacent to the display. In the exemplary embodiment, the take and return indicators comprise illuminated indicators such as LEDs. Of course in other embodiments different and/or other numbers and types of indicators may be used. It should be understood that in other embodiments the display 948 or indicators 950, 952 or both may be located elsewhere on the cabinet rather than the shelf.

As shown in FIG. 4, each of the stationary and pullout shelves includes a shelf interface. As shown in the exemplary stationary shelf 902 in FIG. 8, the shelf interface 938 extends generally vertically on a front portion of the shelf frame. This enables a user viewing a stationary shelf to observe the shelf interface as well as medical items located in storage locations 914 which extend between the dividers. As shown in FIG. 4, in the exemplary embodiment, stationary shelves 902 are generally positioned in the upper area of the cabinet 878 so that the stationary shelves are closer to eye level which facilitates a user's ability to observe the shelf interface 938 and the storage locations.

As best shown in FIG. 6 on the pullout shelves such as shelf 904, the shelf interface 938 is positioned adjacent the front portion of the shelf frame 924 and extends at an angle such that the interface is facing both forward and upward relative to the shelf. The shelf interface 938 in the exemplary embodiment is supported on a handle portion 954 adjacent the front of the frame. As shown in FIG. 4, pullout shelves may be positioned in areas of the cabinet 878 so that a user can see the shelf interface generally without having to stoop or bend down. This enables the user to see the indicators and actuate buttons on the shelf interface of the pullout shelves so as to provide inputs to the system. Further the position of the shelf interface on the pullout shelf enables a user to view the indicators and have access to the input devices even though the shelf is fully retracted into the interior area of the cabinet.

In the exemplary embodiment, the shelf interface 938 comprises a flexible circuit which has the buttons and indicators integrated therein. The flexible circuit is enabled to be positioned in an elongated slot that is integral with the front portions of both the stationary shelves or pullout shelves. This facilitates the construction of the shelves as well as replacement of any shelf interface units which may sustain a malfunction. Alternative embodiments may have alternative positions for supporting the shelf interface or may provide a movably positionable surface for the shelf interface so that the interface position may be selectively tailored to the position of the shelf in the cabinet. This may be done for example by supporting the shelf interface on a surface that is selectively angularly movable.

While the exemplary embodiment of the cabinet 878 has been shown with both stationary shelves and pullout shelves, it should be understood that embodiments of the invention may include only one shelf type. Further, while the exemplary form of the cabinet 878 has been shown with shelves, each of which has a shelf interface, it should be understood that in some embodiments, shelves may be included which do not have a shelf interface. Embodiments of the invention may have shelves of either type in which a shelf has no shelf interface. This may include for example where multiple shelves contain the same type of medical item and a single shelf interface is used to provide inputs related to medical items stored on multiple shelves. It should be further understood that alternative embodiments of the invention may include within the interior of the cabinet, fixed dividing walls. Such fixed dividing walls may be used to reduce the risk that a person who is authorized to receive access to one area of the cabinet may improperly access medical items located in another part of the cabinet to which that user is not authorized to have access such as by using a tool, probe or other device.

Figure 32:
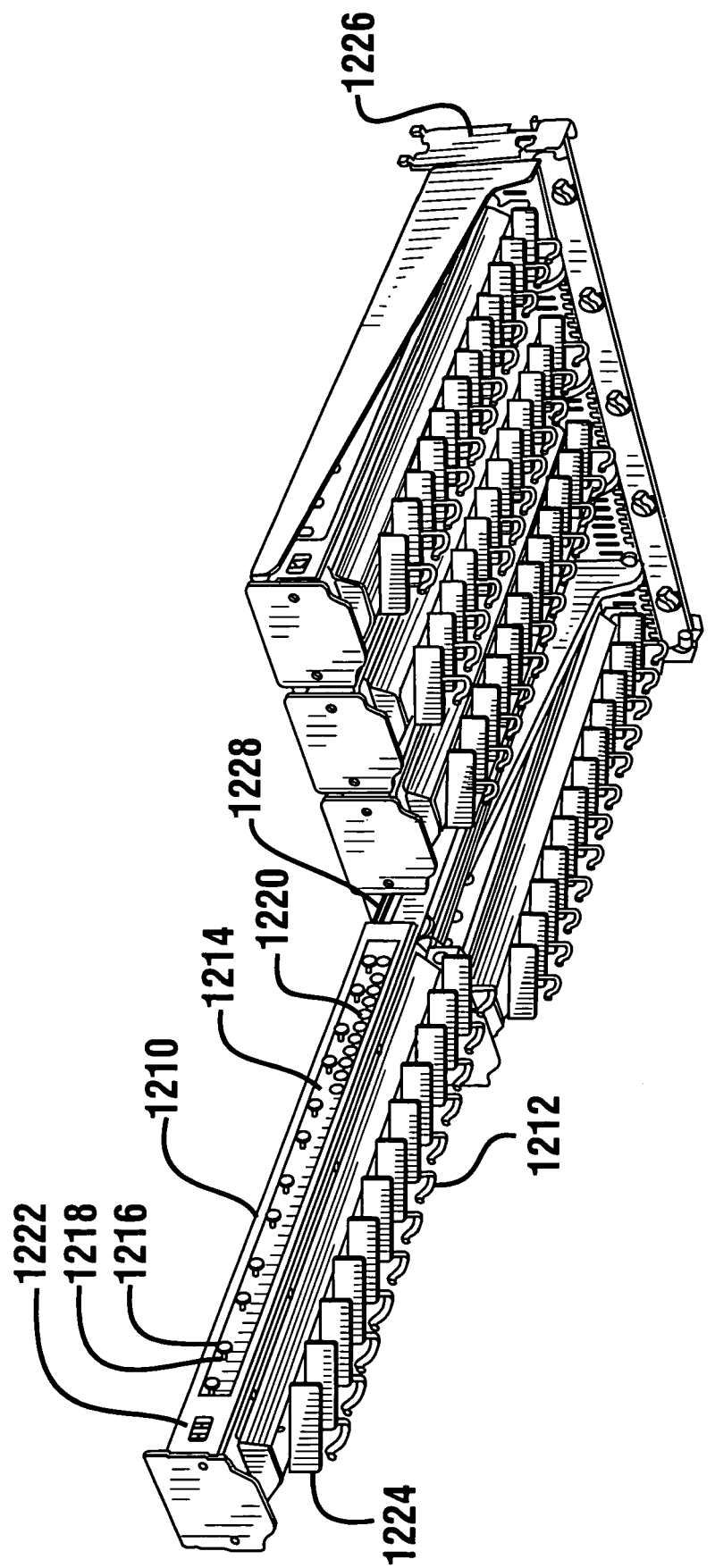
FIG. 32 is an isometric view of an exemplary storage module that may be used for holding hanging items such as catheters within a cabinet of an exemplary embodiment.

FIG. 32 shows an alternative medical item holding device that may be used in cabinets of some embodiments. Support modules 1210 include a plurality of supports 1212 extending from the underside thereof. The exemplary form of supports 1212 comprise hooks adapted for supporting medical items or supplies that are supported from the top. Such items may include, for example, catheters or other types of items that can be supported in their packaging by extending a support through an aperture in the upper portion thereof. It should be understood, however, that the hook like supports are exemplary and in other embodiments other types of supports may be used.

The exemplary support modules include a module interface 1214. Module interface 1214 is generally similar to shelf interface 938. Module interface 1214 includes a plurality of push buttons 1216, each having adjacent indicators 1218. Module interface 1214 further includes a keypad 1220 and a display 1222. In the exemplary embodiment, the module interface may include a plurality of buttons 1216, not all of which correspond to storage locations for medical items. In such embodiments, buttons that are actively associated with a storage location may be labeled with a self-adhesive label or similar item having an external color or design suitable for indicating that the particular push button is active. In the exemplary embodiment, supports 1212 each have an associated identifying label member 1224 mounted thereon. Label member 1224 may be used in some embodiments to support indicia which identifies the item type that is stored on the respective support. This may include, for example, a written description of a particular medical item type. Alternatively and/or in addition, label members 1224 may include machine readable indicia such as bar code RFID tags or other indicia.

In the exemplary embodiment, support modules 1210 are supported in the cabinet through a suitable support 1226 which attaches to the opening in the cabinet wall. Each of the modules is supported on a pullout slide 1228. Slide 1228 enables module 1210 to be moved outward when the cabinet door is open so as to enable a user to access the medical items stored on the supports as well as the buttons and indicators on the module interface 1214. In the exemplary embodiment, a plurality of support modules 1210 may be positioned side by side within the cabinet, and each of the modules preferably independently moveable so as to enable users to access items stored thereon.

In exemplary embodiments, the support modules may be configured so as to be positioned selectively so that the module interface 1214 is positioned either facing to the left or to the right. This facilitates viewing from a left front or a right position, as desired. This selective mounting enables the module interface to be directed conveniently for users based on the orientation of the cabinet. For example, in cases where the hinges which mount the cabinet doors are positioned so as to be hinged on the left hand side, it may be most convenient for the module interface to face to the right. Likewise, if the cabinet is configured so that the doors open with the hinges positioned on the right, it may be more convenient to have the module interface on the left side of the module. Of course this may vary depending on the configuration. The removable mounting of the module on a slide in the exemplary embodiment enables the interface to be positioned facing in either direction, in response to the side of the cabinet on which the hinges for the associated door are selectively mounted.

Figure 33:
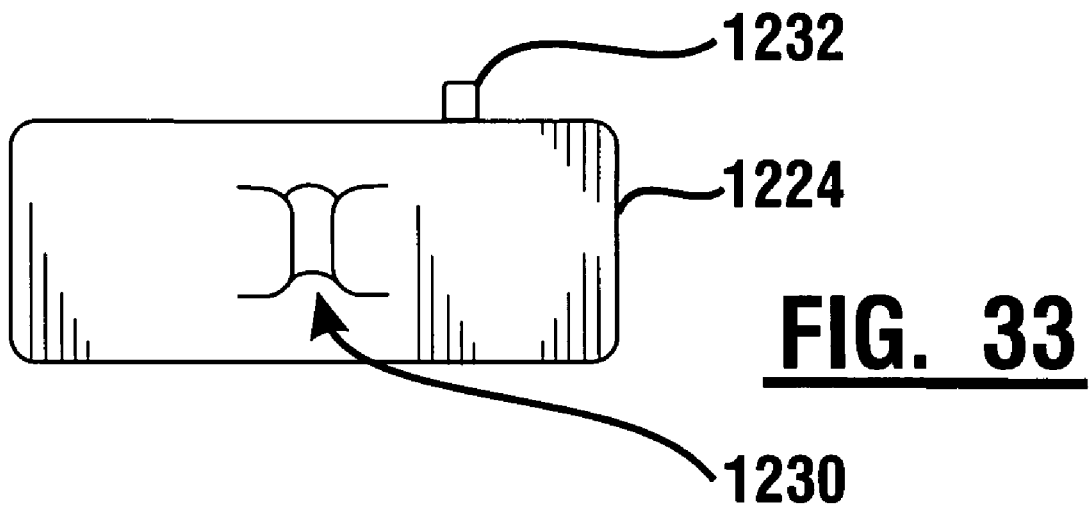
FIG. 33 is a rear view of an exemplary form of a label for identifying hanging items stored in the module shown in FIG. 32.

As shown in FIG. 32, the label members 1224 associated with the supports may be positioned so as to be more readily seen by a user who is positioned to view the module interface. For example, as shown in FIG. 32, with the module interface facing to the right, the label members 1224 are angled to the right. Similarly when the module interface is facing toward the left, it may be preferable to have the labels angled toward the left as viewed from outside the storage area in the cabinet. In an exemplary embodiment this is accomplished through labels configured as shown in FIG. 33. In the exemplary embodiment, the rear of label member 1224 includes a snap-in aperture 1230 which is adapted to accept the vertically extending portion of the exemplary supports 1212. Label member 1224 further includes a positioning projection 1232 extending from the upper end thereof.

Figure 34:
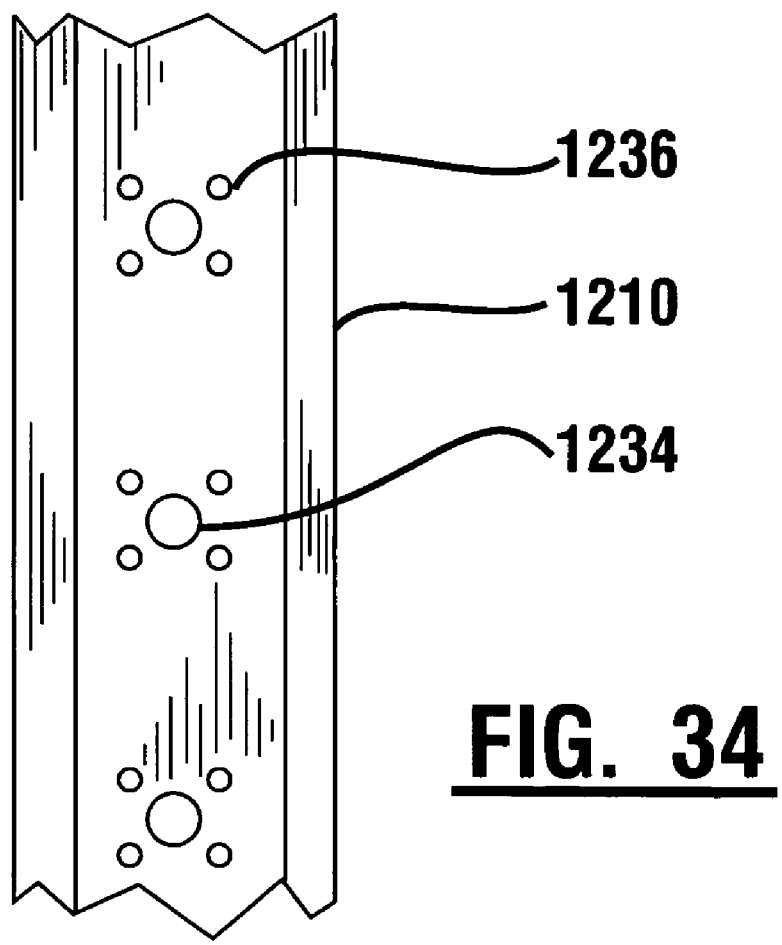
FIG. 34 is a bottom view of the module shown in FIG. 32, including apertures for accepting supports and projections on item labels.

The bottom of the support module 1210 is shown without the supports 1212 in FIG. 34. Apertures 1234 are adapted to accept the supports therein. As can be appreciated, in some exemplary embodiments it may be useful to be able to rotate the supports so that the support faces forward or rearward, depending on the orientation of the module. This may be accomplished by providing for the selectively rotatable positioning of the supports within the apertures 1234. Further, in the exemplary embodiment a plurality of projection accepting apertures 1236 are positioned adjacent to each of apertures 1234. Apertures 1236 are sized to accept projections 1232 therein. Apertures 1236 are positioned so that label members 1224 may be positioned and held in desired angular positions which facilitate the viewing thereof based on the orientation of the module interface and/or the supports 1212. Of course it should be understood that this approach is exemplary and in other embodiments other approaches may be used.

Figure 9:
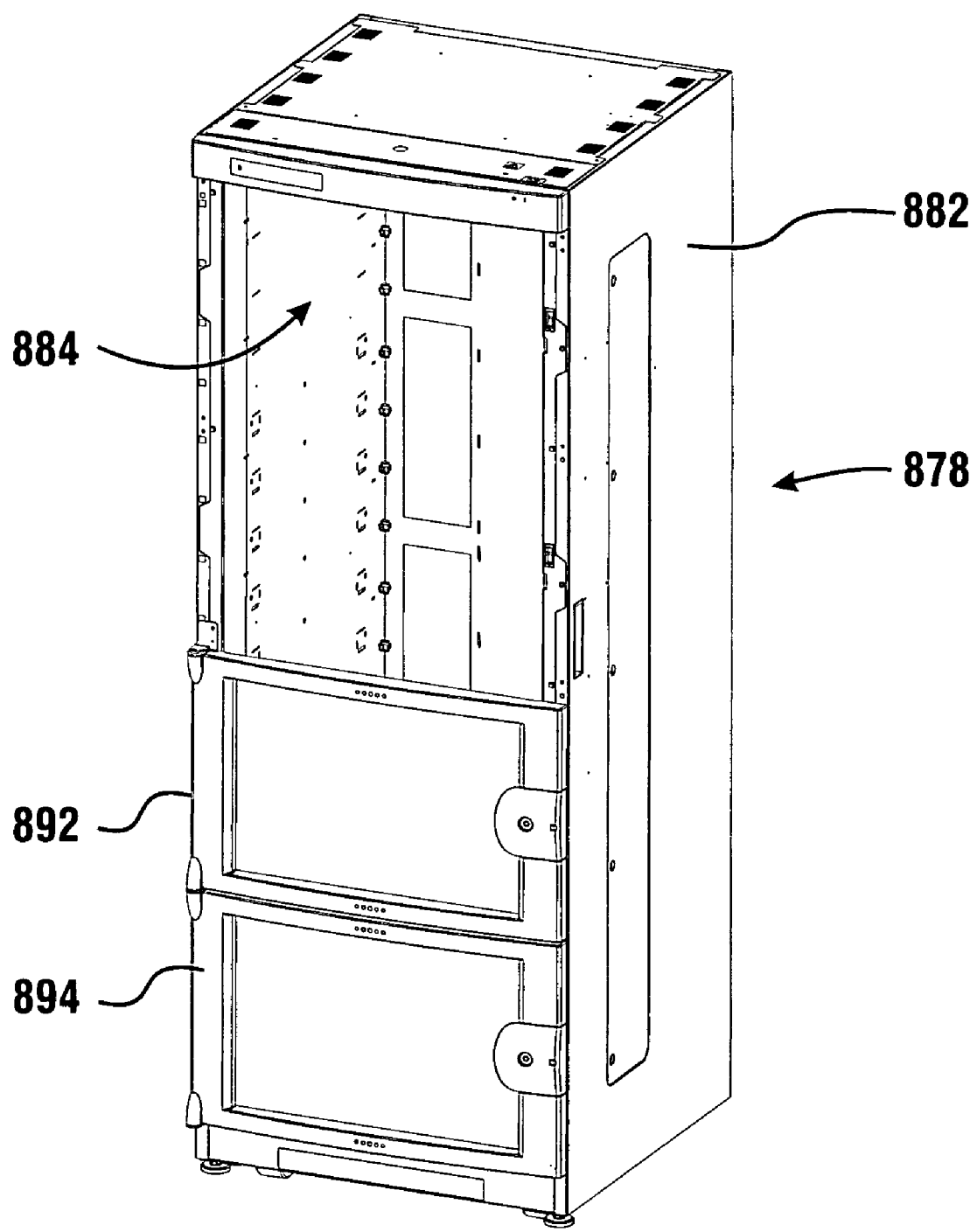
FIG. 9 is an isometric view of the cabinet shown in FIG. 2 showing the interior features used for mounting stationary and pullout shelves.

FIG. 9 shows the cabinet 878 in a state of partial assembly in which only two of the doors have been installed thereon. As can be seen in FIG. 9, the interior area 884 of the housing 882 is bounded by walls which include mounting means therein. These mounting means in the exemplary embodiment include perforations in inner walls which are suitable for supporting brackets. Such brackets may be stationary brackets such as are used with stationary shelves or slide brackets such as may be used to support pullout shelves. Also in the exemplary form of the invention, housing 882 is constructed such that the doors may be mounted through hinges in a left hand or right hand configuration on the cabinet. This facilitates flexibility in the construction and enables convenient mounting of the cabinet so as to be readily accessible even when the cabinet is positioned adjacent to walls, doors and the like. As can be appreciated, in the exemplary embodiment the cabinet doors are made generally symmetrical such that the doors may be mounted to the cabinet in a left hand or right hand configuration by inverse mounting. The vertically extending side walls of the housing are made such that openings are provided in each for mounting the door hinge supports and mounting associated parts of the locking mechanisms on either side of the cabinet. This further facilitates flexibility of the system. It should be understood, however, that embodiments of the invention need not necessarily include these features.

Figure 10:
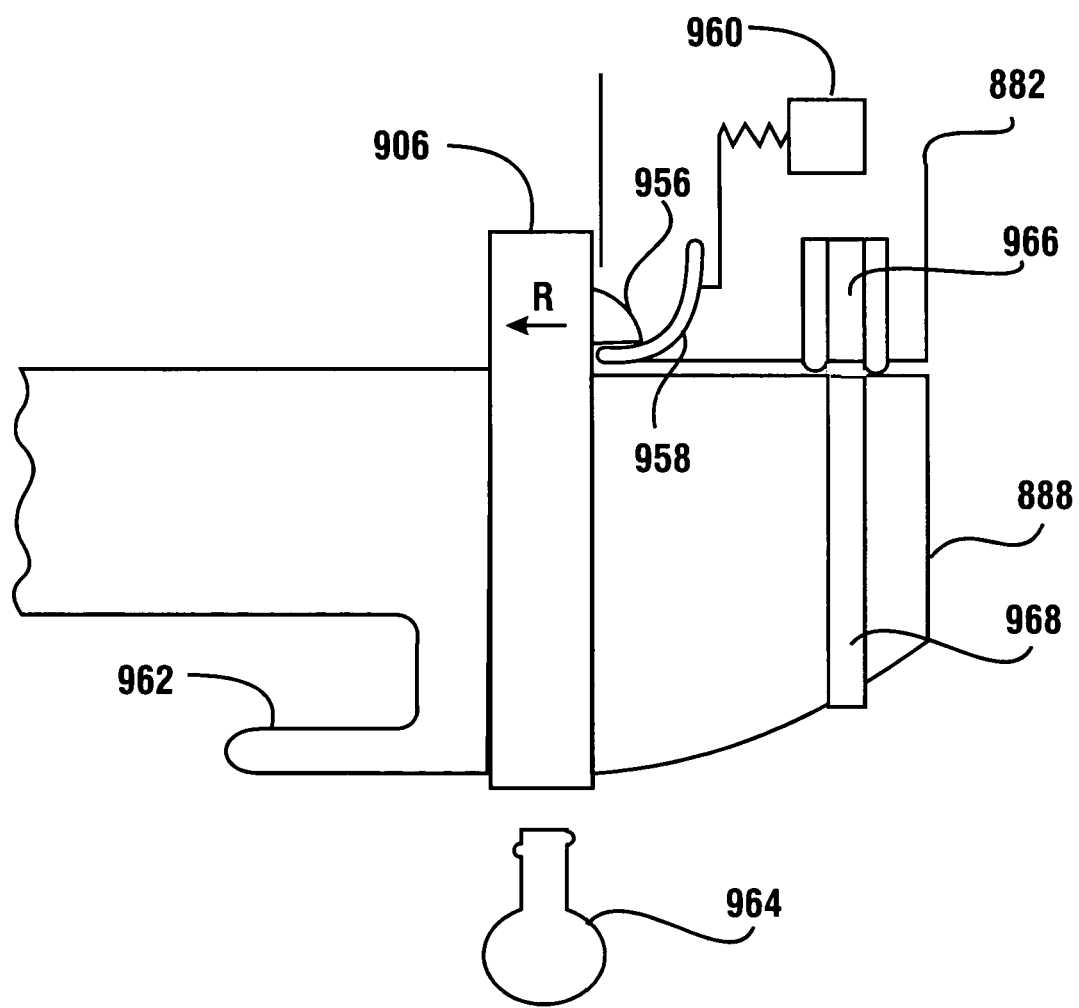
FIG. 10 is a top cross-sectional view of the light indicator on a door of the supply cabinet shown in FIG. 2.

FIG. 10 shows a top schematic view of an exemplary door 888 in closed position adjacent to housing 882. The right hand side of the door as shown is positioned adjacent to the vertically extending side wall of the housing 882. The bolt 906 which is operatively attached to the door includes a retractable portion 956. Retractable portion 956 normally extends outward from the bolt. As shown in the closed position of the door, the retractable portion 956 engages a striker plate 958 in supporting connection with the cabinet wall. Striker plate 958 is in operative connection with an actuator 960. In the position of the striker plate shown in FIG. 10, the striker plate 958 prevents the retractable portion 956 from moving forward as shown and thus maintains the door 888 closed when in a locked position. In response to electrical signals from the display terminal or other device, the actuator 960 is enabled to move the striker plate 958 such that the portion 950 is no longer prevented from moving forward thereby. This enables the door 888 to be opened. Outward movement of the door is facilitated by a handle portion 962 on the exterior of the door frame.

In the exemplary embodiment, the bolt 906 may alternatively be actuated through a mechanical locking mechanism using a key schematically shown as 964. By insertion of the key into an external lock mechanical actuator connected to the bolt, the retractable portion 956 is enabled to be retracted in the direction of arrow "R" in FIG. 10. This enables the door 888 to be opened even though the actuator 960 of the lock is not electronically opened by the display terminal. In this way, the interior area of the cabinet may be accessed by authorized persons in cases where there has been a power failure or other malfunction of the system. In an exemplary embodiment holding devices such as spring biased latches, magnetic latches or similar devices are operatively connected to each door. These holding devices operate to keep an unlocked door in a closed position until it is pulled open by a user. This avoids unwanted opening of unlocked doors which may interfere in taking medical items that are accessed behind other doors.

Another useful aspect of the exemplary embodiment of the invention are indicators that are provided on each of the doors without the need for wiring for other electrical connections thereto. This is achieved through use of illuminating devices such as LEDs positioned in the side walls of the housing 882. Such LEDs are represented by LED 966 in FIG. 10. In the closed position of the adjacent door 888, LED 966 is in alignment with a light guide 968 which extends through the door to the face thereof.

In the exemplary embodiment, when the display terminal or other device is operative to actuate actuator 960 so as to open the lock and place the door in an open condition, signals from the display terminal or device are operative to illuminate the associated LED 966. The illumination of the LED is visible through the light guide 968 on the face of the door housing. In this way, a user is given an indication of doors that have been placed in an unlocked condition and which storage locations can be accessed. This construction enables such indications to be given without having lights or other indicators electrically connected in the door.

In some embodiments multiple doors may be connected together. This enables a user to access a larger portion of the interior of the cabinet through a single door opening motion. In such cases all of the electrically activated locks which enable opening of the plurality of connected doors may be activated simultaneously so that the connected doors are unlocked and locked together. In some embodiments the indicators associated with all of the connected doors may be activated to indicate the condition of each one of the doors. Alternatively, systems may be configured so that only a single indicator is activated to indicate the condition of multiple connected doors. In some embodiments the single indicator may be one positioned adjacent to a door handle of the door that is preferably manually engaged when opening the multiple connected doors. Of course in other embodiments other approaches may be used.

The exemplary embodiment of the cabinet 878 provides enhanced resistance to unwanted movement such as tipping. As can be appreciated, if a substantial number of pullout shelves are included in the cabinet, and if a substantial amount of mass is moved outward by extending pullout shelves, the cabinet may have a tendency to tip forward.

Figure 11:
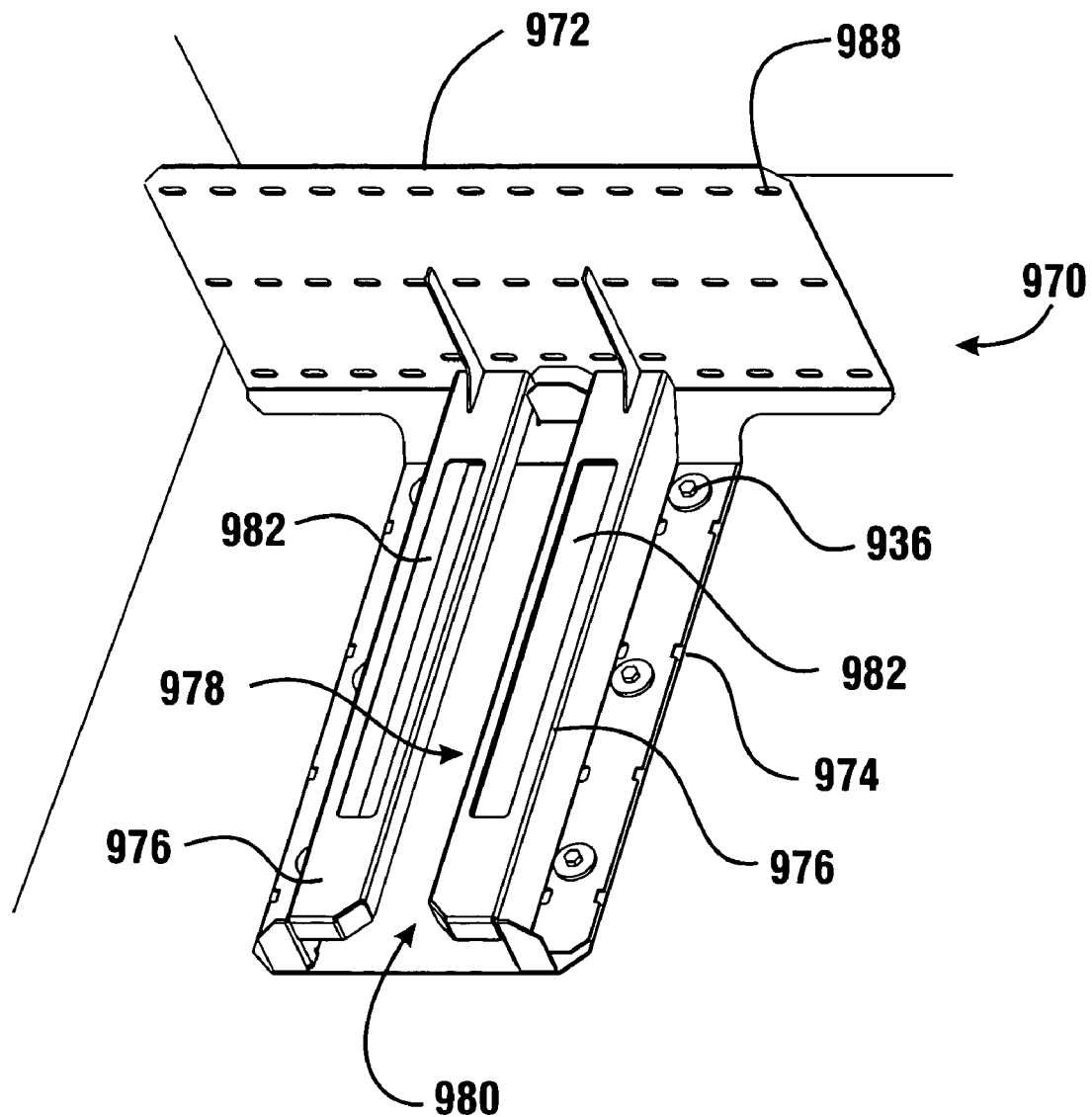
FIG. 11 is an isometric view of a cabinet mounting bracket for mounting the cabinet shown in FIG. 2 in attached relation to a floor surface.
Figure 12:
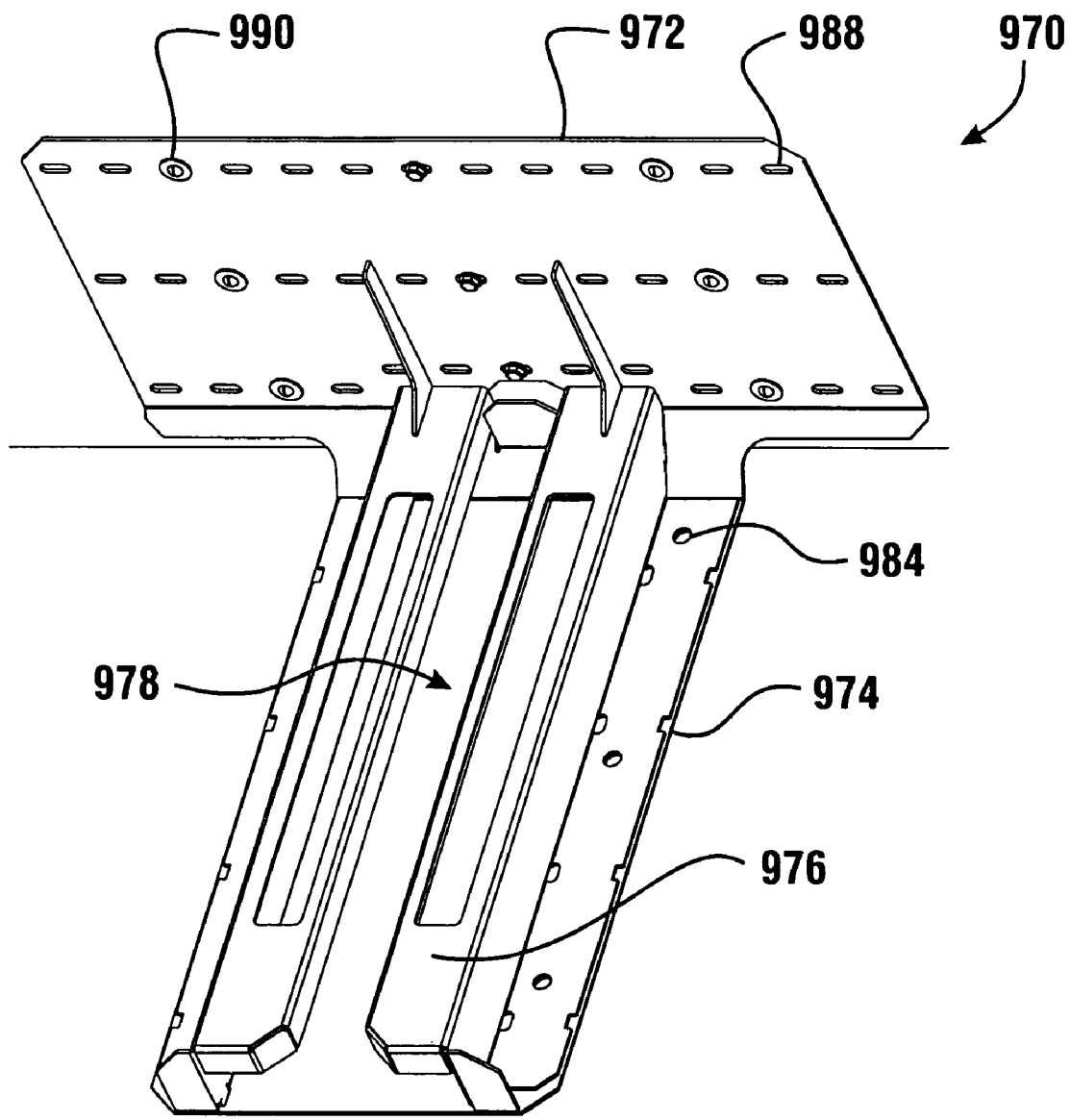
FIG. 12 is a view similar to FIG. 11 with the mounting bracket attached to a wall surface.

To reduce the risk of unwanted movement, cabinet 878 may be mounted using mounting fixture 970 shown in FIGS. 11 and 12. Mounting fixture 970 includes a vertically extending rear flange portion 972. Mounting fixture 970 further includes a lower flange portion 974. A pair of transversely spaced rails 976 extend above the lower flange portion 974. The rails 976 are transversely spaced from one another so as to provide a cross sectional T-shaped slot 978. The rails 976 are shown angled adjacent to the front entrance 980 to the T-shaped slot. Each of the rails 976 include an elongated slot 982, the purpose of which is later described in detail.

The mounting fixture 970 is adapted to be attached in fixed relation to an adjacent floor surface and/or wall surface. As best shown in FIG. 12, the lower flange portion 974 includes spaced apertures 984. As shown in FIG. 11, fasteners 986 may be extended through the apertures 984 to fasten the mounting fixture 970 to a floor surface.

The rear flange portion 972 in the described exemplary embodiment includes three rows of spaced apertures 988. Apertures 988 are spaced so that supports such as wall studs on various spacing can be engaged by extending fasteners such as fasteners 990 shown in FIG. 12, through the apertures. The slotted character of the apertures 988 in the exemplary embodiment facilitate anchoring the rear flange portion 972 to variously spaced wall studs which may be positioned in a wall behind the rear flange portion. Of course it should be understood that fasteners may be used to attach both the rear flange portion and the lower flange portion to adjacent supporting surfaces.

Figure 13:
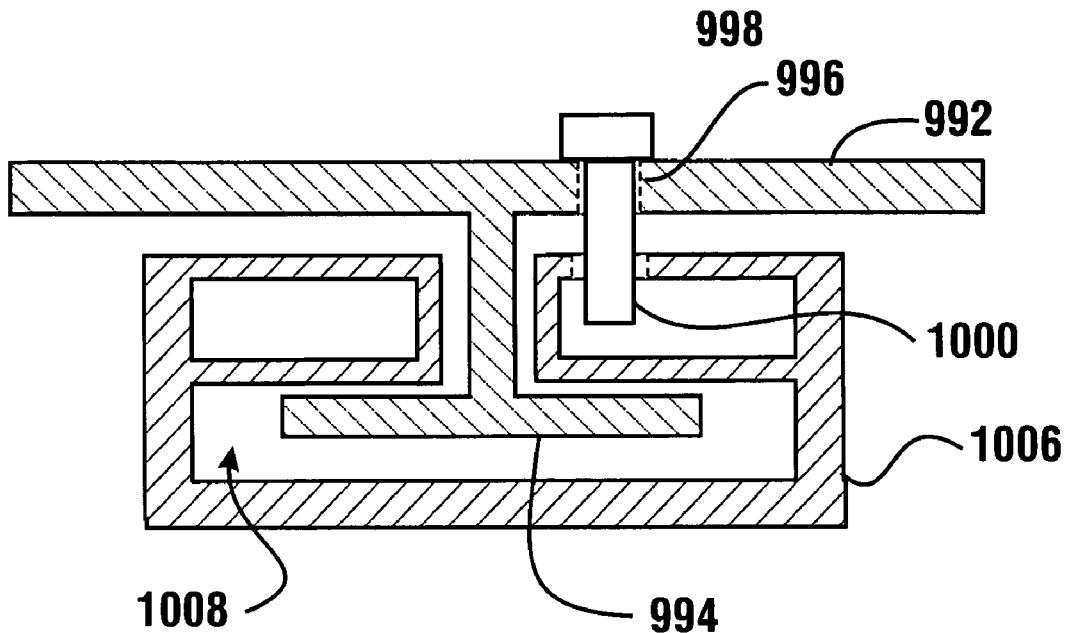
FIG. 13 is a cross-sectional view representative of how the bottom of the cabinet engages the mounting bracket.

In the exemplary embodiment, the housing 882 of cabinet 878 includes a lower wall portion 992. As shown in FIG. 13, lower wall portion 992 is in supporting connection with a generally T-shaped member portion 994. Member portion 994 is sized in cross section to be accepted into slot 978 of mounting fixture 970. As can be appreciated, member portion 994 can be guided into slot 978 through the entrance 980 which is facilitated by the cooperating angled surfaces on the outer end of rails 976.

With the member portion 994 extending in the slot 978, the rails 976 operate to hold the member and thus the cabinet in a generally horizontal position. This minimizes the risk that the cabinet will fall forward even if all the pullout shelves are fully extended.

As shown in FIG. 13, lower wall portion 992 includes at least one aperture 996 extending therethrough. A locking pin 998 or other fastener device or member may be extended through the aperture 996. A distal portion 1000 of a locking pin is operative to extend into the elongated slot 982 once the member 994 has moved substantially into slot 978. The engagement of the distal portion 1000 in the elongated slot 982 enables a cabinet to be moved forward until the distal portion engages the forward bounding surface of the associated elongated slot. This is useful as it allows a service person to move the cabinet away from an associated wall surface while still not operatively disengaging the cabinet from the mounting fixture. Such movement may be useful if one is attempting to access cables or other items which may extend behind the cabinet. Such movement may also be useful for purposes of accessing a lighting element for the interior of the cabinet.

Figure 17:
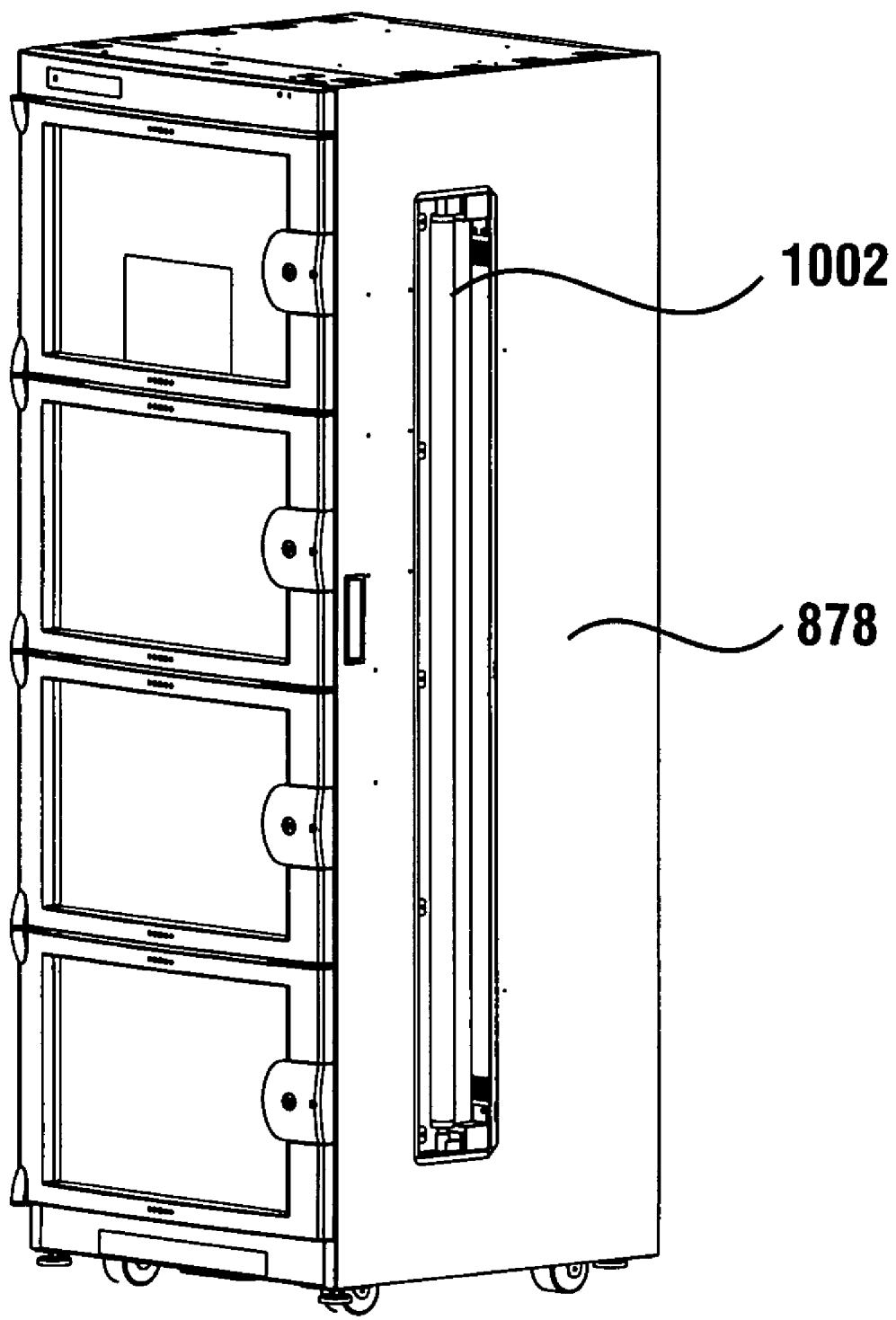
FIG. 17 is an isometric view of a supply cabinet showing a light access cavity including cabinet lights mounted therein.

As shown in FIG. 17, the light access door 900 on the side of the cabinet may be opened to access a tube light 1002. Tube light 1002 serves as a lighting element and is positioned behind a window which allows light to illuminate the interior area of the cabinet 878. As can be appreciated, if the side of the cabinet in which the light access door extends is adjacent to another cabinet or to a wall, the light access door could not be opened until the cabinet is moved sufficiently to provide access for the door to be opened. This may be achieved because the cabinet is moveable along the slot such that the cabinet may be moved forward sufficiently ahead of an adjacent cabinet to provide access sufficient to open the access door and change the tube light. Further, in the described embodiment, the transverse spacing between the rails 976 is sufficient so that the cabinet may be rotated to an extent which allows access to the light compartments or to other items which may be disposed toward one side of or toward the rear of the cabinet. This capability enables working on the cabinet while reducing the risk of disengaging the cabinet from the mounting fixture and causing potential tipping.

It should also be pointed out that the construction of the exemplary form of the cabinet 878 is also useful in that it enables changing the light tube 1002 by persons who do not have access to the interior area 884 of the cabinet. This enables the light tube to be changed by electrical workers or others who need not be provided access to the medical items housed within the cabinet. This avoids time consuming security procedures and observation of service personnel that would otherwise be required if the lighting apparatus were only accessible in the interior cabinet area.

Figure 14:
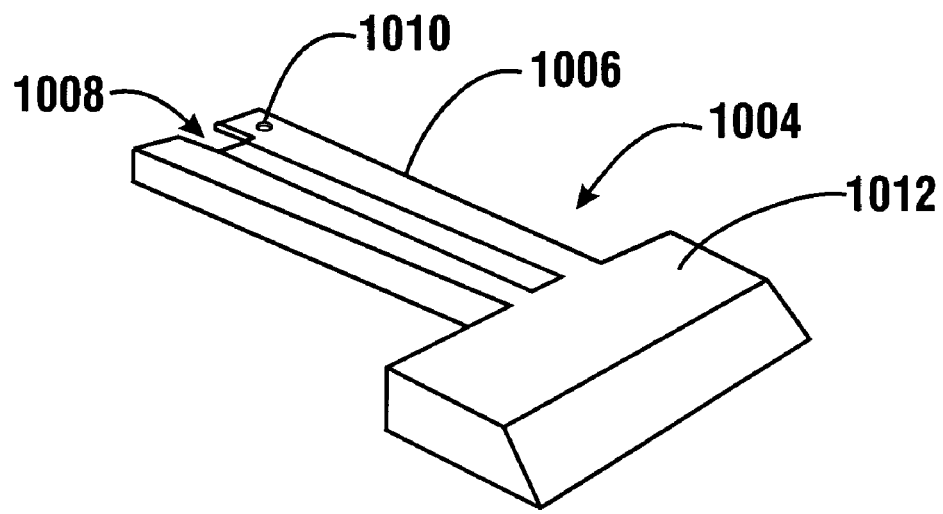
FIG. 14 is an isometric view of an anti-tip fixture for the supply cabinet shown in FIG. 2.

A fixture indicated 1004 and shown in FIG. 14 may be used in connection with cabinets of the exemplary embodiment. Fixture 1004 includes an elongated portion 1006. Elongated portion 1006 has a structure generally similar to the rails of the mounting fixture 970. Elongated portion 1006 includes a generally T-shaped slot 1008. Slot 1008 is sized to accept member portion 994 therein. Elongated portion 1006 further includes an aperture 1010 therein. Aperture 1010 is sized to accept the distal portion 1000 of pin 998 or other fastening device.

Fixture 1004 further includes an enlarged portion 1012 attached to the elongated portion 1006. As shown in FIG. 14, enlarged portion 1012 is substantially wider than the elongated portion and is of a sufficient length to provide enhanced resistance to tipping of the cabinet.

Figure 15:
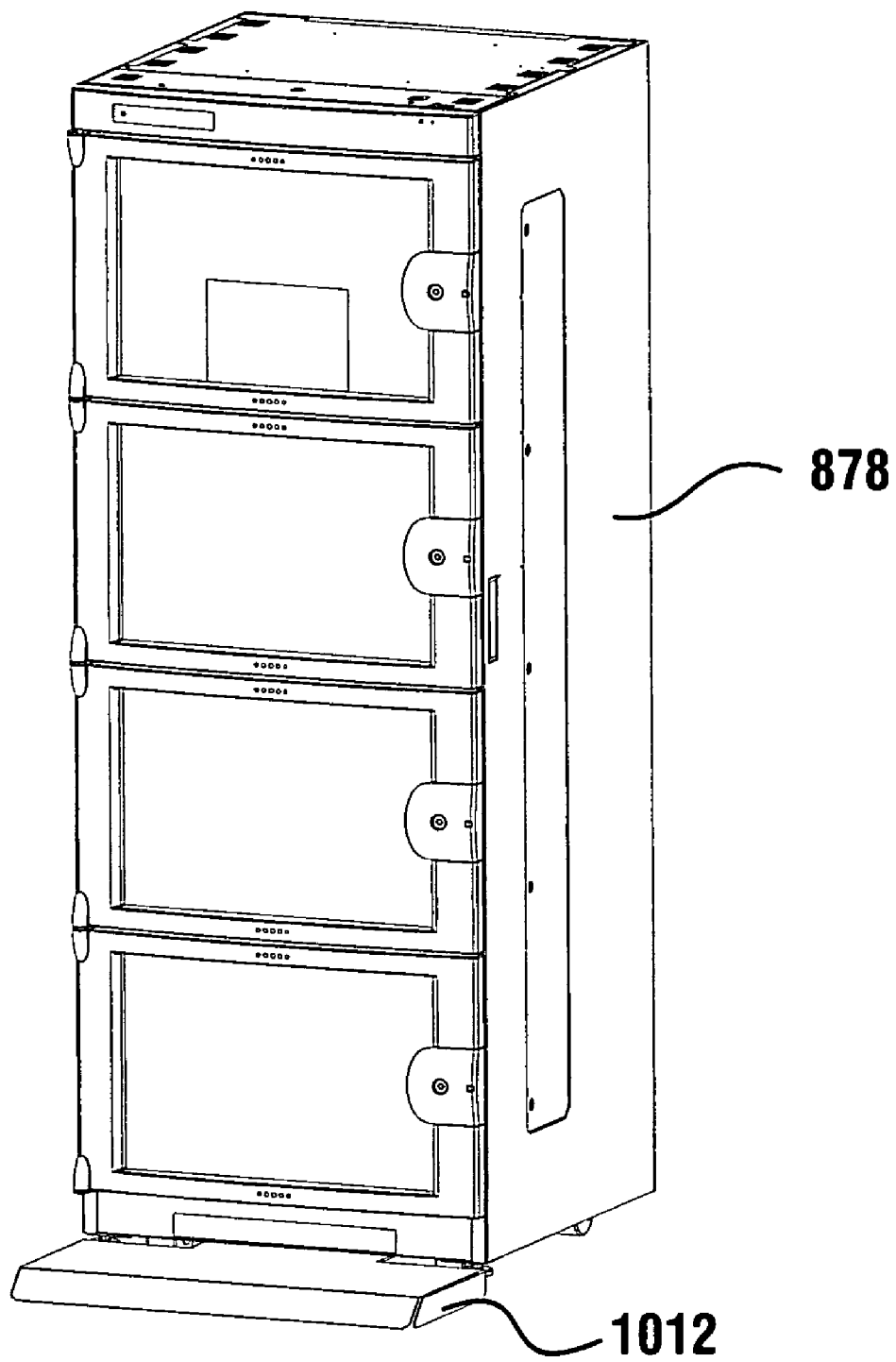
FIG. 15 is a front isometric view showing the cabinet of FIG. 2 engaged with the anti-tip fixture.
Figure 16:
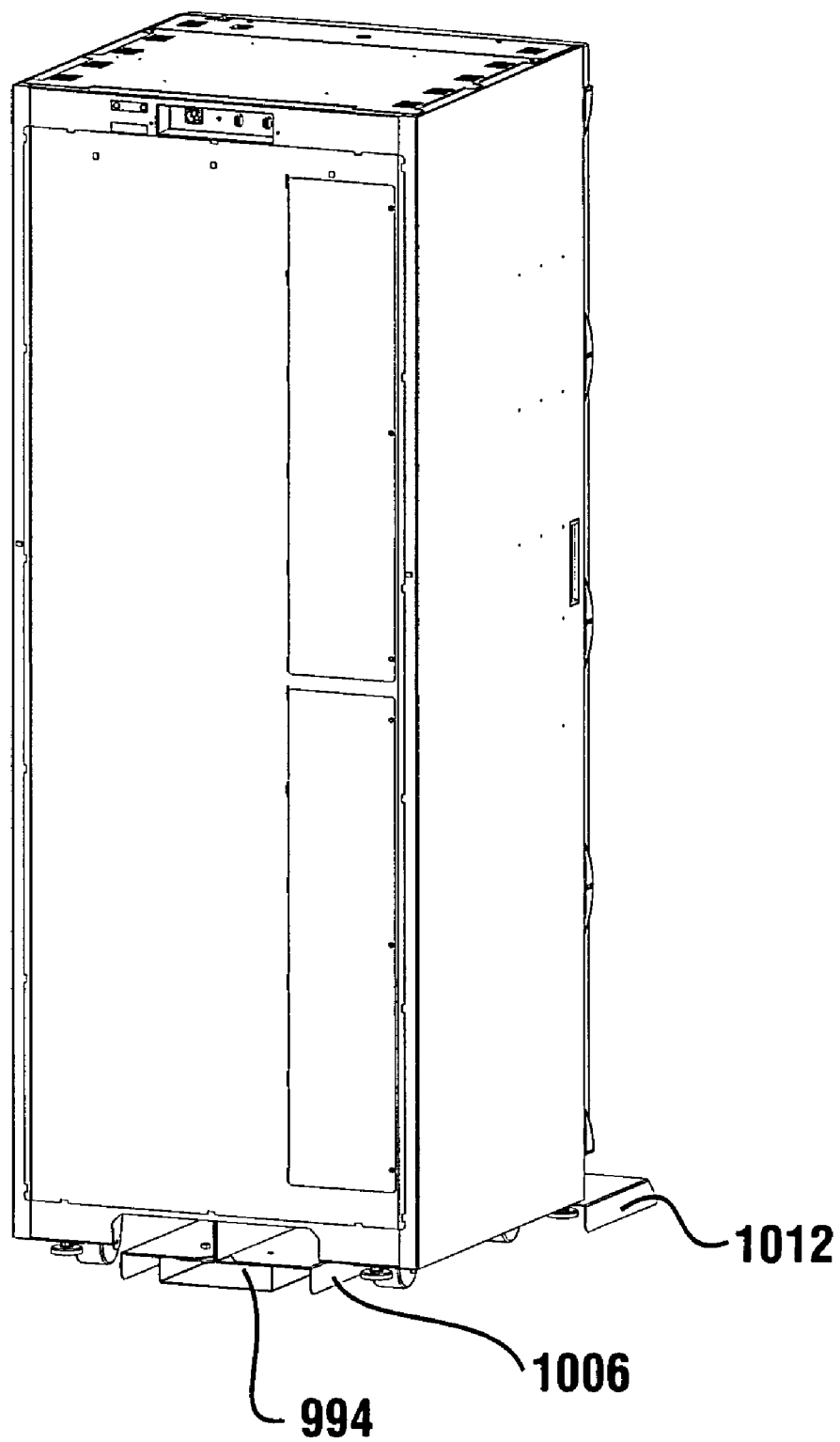
FIG. 16 is a rear isometric view of the cabinet and anti-tip fixture shown in FIG. 15.

Fixture 1004 may be used to minimize the risk of tipping of the cabinet 878 when the cabinet is not engaged with a mounting fixture 970. This may be useful, for example, when the cabinet is being worked on to install shelves or to load materials therein. To install the fixture, the member portion 994 is extended into the slot 1008. The pin 998 is extended through the lower wall portion of the cabinet such that the distal portion 1000 extends in the aperture 1010. With the fixture in this position, the enlarged portion 1012 extends forward of the front of the cabinet as shown in FIGS. 15 and 16. As a result, if the doors are opened and pullout shelves extended, the fixture tends to resist tipping movement of the cabinet in a forward direction. The construction of the fixture 1004 is such that a worker is enabled to readily work in and around the cabinet while it is engaged to the fixture without being hampered thereby. When the work activity is completed, the cabinet doors may be closed and the cabinet moved on its rollers such as casters, or otherwise to a desired position where it may be engaged with a mounting fixture 970. Of course it should be understood that this arrangement is exemplary and in other embodiments of the invention, other approaches may be used.

Figure 18:
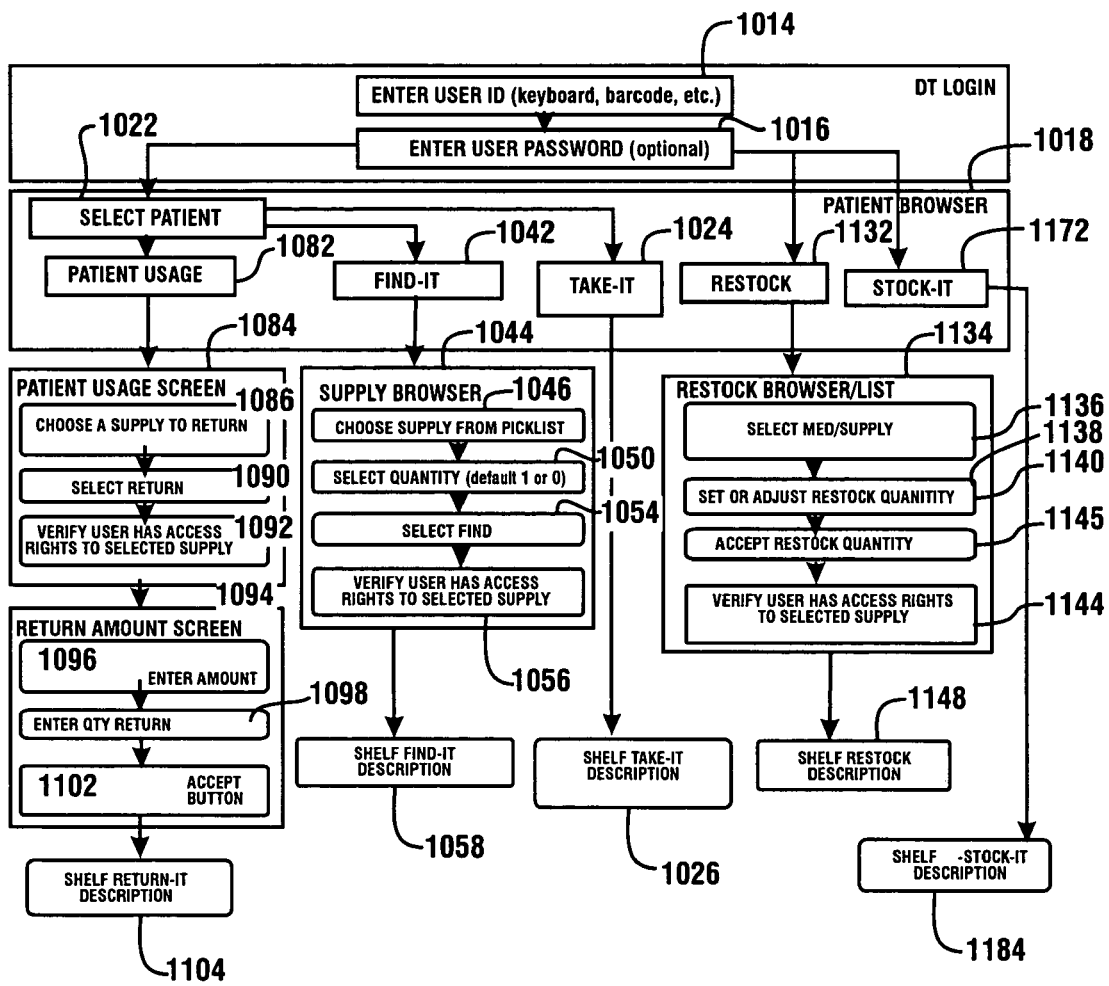
FIG. 18 is a schematic flow diagram showing exemplary operations that are carried out through a system including a display terminal in operative connection with the supply cabinet shown in FIG. 2.

FIG. 18 schematically indicates exemplary logic that is carried out in connection with a display terminal or other computer that controls operation of the supply cabinet 878. In a first step 1014, the user identifies himself to the system so that the system may verify that he is an authorized user. This can be done in any number of ways such as swiping a card which identifies the user, reading the bar code or other machine readable indicia on a badge or other article carried by the user, or inputting identifying information through an input device such as a keyboard. Alternatively, the user may be identified by biometric features such as appearance, voice, iris scan, fingerprint, or other similar feature that identifies the user as an authorized user of the system. In addition, some systems may include a requirement for a user to enter a password either orally or through a keyboard to further verify that the user is an authorized user. This is represented by a step 1016. In response to the input by the user of identifying information, the computer operatively connected to at least one data store holding data representative of authorized users determines if the inputs correspond to an authorized user. If so, the system operates to enable the user to proceed to carry out further steps. Of course if the information input does not correspond to that of an authorized user, further access is denied.

Figure 23:
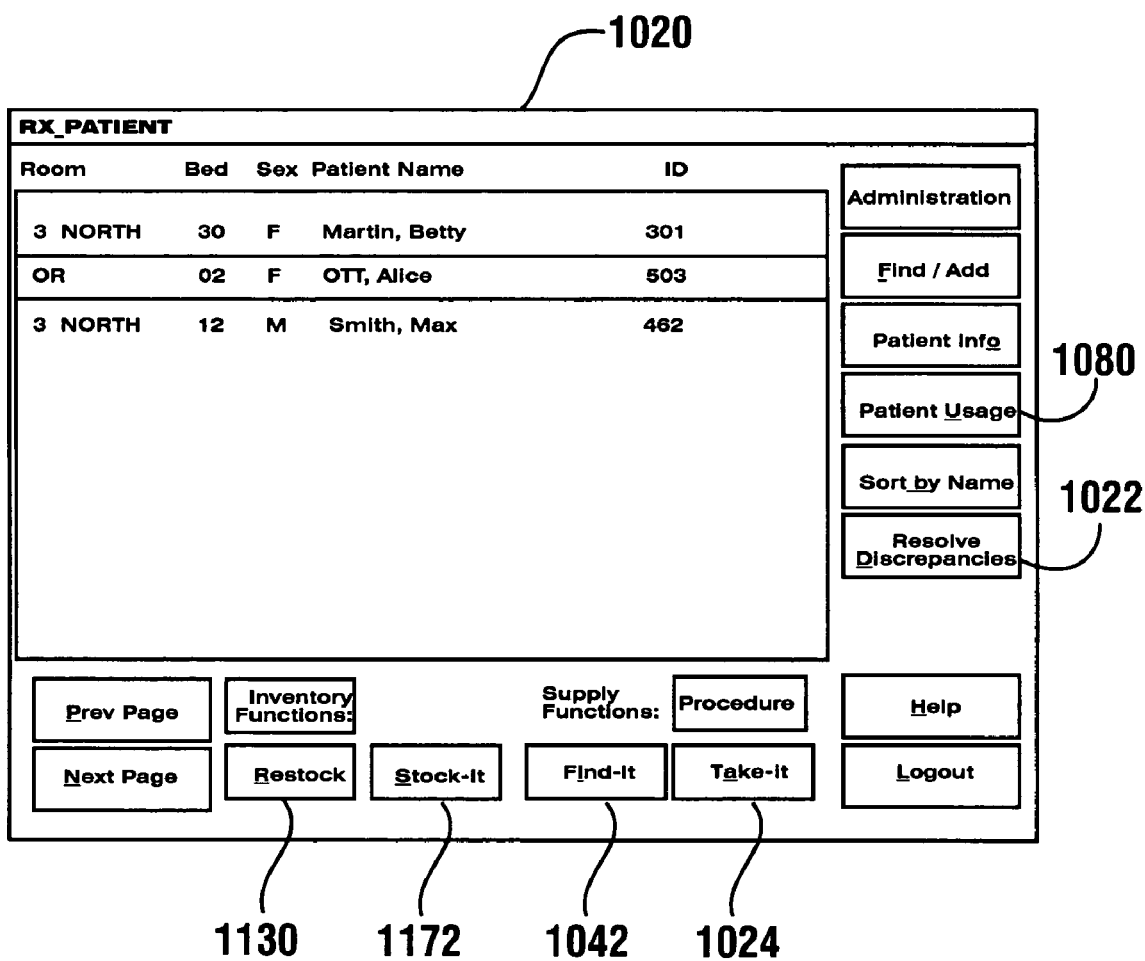
Figure 28:
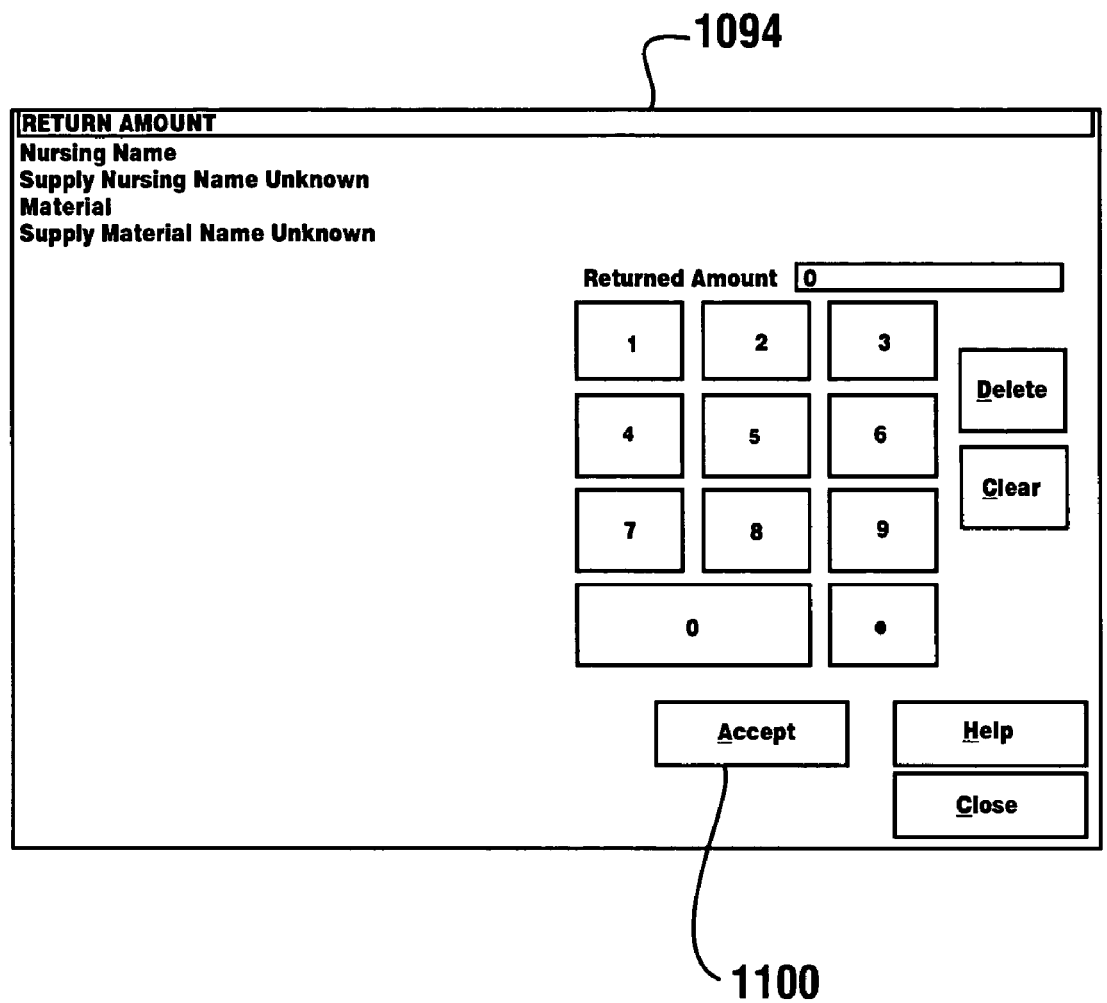

Once the user is determined to be an authorized user, the computer operates in a step 1018 to cause a patient browser screen to be displayed on the display terminal. In a first exemplary embodiment, the patient browser screen is screen 1020 shown in FIG. 23. Screen 1020 is generally similar to the patient browser screen 222 shown in FIG. 28 of the incorporated disclosure of U.S. Pat. No. 5,912,818. Patient browser screen 1020 includes many of the same icons as screen 222 and additional icons relating to operation of the cabinet as later described.

From the patient browser screen, as represented in FIG. 18, a user is enabled to select a particular patient by providing an input in a step 1022. This is done in the described embodiment through the touch screen by the user bringing a finger adjacent to the displayed name of a patient of interest. Upon doing this, the system is operative to cause the name of the patient to be highlighted. This activity further causes the computer to operate so that the data stored in at least one data store in records associated with that particular patient are modified based on further inputs provided to the system.

Upon selecting a particular patient, the user then has several options for activities that may be performed. In situations where the user knows what it is that they need from the cabinet or a group of cabinets for the particular patient, the user can select a "take it" button 1024 from the patient browser screen 1020. This is done by the user providing an input by bringing their finger adjacent to the take it button on the touch screen of the display terminal. In response to the user activating the take it button, the computer is operative to carry out a series of steps 1026.

Figure 19:
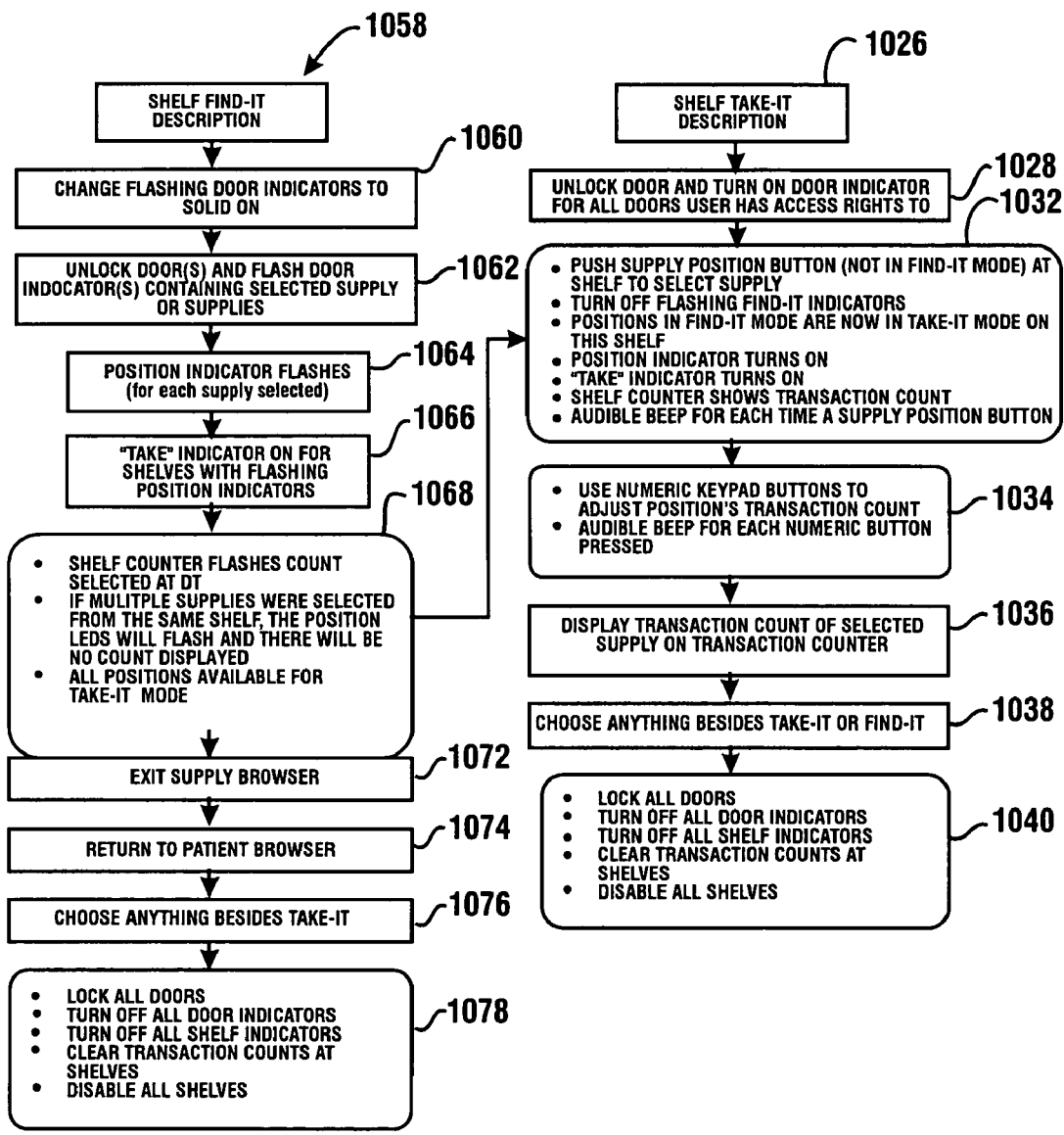
FIGS. 19-22 are flow charts showing exemplary functions carried out through a system including a display terminal in operative connection with the supply cabinet shown in FIG. 2.

The exemplary series of steps 1026 that are carried out in connection with the take it option is shown in FIG. 19. In response to selection of the take it button 1024, the computer is operative in a step 1028 to open all of the doors of the cabinet or a plurality of cabinets connected to the display terminal which house medical items to which the user has access rights. This is based on data stored in one or more data stores concerning the medical items stored in storage locations behind the doors, and stored information concerning the authority of the user to have access thereto. In step 1028, each of the doors holding such items is opened in response to signals from the display terminal that open the electronic locking mechanisms of the doors. In addition, the indicator light associated with each of the doors that have been unlocked is actuated. In the exemplary embodiment, the medical items are stored in the locations such that they are arranged in categories so that no medical items are accessible to a user when a door is unlocked that the particular user is not authorized to have access to.

Figure 5:
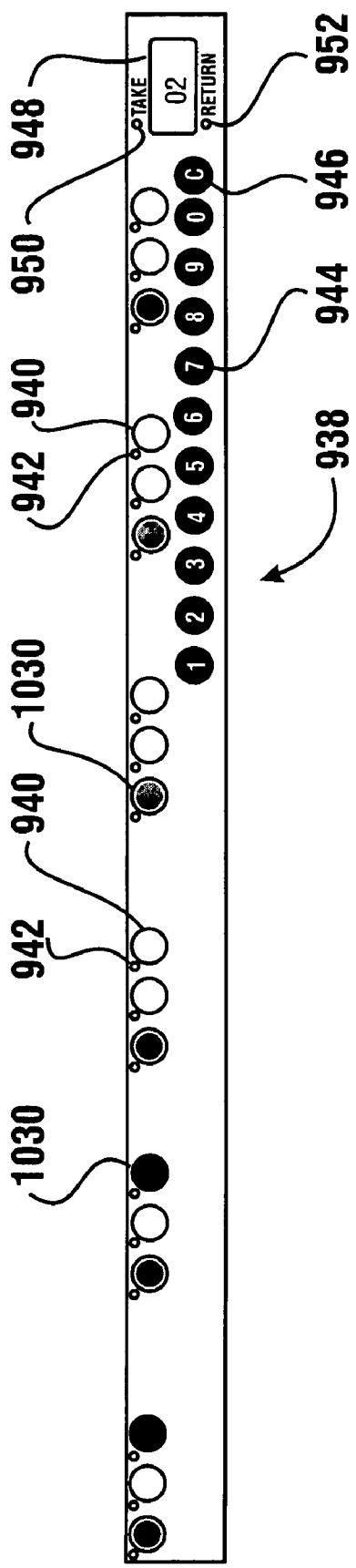
FIG. 5 is a plan view of an exemplary shelf interface.

Once the doors have been opened, the user indicates the position of the medical item that they intend to take by pressing a particular button corresponding to the storage location holding the medical item on the corresponding shelf interface 938. As represented in FIG. 5, buttons 940 which are associated with medical items in the exemplary embodiment have applied thereto a self adhesive label. This self adhesive label is preferably an indicator as to the particular button that is active and distinguishes the button from others which may not be associated with the medical item. Further, in some embodiments of the invention, the label that is applied to active buttons is correlation coded with a storage location through visible indicia such as through a color code. Labels or other indicators of a corresponding type, such as a label having the same color, may be placed or applied in storage locations to which the button corresponds. In this way, a user is enabled to correlate a particular button with the storage location for a particular medical item by correlating the color label on the button to the color label in the storage location. In FIG. 5, color labels on selected ones of buttons 940 are indicated 1030. In situations such as with pullout shelves, each of the active buttons 940 on a particular shelf interface may have a different color. Alternatively, a series of different colors may be used such that the closest button on a shelf (or on a support module) of a given color corresponds to the closest storage location on the shelf (or support module) labeled with the same color. Of course it should be understood that in situations such as with stationary shelves where there may be a small number of medical item types or perhaps only even one item, it may not be necessary to color code the particular storage locations and it would be sufficient to apply a color label 1030 to the active button(s) to indicate which of the buttons are operative. This feature enables a common shelf interface to be used with various shelves and with various numbers and arrangements of storage locations. It should be understood, however, that the use of color coding is exemplary, and in other embodiments, other types of approaches to correlating buttons or other indicators and storage locations may be used.

Returning to the description of the "take it" operation in FIG. 19, the user touches the corresponding button 940 for the medical item being taken in a step 1032. In response to the particular button being pressed, the associated indicator 942 is illuminated on the shelf interface. The user then inputs through the numeric keypad 944 a particular number corresponding to the quantity of that type medical item being taken. The user does this by pressing the numerical indicators comprising the keypad. As this is done, the number selected is displayed as a numeral through the interface display 948. If the user makes a mistake in inputting the type or number of items taken, the user can clear the incorrect input by pressing the "clear" button 946. This is done in a step 1034. As the user selects the button for a particular medical item and provides numerical inputs, the type of medical item selected and the quantity indicated as being taken is displayed on the screen of the display terminal. This is represented in a step 1036. Once the user has selected a particular medical item from one storage location, the user may take a different type of medical item from the same shelf or from a different shelf to which they have access. In doing this, the process described of touching the associated button and providing the numerical input through the keypad is repeated. As the user selects items in this manner, one or more connected computers, such as the display terminal, operate at that time or at a later time to record the taking of these medical items for the particular patient selected in at least one data store.

In some embodiments a user may alternatively use a reader such as reading device 844, to indicate the taking of items. For example, medical items may be labeled with machine readable indicia, such as bar codes. In such cases taking the item from its storage location and scanning the bar code with a bar code reader, causes the system to record that one item has been taken from the corresponding storage location for use in the treatment of the selected patient. Alternatively in some embodiments, storage locations may be labeled with machine readable indicia. In such cases, scanning the storage location may cause the system to record that one item of the type indicated by the system as stored in the location has been taken. Of course, in alternative embodiments machine readable indicia may be read to indicate that scanning indicia on one item is intended to indicate that multiple units of that item are being taken. Alternatively in some embodiments, providing inputs by the reading device through the keypad and on the shelf and/or at the display terminal may be used to indicate that multiple items of the particular type for which indicia have been read by the reading device are being taken.

In alternative embodiments other approaches and reading devices may be used. For example items and/or locations may have machine readable indicia such as RFID tags thereon. Such RFID tags may be read via an RF reader to identify items taken or locations from which items are removed. Of course other machine readably indicia may be used. In some embodiments or for some item types, the use of a reader may be used as an alternative way of providing item and/or quantity data to the system in addition to shelf and display terminal interfaces. In other embodiments, such as where items are stored on shelves in cabinets without interfaces, or where medical items are stored outside of cabinets, the reading device may be used as an alternative to the entry of data through the display terminal. Various approaches may be taken depending on the nature of the system.

Alternatively or in addition, in some embodiments the system may be programmed to enable the user to employ the reading device to verify that they took from storage what they wanted. For example, if a storage location has been labeled to indicate that it holds a certain type item, but the brand or packaging of the item changes, a user may question whether the item taken from the storage location is the item that is expected based on the labeling. In such situations, if the item has indicia thereon, the user can read the indicia with the reading device. In the exemplary embodiment, this causes the display terminal to output an indication of the nature of the item. Further in the exemplary embodiment the display terminal enables a user to selectively view the material and nursing names associated with the particular item. This may enable the user to verify that they have what was desired. Alternatively, a user who has already taken an item and so indicated by inputs to the button and keypad on the shelf interface, can have the item read by a reader to verify the nature of the item. Of course a user may need to indicate a return of an item if the same item is both indicated as taken both through the shelf interface and the reading device. As can be appreciated, reading machine readable indicia may be used in some embodiments to indicate that items are being returned (and credited to a particular patent's account) or restocked. In some embodiments a reading device may be permanently mounted adjacent to a display terminal to facilitate such activities. Of course these approaches are exemplary.

When the user has completed the activity of taking items for the patient, the user may make another selection or provide another form of exit input to the display terminal to close the series of steps associated with taking items for the patient. This is reflected in FIG. 19 in a step 1038. In response to such action, the display terminal or other computer operates in a step 1040 in the exemplary embodiment to lock the doors, clear the shelf indicators and to return to a ready state.

In some circumstances, a particular user may not know exactly where items that are required for a patient are located among storage locations in one or more cabinets. In these circumstances, the system of the exemplary embodiment enables a user to locate a particular item. This is done by the user selecting the patient in the patient browser screen 1020 and then providing an input selecting the "find it" button 1042. As represented in FIG. 18, in the exemplary embodiment selection of the find it button causes the computer to operate to display a supply browser screen 1044 shown in FIG. 24. A supply browser screen is generally similar to screen 264 shown in FIG. 32 of incorporated U.S. Pat. No. 5,912,818 and operates in a generally similar manner.

As represented in FIG. 18, when presented with the supply browser screen 1044, a user is presented with a listing of supplies. The user selects the desired supply from the list by proving an input that comprises touching the touch screen adjacent to the name of the particular medical item. This is represented by a step 1046. In some embodiments the user may then select the desired quantity of the particular item by inputting a quantity by touching a quantity button 1048 on screen 1044. In the exemplary form of the invention, the quantity is set to a default value. The default value may be preferably either a one (1) or a zero (0) depending on the programming of the particular system. The selection of a quantity is represented in FIG. 18 by a step 1050. In alternative embodiments the user may not be presented with the option of entering a quantity. This may be done for example where each shelf in the cabinet has an associated shelf interface and quantities other than the default value of one (1) must be conducted through a "take it" type transaction.

Figure 24:
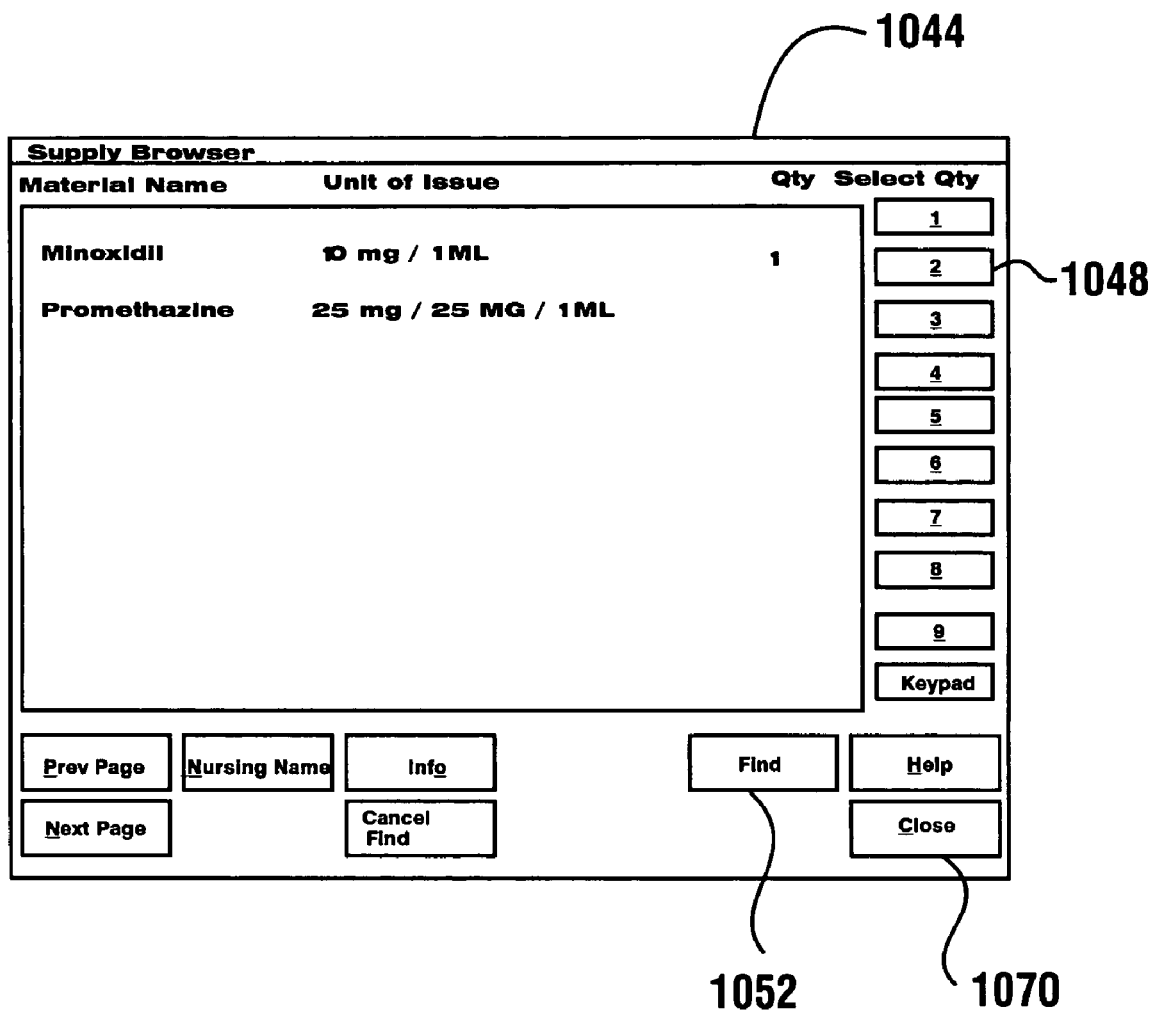

After the user has selected the particular item that they wish to take for the patient and the quantity (if required), the user is guided to the particular item in response to touching a "find" button 1052 shown in FIG. 24. This is represented by a step 1054 in FIG. 18.

In response to the user providing an input corresponding to touching the find button, the computer operates as indicated in FIG. 18 in a step 1056 to determine if the user has a right to access the particular medical item which they have selected. This is done by consulting data in at least one data store. If the computer determines that the user has such rights, the computer operates to execute a series of steps schematically indicated 1058. If the user does not have such rights an indication thereof is output to the user through the display terminal.

The series of steps executed by the computer in an exemplary "find it" operation are shown in FIG. 19. In response to the user selecting a particular item or one or more items, the indicators on the doors controlling access to the shelves holding such items are illuminated and the locks holding such doors in a closed position are caused to be electronically unlocked. This is represented in FIG. 19 by steps 1060 and 1062.

At the same time that the doors are unlocked, the indicator 942 adjacent to the particular button(s) 940 with which the storage location for each selected medical item(s) is activated by being turned on so as to guide the user to the particular location holding each selected item. This is represented in FIG. 19 by a step 1064. At the same time, the take indicator 950 on the shelf interface from which an item is to be taken is illuminated. This is represented in FIG. 19 by a step 1066. The display 948 may also display the particular quantity of the medical item from the particular shelf that was selected through the inputs to the display terminal or the default value in systems where no input is provided. However in an exemplary embodiment, if multiple items have been selected and at least two of those items are located on the same shelf, the display on that shelf does not indicate a number initially. In the described exemplary embodiment, the user, if they do not recall how many of a particular item were requested, may review the supply browser screen on the display terminal. Alternatively in some embodiments, a user can obtain the quantity of a particular item selected by touching the associated button. This causes the number corresponding to the quantity selected to be displayed on the display 948. This is represented in FIG. 19 in a step 1068. Of course in other embodiments other approaches may be used such as cyclically displaying quantities selected with corresponding illumination of position indicators on a shelf interface. In cases where only one item from a shelf has been selected the indicator and quantity for that item may be indicated continuously. Other ways of indicating positions and quantities through a shelf interface will be apparent from the description provided herein.

On occasion, a user who is operating the system in a "find it" operation may determine that they wish to take additional items or quantities that they did not select at the display terminal when selecting medical items. If this occurs in the exemplary embodiment, the user is able to indicate the taking of additional items in a manner similar to that done in the "take it" mode previously described. This is represented in FIG. 19 by the logical connection between step 1068 and step 1032 in the take it operation. In this way, the user is enabled to take whatever medical items they may wish to take from the cabinet through touching multiple buttons and inputting quantities selected. Alternatively or in addition in some embodiments the user can indicate the taking of additional items by reading machine readable indicia with a reading device as previously described. In addition in some alternative embodiments, a user executing a "find it" operation may have the cabinet doors controlling access to all items that the particular user is authorized to have access to unlocked. This enables the user to find not only the particular item they are looking for, but also to access other items in other compartments in the event that they determine that they require such items. In such embodiments the user can select such items by selecting the push buttons corresponding to the items and indicating quantities, as discussed in conjunction with the "take it" function. In addition in some alternative embodiments, the cabinet door controlling access to particular items which the user has selected at the display terminal to have the system find may be indicated in a way that distinguishes them from other cabinet doors that have been unlocked. This may be done, for example, by flashing the indicators associated with such cabinet doors in a different manner or at a different frequency than the other cabinet doors. Of course these approaches are exemplary, and in other embodiments other approaches may be used.

Assuming the user only is taking the items that were originally selected through the display terminal, the user can end the operation by providing an exit input through selecting the close button 1070 in the supply browser screen 1044. This is indicated in FIG. 19 in a step 1072. This causes the system to return the display terminal to the patient browser screen 1020. This is represented in FIG. 19 by a step 1074. If the user provides certain inputs to the system other than those associated with a take it operation as represented in a step 1076, the system operates in a step 1078 to close the transaction. This is done by generating signals that are operative to lock all the doors, turn off the shelf indicators and door indicators, clear the transaction counts of the shelves, and disable the associated shelf interfaces. The data concerning the medical items removed from storage is also stored in a data store. As can be appreciated, the exemplary form of the invention enables a user to have the benefit of locating medical items through inputs that guide the user to the particular storage location. However, the user once access has been provided to the cabinet interior and upon determining that additional items are needed, is provided with the capability of indicating what is to be taken through inputs to the shelf interface. This is often a useful, timesaving feature in certain circumstances. It should be understood however, that in other embodiments, other approaches may be used.

For example, in some exemplary embodiments the process of receiving items may be completed by passing items removed from a storage location past a reading device such as a bar code reader or an RFID type reader in operative connection with the display terminal. The computer operating in the display terminal may be operative to compare the read machine readable indicia from the medical items with the data corresponding to the types of medical items indicated as taken through the other user inputs in the take and/or find logic flow functions. The display terminal or other device may be operative to provide visual and/or audible outputs indicative of the machine-readable indicia associated with the items taken, being in agreement (or not in agreement) with the data associated with the items indicated as taken. In addition, non agreement may provide a user with a warning of a potential error. The computer may be further programmed to receive the data corresponding to the read machine readable indicia and check for correspondence with other input data in an order other than the order in which the user indicated the taking of the items through inputs using a shelf or module interface or the display terminal. This facilitates the user's ability to quickly verify that they have taken the correct items. Such verification may also cause the computer to cause to be stored in at least one data store, data representative of the taking of the medical item for the patient. Of course in other embodiments other approaches may be used.

In the described embodiment of the system, the user is also enabled to return items to storage that were previously taken for a patient and not used. As represented in FIG. 18, to return an item, a user first logs into the system to identify himself as an authorized user through steps 1014 and 1016 previously described. The user then operates to select the particular patient for which an item is being returned through the patient browser screen 1020 and selecting a particular patient as was previously discussed in connection with step 1022. On the patient browser screen, a user may then select a patient usage button 1080 through the touch screen. This is represented by a step 1082 in FIG. 18.

Figure 30:
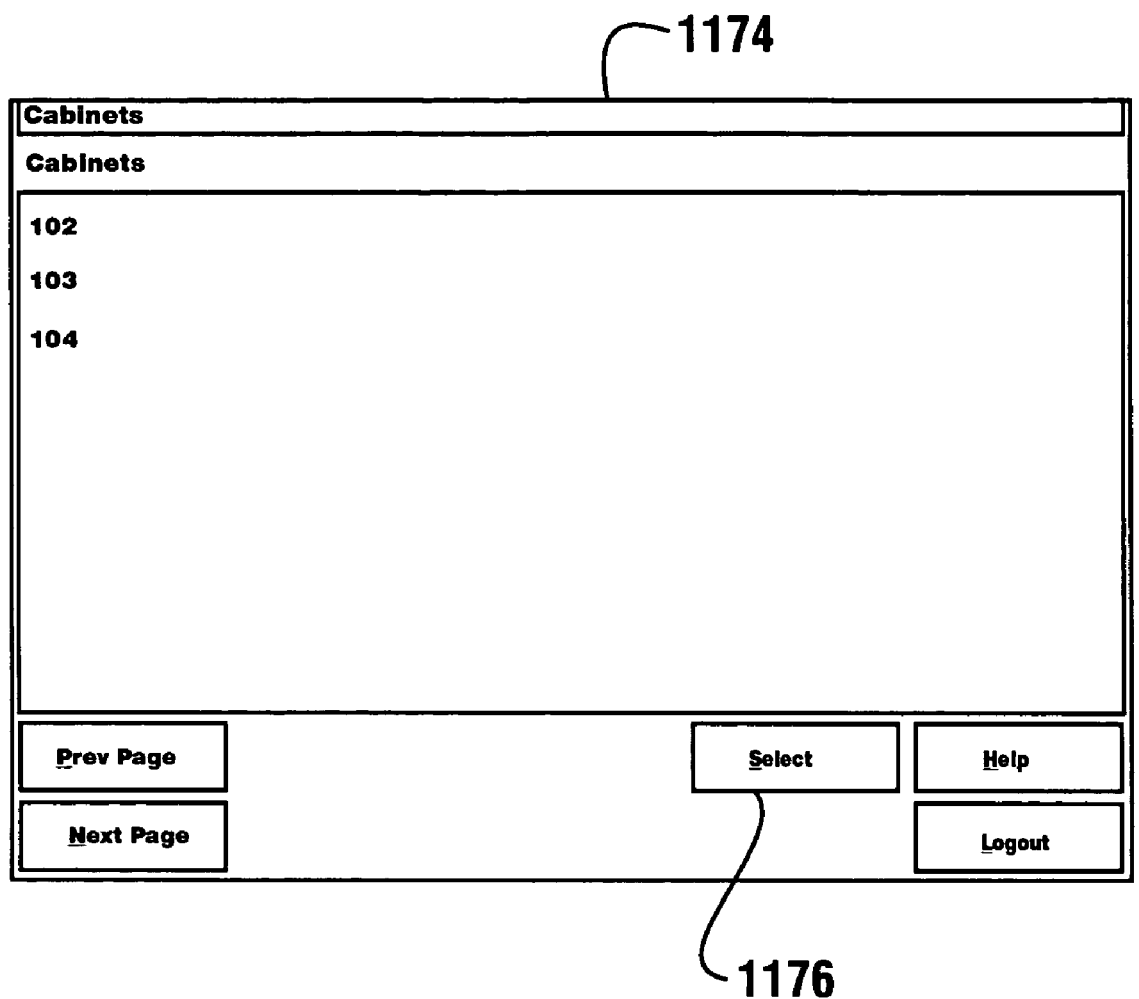

In response to selecting the patient usage button, a patient usage screen is displayed at the display terminal. The patient usage screen is generally similar to screen 244 shown in FIG. 30 of the incorporated U.S. Pat. No. 5,912,818. In the described embodiment, the patient usage screen has a slightly different format shown by screen 1084 shown in FIG. 28. The patient usage screen indicates items that have been taken for a patient. Generally, this will include a plurality of items and the information related thereto.

A user wishing to return a medical item highlights the particular supply to be returned by touching the touch screen adjacent to the particular item. This is represented in FIG. 18 by a step 1086. After selecting the particular item, the user may indicate that they are returning the item by touching the return button 1088 in FIG. 28. This is represented by a step 1090 in FIG. 18.

In response to the user indicating that they are returning an item, the system operates in a step 1092 in a manner like that already discussed to determine if the user has authority to access the particular storage location and/or the group of locations that will be made accessible to the user if the item is returned to its proper storage location.

If the user is authorized to have access to the particular location, the user is presented with a return amount screen 1094 having the layout shown in FIG. 29. On the return amount screen, the user is enabled to select or otherwise input to the system an amount of the supply being returned. This is indicated by a step 1096 in FIG. 18.

The user enters the amount being returned through inputs generated by touching buttons generated on the screen 1094. This is represented in FIG. 18 by a step 1098. Once the user has properly entered the amount of the return, the user can indicate that the information is correct by pressing the accept button 1100. This is represented in FIG. 18 by a step 1102. Of course, if the user makes an error in inputting the information, they can change the inputs through the use of "delete" and "clear" buttons on screen 1094. In addition, if a user determines that they are not going to return a particular item, they may select the "close" button and return to a prior screen.

Figure 20:
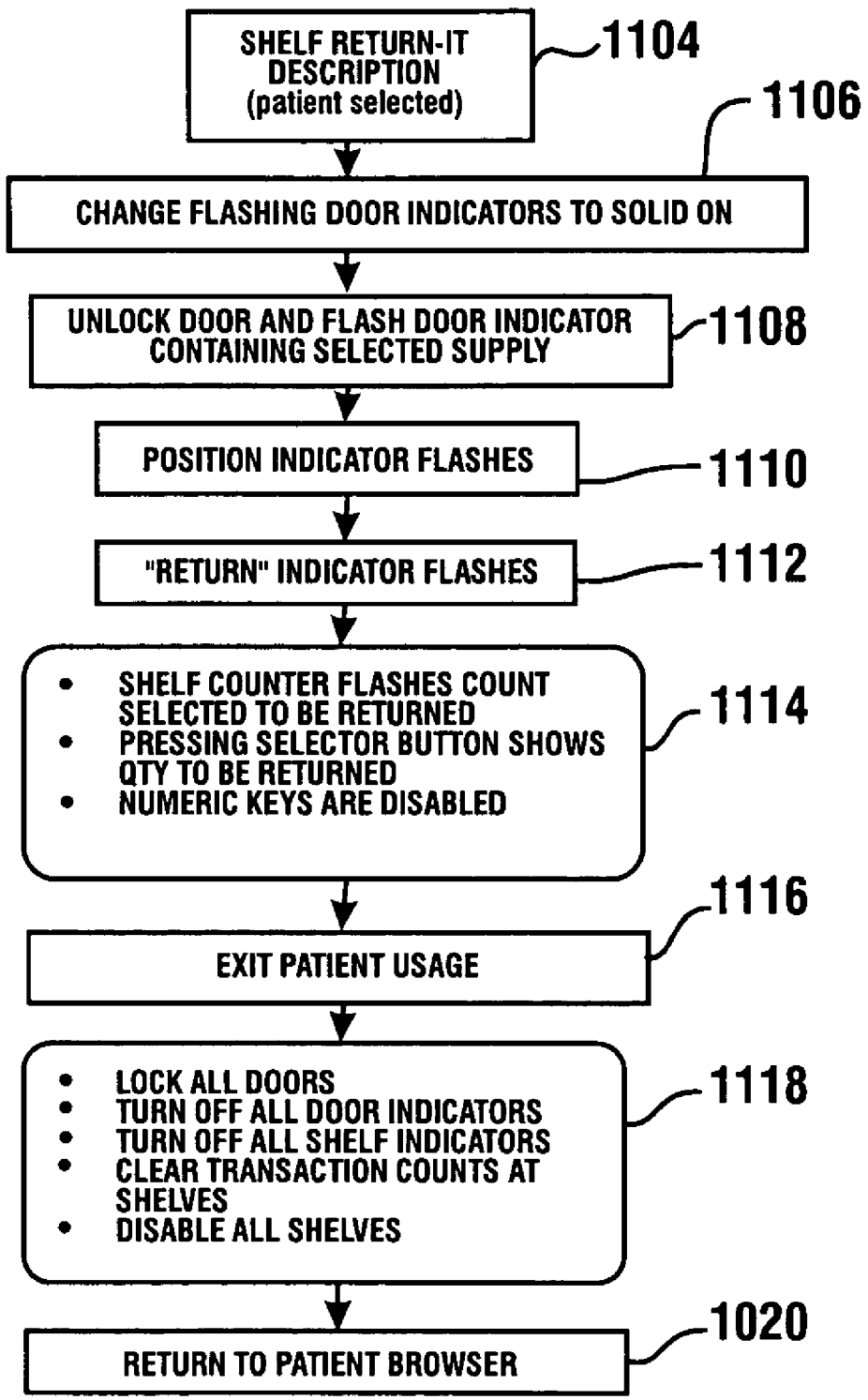

After the user has touched the "accept" button in step 1102, the computer is operative to execute a series of steps 1104. The series of steps 1104 is represented in FIG. 20. The display terminal operates to make the particular storage location for the item to be returned accessible to the user and to guide the user to the particular location. This is done by illuminating the indicator for the particular door holding the storage location for the type of item being returned in a step 1106 while the door is unlocked in a step 1108. Simultaneously, the indicator 942 associated with the button that can be visually correlated with the storage position is illuminated on the particular shelf interface to which the item is to be returned. This is represented by step 1110. Also, the return indicator 952 indicating that an amount is being returned to the shelf is illuminated as indicated by a step 1112. The display 948 on a particular shelf interface shows the particular quantity number to be returned as represented in a step 1114. However, in the exemplary embodiment in circumstances where a number of items have been identified to be returned, and two or more items are positioned on the same shelf, the position indicators 942 will illuminate but the display will not indicate the particular number to be returned. A user can be reminded of a number to be returned to a particular location by touching the button associated with each activated indicator. Doing this causes the display to output the number to be returned to each particular storage location. In this way, a user can be reminded of items to be replaced in each storage location on each shelf. Of course in other embodiments other approaches may be used. In alternative embodiments the system may be programmed to enable the user to change the number of items being returned by touching the button associated with the storage location and entering a different value through the keypad on the shelf.

In the exemplary embodiment, the user may end the return operation by touching the close indicator on the display terminal as represented in a step 1116. This causes the display terminal to return all the doors to the locked condition and to turn off the indicators on the shelves as represented in a step 1118. In alternative embodiments a close indicator may be provided through one or more inputs to a shelf interface or other input device in connection with the terminal. The information concerning the return is stored in a data store. The processor in the display terminal then operates in accordance with its programming to store data in at least one data store to indicate that the returned medical item was returned and not used in treating the patient. The processor also operates to update the data store to include updated number of medical items stored in the storage location based on the prior number and the number of items indicated as returned. The system also then operates in response to the programming of one or more processors in the display terminal to return the display terminal to the patient browser screen as represented in a step 1020.

The described exemplary system also facilitates restocking of the system. As represented in FIG. 18, a restocking user must first identify himself to the system through steps 1014 and 1016 in the manner previously described. This then causes the execution of step 1018 which presents the patient browser screen 1020 shown in FIG. 23. From the presentation of the patient browser screen, a restocking user may select a restock button 1130 which causes the display terminal to execute the step represented 1132 in FIG. 18 which causes a restock browser list to be displayed at the display terminal.

An exemplary form of the restock browser screen 1134 is shown in FIG. 25. Although screen 1134 does not show a listing of positions and material names, it should be understood that such data will be displayed corresponding to some or all positions (alternately referred to herein as storage areas) in which items are stored in the cabinets. A user is enabled to page through the listing of items in the cabinets by using the "previous page" and "next page" buttons in screen 1134.

The user is enabled to select a displayed supply name by providing an input by bringing a finger adjacent to the supply name on the touch screen and then selecting the select button 1135. This is represented in FIG. 18 by a step 1136. The display terminal then operates to cause a stock amount screen 1138 having the format shown in FIG. 26 to be displayed. It should be understood that the stock amount screen will include the information for the particular medical item in the position selected. While the stock amount screen 1138 is displayed, a user can select the restock quantity button 1142. Then, a user is enabled to input a restock quantity through the numeric keys on a keypad display 1139 therein. This is represented in FIG. 18 by a step 1140.

Once the user has input the restock quantity through numeric inputs through the keypad display 1139 the display terminal in response to screen 1138, the user can indicate that they are ready to restock that quantity by touching an accept button 1143 from screen 1138. This is indicated at a step 1145. Of course as can be appreciated, the system functions associated with screen 1138 also facilitates restocking by enabling the restocking user to touch an icon indicating restocking a maximum amount. The user is also enabled to unload items that are stored so as, for example, to make room for additional items by indicating an unload quantity related to the storage location. Buttons are also provided so that a quantity of expired items that have approached the expiration date can be indicated as removed.

Figure 26:
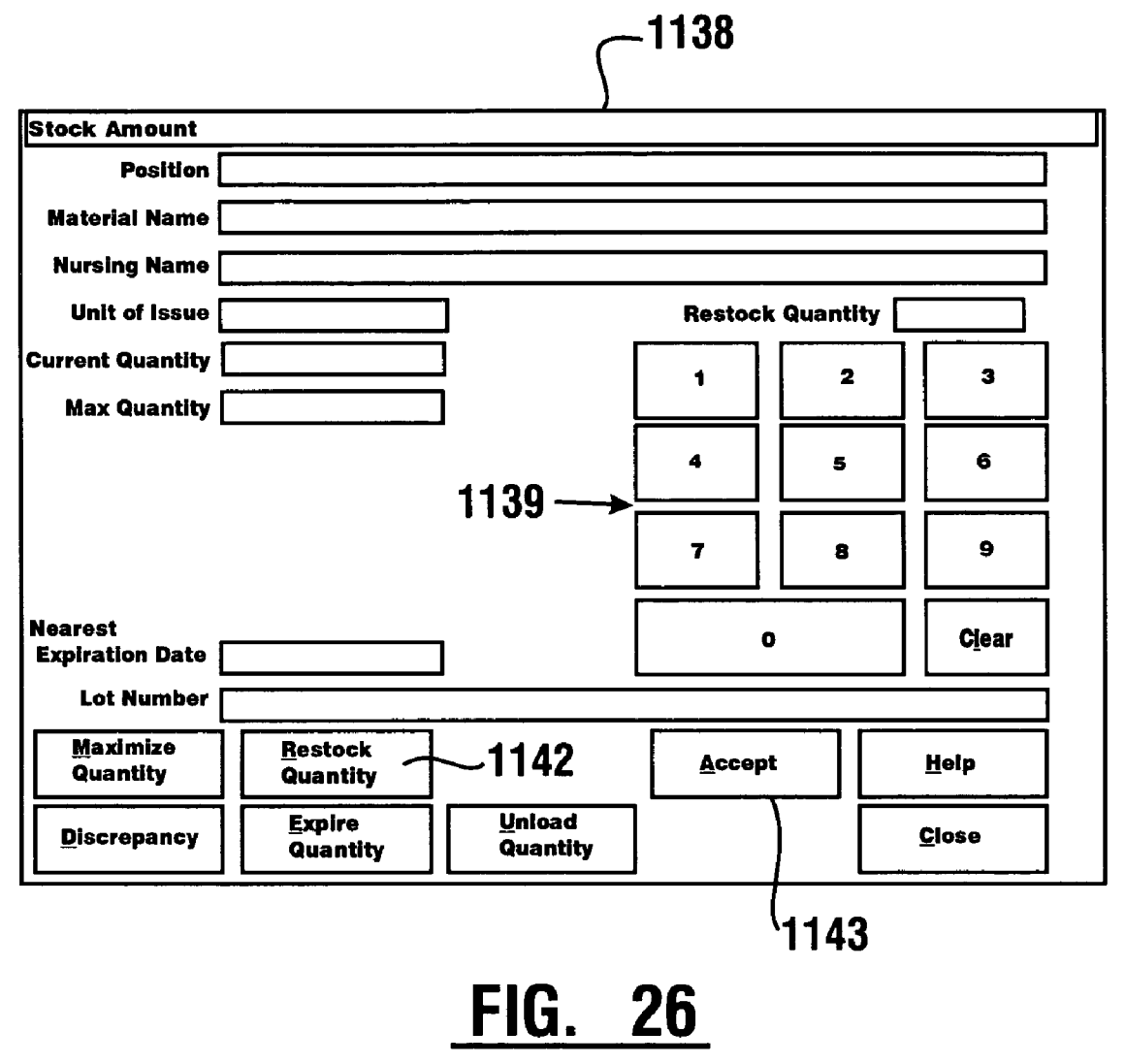

Also, if there are any discrepancies, a discrepancy button is provided such as is shown in FIG. 26 and FIG. 31. Providing an input through the terminal which corresponds to the discrepancy causes the terminal to generate a discrepancy screen enabling the user to indicate any discrepancies to the system and have the information stored in a data store. Screen 1208, having the format shown in FIG. 29 may be used to input the actual number of items in storage when the number recorded in a data store within the system does not reflect that which was actually taken. Screen 1208, populated with data and having the exemplary format shown in FIG. 29 is operative to indicate what the data store indicates is the remaining quantity of items after a particular operation has occurred. This enables a user to indicate any discrepancy related to the number of items that are observed as remaining in a particular storage location as compared to that which the system indicates as remaining after a find it or take it or other transaction. The data input in response to each screen is stored and modifies data that is stored in at least one data store in operative connection with the display terminal. In an exemplary embodiment data corresponding to the discrepancy input is also caused to be stored in the at least one data store. The data stored regarding the discrepancy may include, for example, the identity of the user indicating the discrepancy, the time and date, medical item, storage location and quantity involved. Of course other or different information may be stored in other embodiments. It should be understood that these screens are exemplary and in other embodiments, other or additional types of interfaces and optional inputs may be provided for capturing such information in the system.

In particular with regard to a restocking operation, in response to selecting the accept button 1143 as represented in a step 1144 in FIG. 18, the connected processors in the system operate to determine if the user has rights to access the particular storage location that they are indicating that the user is planning to restock. If the user has authority to restock the particular storage location, the system operates to execute an exemplary series of steps 1148 that are shown in greater detail in FIG. 21.

In response to the restock indication being given, the computer operates to indicate the door behind which the particular storage location is located for the item to be restocked as indicated in a step 1150. This is done by a processor operating to activate the appropriate door indicator. The particular door or doors if multiple items are being returned, are unlocked responsive to signals from the display terminal as indicated in a step 1152. The display terminal further operates in accordance with its programming to place the shelves in a restock mode in a step 1154 and the indicators 942 associated with the buttons for the particular locations indicated as being restocked are illuminated in a step 1156.

As indicated in a step 1158, in the exemplary embodiment if only a single storage location on a shelf is being restocked, the number on display 948 will indicate the number of the particular item to be stocked and the corresponding indicator will be illuminated on the shelf. If multiple items are returned to a particular shelf, the display does not indicate a number until a corresponding button adjacent to an illuminated storage position indicator is pressed. When this occurs, the display indicates the number to be restocked into that particular location. This is represented in a step 1160.

Figure 21:
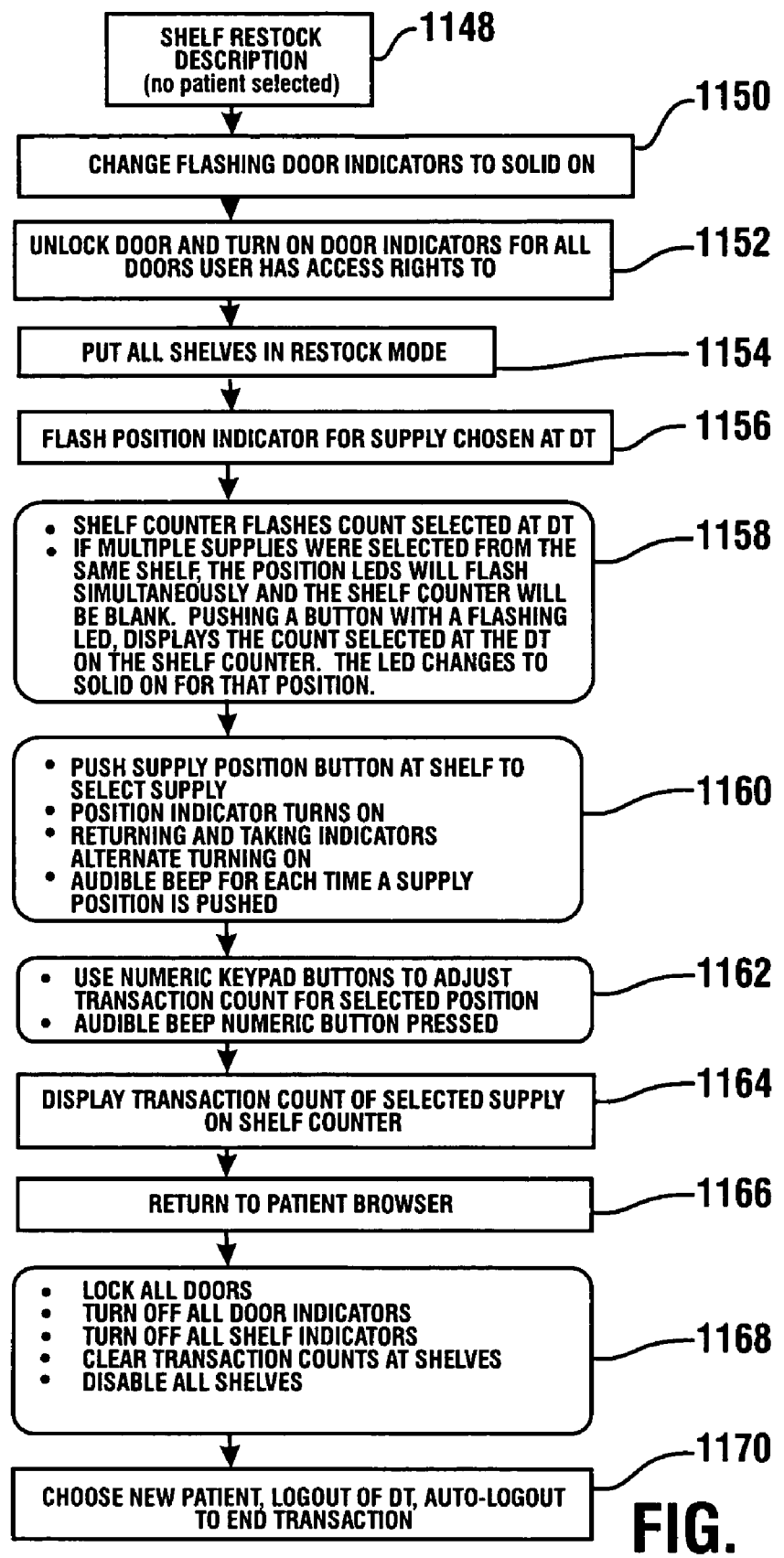

If in the restocking activity it is determined that the quantity to be restocked that has been input at the display terminal was incorrect or if there is a need to restock in additional locations, a user can press a location button 940 on the storage shelf corresponding to the particular storage area and indicate a different quantity to be input through the numerical keypad 944. The count of items is also correspondingly adjusted in the output through the screen provided at the display terminal. This is represented in FIG. 21 by steps 1162 and 1164. When the user has completed the restocking activity, the user may touch the "close" button in the restocking browser screen that causes the display terminal to return to the patient browser screen as represented in a step 1166. At the same time, the display terminal operates to lock all the doors, turn off the indicators and clear shelf interfaces as represented in a step 1168. The data in the at least one data store is also updated and modified responsive to the input data. Thereafter, the user may operate the system to choose a new patient, to log out, or the system may automatically log the user out after a timeout period. This is represented in FIG. 21 by a step 1170. Of course it should be understood that these stocking steps are exemplary and in other embodiments, other approaches may be used and options provided.

The described form of the invention further enables restocking of the cabinets in a predetermined manner based on a listing of restocking activities that has been compiled based on prior information and dispensing activities. For example, in some embodiments, the system may operate to generate a restocking report indicating locations where additional quantities of items are required. A selection of these items may then be compiled in the pharmacy or other location and transported to the particular area for restocking. Alternatively, a listing of such items may be compiled by computers operating in the system in response to a particular request input through the display terminal associated with the particular cabinet. In this way, restocking activities of a plurality of locations may be facilitated without the user having to input through the display terminal inputs corresponding to storage locations.

In the described exemplary embodiment, the stocking activity for cabinets in operative connection with a display terminal may be initiated after the user has logged onto the display terminal in the manner previously discussed by selecting a "stock it" button 1172 from the patient browser screen. This causes the processors connected in the system to generate or call up from memory a restock report related to the cabinets associated with the display terminal. The display terminal then operates to display a cabinet selection screen indicated 1774 and which has the format shown in FIG. 30. The cabinet selection screen 1174 displays a listing of cabinets in connection with the display terminal. A user then highlights a particular cabinet to be restocked and touches a "select" button 1176 to select a particular cabinet that has been highlighted.

In response to selecting a particular cabinet, the system operates to cause a "stock it" screen 1178 having the format shown in FIG. 31 to be displayed on the display terminal. Stock it screen 1178 in embodiments of the invention may reflect the supply positions that are contained in the restock report. It should be understood that although the exemplary format of the stock it screen 1178 does not include this data, in operation when the data is available a listing of such positions and data will be included in the output display screen.

A user is enabled to find particular locations for items by providing an input. This is done by highlighting the item by touching a particular item listed in the screen 1178 and by touching a find button 1180. This causes the display terminal to operate to unlock the doors of the associated cabinet holding such items and to illuminate the location indicators for the buttons that are associated therewith. A restocking user is enabled to locate the particular locations and input the additional items to each as indicated both on the screen 1178 as well as on the display 948 of the shelf interface. A user is enabled to indicate that they have restocked the particular position by touching the accept button 1182 on screen 1178. Touching the accept button will indicate that the particular position or positions have been restocked to the levels desired as indicated in the report. The user may then move to select another item or storage location in the report. The particular doors of the system may or may not be relocked when subsequently closed during this operation depending on the configuration of the system.

Figure 22:
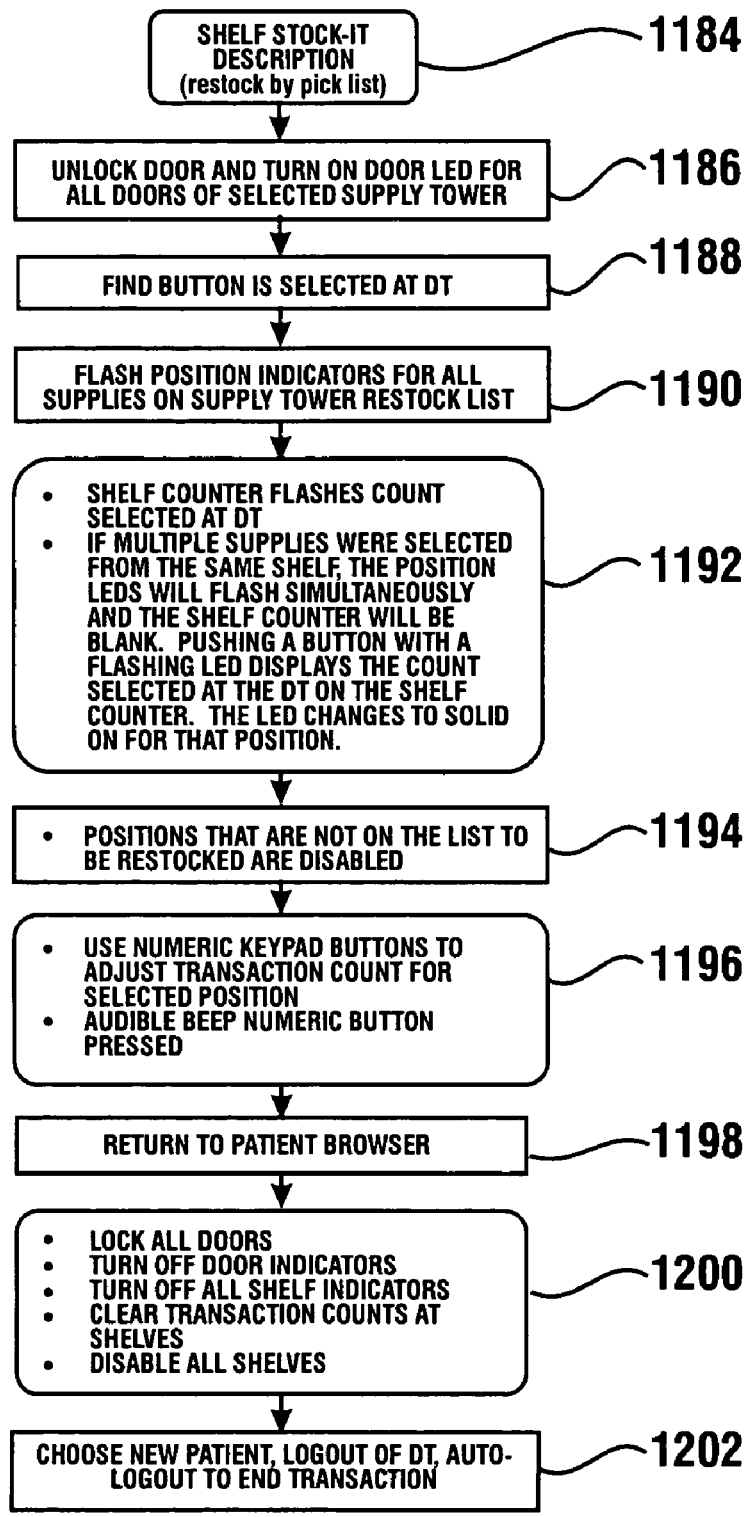

An alternative approach to restocking medical items based on a restocking list is represented by a series of steps 1184 shown in FIG. 22. In this alternative embodiment, selection of the stock it button 1172 from the patient browser screen 1020 causes all of the doors of associated cabinets where restocking is required to be unlocked and the associated door indicators to be illuminated as indicated in a step 1186 in FIG. 22. This results in the stock it screen 1178 or similar screen being displayed at the display terminal. In this alternative configuration, the item is selected for restocking by touching a particular item listed in the screen 1178 shown in FIG. 31 and by touching the accept button 1182 in a step 1188. This causes the display terminal to flash the position indicators for all of the buttons which correlate with storage locations for which restocking is indicated on the list. This is indicated as a step 1190.

As indicated as a step 1192, in situations where a single storage location is being restocked on a shelf, the shelf interface display 948 displays the count or quantity of items to be restocked. In the case where multiple locations are to be restocked on one shelf, the position indicators 942 are illuminated. Pushing the button 940 associated with each illuminated position indicator causes the shelf interface display 948 to indicate the quantity of items to be added to that particular location. As indicated in FIG. 22, the display terminal operates in a step 1194 so that during restocking, the buttons associated with storage locations that are not to be restocked are disabled.

For each storage location where restocking activity is being conducted, the user is enabled to adjust the precalculated count of the number of items to be added to a storage location. This may be accomplished through an optional step 1196 in which alternative numerical inputs indicating the quantity of items to be added to a storage location are indicated through inputs to the keypad 944 after a button corresponding to a storage location has been pressed.

Upon completion of the restock activity, the user indicates completion or that he wishes to close by pressing the "logout" button on the screen of the display terminal. This returns the screen of the display terminal to the login menu as indicated as a step 1198 and updates the information in the database. The display terminal also operates as indicated in a step 1200 to lock the doors and return the indicators to an off position while clearing all quantity indications. Also, if there are any discrepancies, a discrepancy button 1180 is provided which when activated generates a discrepancy screen enabling the user to indicate any discrepancies to the system and have the information stored in a data store. This is similar to the discrepancy function disclosed earlier in connection with the restock function using screen 1208, having the format shown in FIG. 29. As indicated by a step 1202, once the system has returned to the patient browser screen the user is enabled to select a new patient, to log out of the transaction or, alternatively, to allow the transaction to be closed through a timeout which was programmed into the operation of the display terminal. Of course these approaches are merely exemplary, and in other embodiments other approaches may be used.

Figure 35:
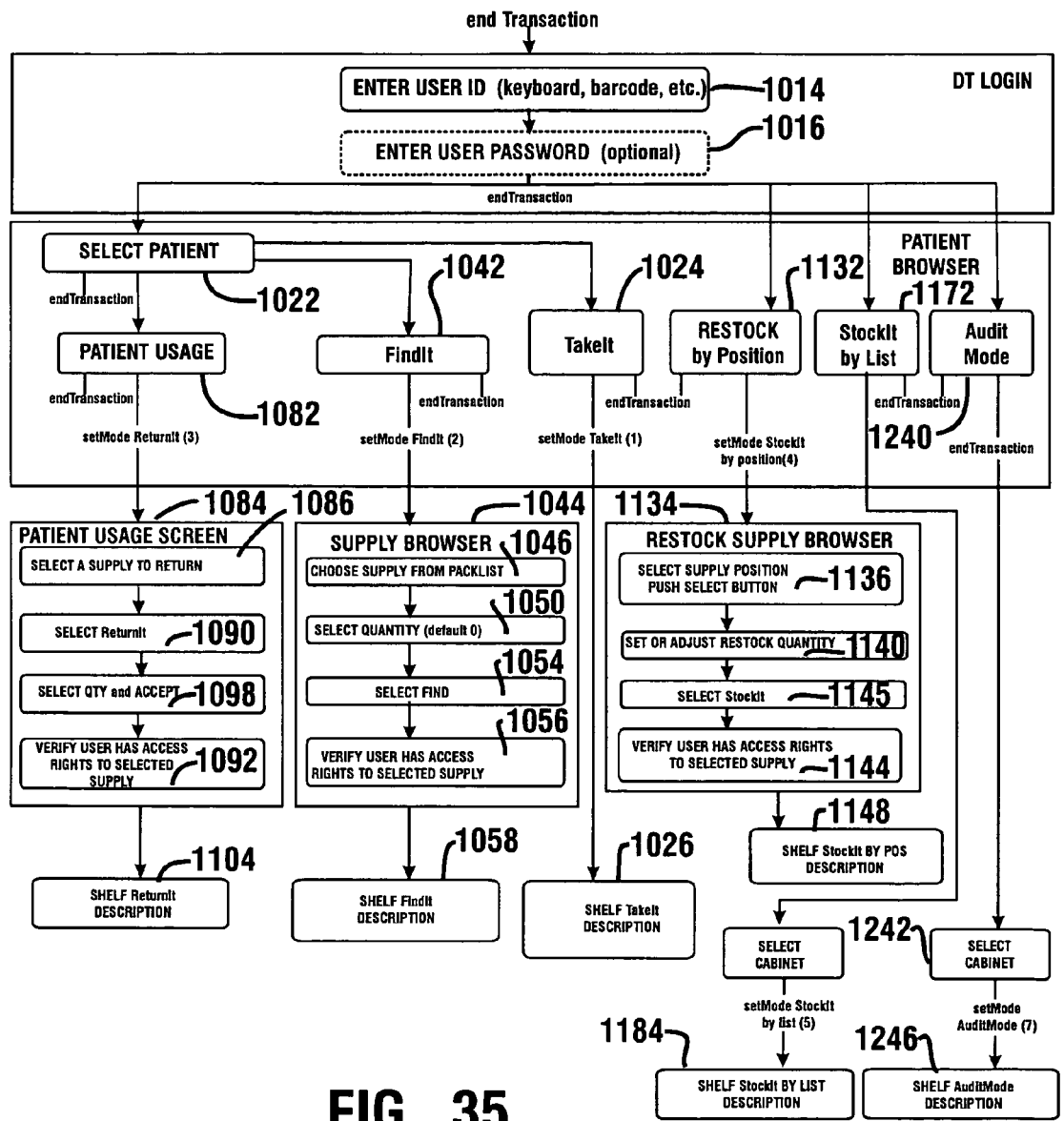
FIG. 35 is a schematic view of a flow diagram showing alternative exemplary operations that can be carried out through the system.

FIG. 35 schematically represents the logic in an alternative exemplary embodiment used by a display terminal or other connected computers in controlling and tracking medical items. The logic represented in FIG. 35 is similar to the logic previously described in connection with FIG. 18, except as specifically noted.

In this alternative embodiment represented in FIG. 35, provision is made for auditing the contents of supply cabinets or other storage locations. This functionality allows supply position counts to be verified and enables the automatic creation of discrepancies for positions whose counts are incorrect. The system is operative to adjust counts in discrepant supply positions. Discrepant events are also stored in one or more associated data stores.

In the exemplary embodiment, the auditing function is enabled to be accessed by users who have the right to access patient data as well as other users who do not have the right to access patient data. For users that have the right to patient data, users enter an identifier (ID) and password in the manner previously described. This results in such users being provided with a patient browser screen 1238, as shown in FIG. 36. Patient browser screen 1238 is generally similar to the patient browser screen 1020 shown in FIG. 23. However, patient browser screen 1238 further includes an audit button 1240.

When the audit button is selected, the system, depending on its programming, may cause an audit witness screen to be displayed. The audit witness screen is presented if the system is programmed so as to require a witness to verify the audit activities of the individual who is logged onto the system. In such cases, the audit witness screen will require the witness to enter identifying information. Of course, in some situations the nature of the supplies being audited or other procedures implemented may not require the presence of a witness.

Figure 39:
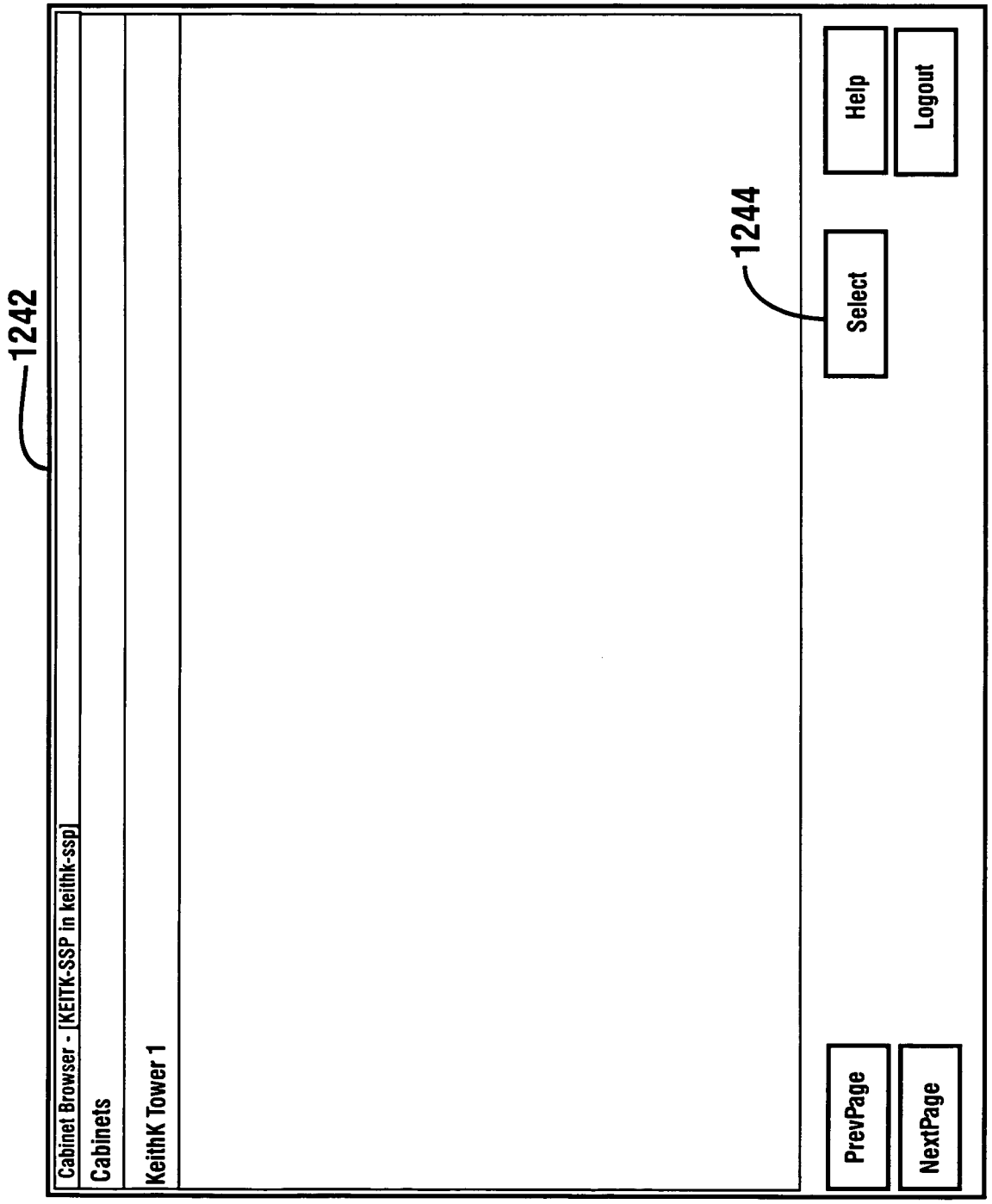

After the information concerning the witness is input, if required, the exemplary system is operative to cause a cabinet browser screen 1242 shown in FIG. 39 to be displayed on the display terminal. The cabinet browser screen in the exemplary embodiment is operative to display indicia corresponding to the cabinets that are connected to the particular display terminal. By providing an appropriate input, a user is enabled to select a particular cabinet to be audited. Of course in some embodiments there may be only one cabinet, and in such cases the audit browser may be eliminated. In the cabinet browser screen shown in FIG. 39 only one cabinet is shown as being connected to the display terminal, but it should be understood that if additional cabinets were connected, each would be listed on the screen and available for selection by the user.

Upon the user highlighting the desired cabinet to be audited and providing an input by selecting the "Select" icon 1244 from the cabinet browser screen, the exemplary system is operative to output through the display terminal an audit browser screen 1246 shown in FIG. 40. The audit browser screen of the exemplary embodiment is operative to list all of the supplies indicated by the system as stored in the current selected cabinet. Because the audit browser screen of the exemplary embodiment appears similar in content to screens used in conjunction with stocking cabinets, provision is made to facilitate a user identifying that the screen is associated with the audit function. In the exemplary embodiment this is done by having the audit browser screen be of a different color than screens associated with stocking functions. Indeed, in some exemplary embodiments, each of the screens associated with different system functions may have a common color scheme or other features unique to that function. This minimizes the risk that a user would be confused in thinking they are providing inputs to the system related to one function when in fact a different function has been selected. Of course, this approach is exemplary, and in other embodiments other approaches may be used.

In the exemplary embodiment, when the audit browser screen is opened, all of the supply cabinet doors to which the user is authorized to have access are unlocked. In the exemplary embodiment the supply browser screen also displays columns which include the supply position description, the supply name, the unit of issue for the supply, the last audit date, the audit quantity and a discrepancy indicator. In the exemplary embodiment, the discrepancy indicator is an icon in the form of a highlighted exclamation point. Of course this approach is merely exemplary of approaches that may be used to indicate medical items and/or storage locations for which a discrepancy has been indicated.

A list of supplies output on the audit browser screen in the exemplary embodiment can be sorted. This can be done either by supply position or the supply name. Further, in the exemplary embodiment provision is made by entering user selections to change the output data between the nursing and material names (for example, brand versus generic names) for the particular supply.

In the exemplary embodiment a supply position can be selected for audit in one of several ways. This can be done, for example, by selecting a position via the touch screen at the display terminal. Alternatively, a position can be selected by pressing the corresponding shelf button. Further, in some exemplary embodiments a supply position can be selected by scanning a supply bar code. This can be done, for example, by scanning with a reading device operatively connected with the display terminal, a bar code or other indicia included on the packaging or the supply itself, or alternatively scanning such indicia from a report. Further in the exemplary embodiment, if a common supply is positioned in multiple storage locations, the system is operative to select the first position from among the multiple positions for audit. Further in an exemplary embodiment, a supply position can be selected by scanning a position bar code or other indicia. A supply position bar code may be positioned adjacent to a particular storage location on a report or in another suitable location. Further in the exemplary embodiment, the audit browser screen 1246 includes an "Audit All" icon 1248 which in the exemplary embodiment is operative to cause the system to automatically iterate through all the storage positions for purposes of performing the audit function.

Figure 41:
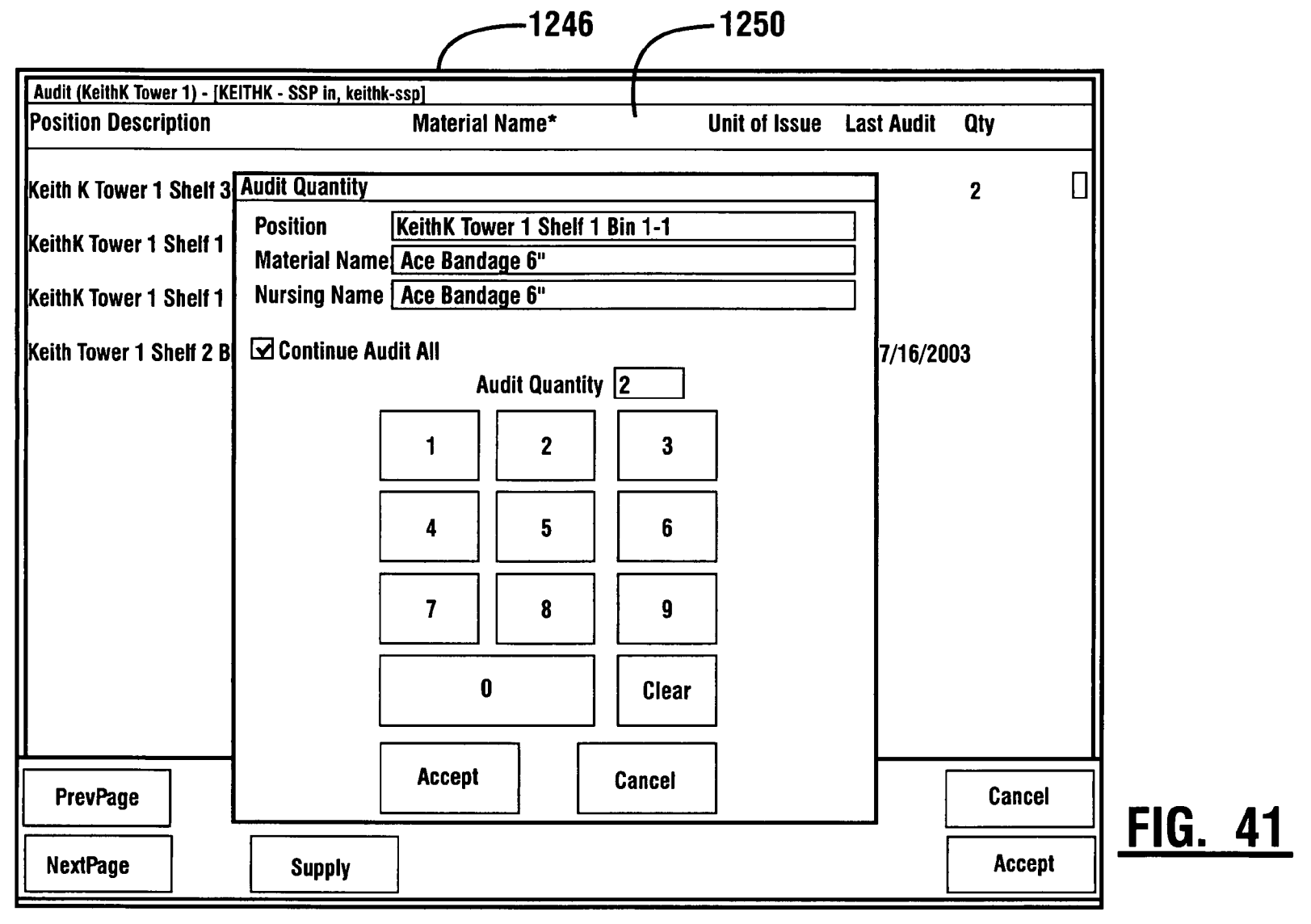

In the exemplary embodiment when a supply is selected, the display terminal is operative to output an audit quantity screen 1250 shown in FIG. 41. The audit quantity screen 1250 in the exemplary embodiment is operative to appear as a window overlying the audit browser screen 1246. In response to presentation of the audit quantity screen, the user enters the quantity through the keypad icons presented on the display terminal screen. After the quantity is entered, the "Accept" icon is manually activated and the connected processors are operative to update the data in at least one data store corresponding to the quantity for the particular type of medical item stored in the particular position. Of course, if as previously discussed the entered quantity does not match the quantity for that supply position then currently stored, a discrepancy indicator appears in the audit browser window and a record of the discrepancy is made in one or more data stores for later resolution.

Alternatively in some embodiments, a particular supply position can be audited by selecting the shelf position by pressing the push button associated therewith. In the exemplary embodiment this then causes the audit quantity screen to be output on the display terminal. Instead of inputting the quantity through the audit quantity screen, however, the quantity within the position may be input through the keypad on a particular storage shelf or support module. Thereafter in the exemplary embodiment the auditing user can indicate acceptance of the quantity by touching the "Accept" button on the audit quantity screen. Of course this approach is exemplary and in other embodiments other approaches may be used. In addition, in the exemplary embodiment of the audit quantity screen 1250, provision is made to enable a user to clear any incorrect inputs that have been provided. This is accomplished by the user selecting the "Clear" button. Thereafter the user can again input a quantity. Further in the exemplary embodiment, the user is enabled to not audit a particular position and automatically continue with a next position. This is accomplished by the user selecting the "Cancel" button in the audit quantity screen.

As previously discussed, the exemplary embodiment also enables the user to select the "Audit All" button from the audit browser screen. In response to selecting this icon, the one or more processors are operative to cause the display terminal to automatically iterate through all the supply positions of the selected supply cabinet. The user is then systematically enabled to enter audit quantities for each such supply position. If for some reason the user does not wish to audit a particular supply position or is unable to do so, the user is enabled to skip the particular position using the "Cancel" button. This enables the exemplary embodiment to enable users to selectively audit particular positions, to audit all positions, or to audit subsets of positions. It further enables exemplary systems to be programmed so that certain positions require witness verification for certain medical items, but not for others. The exemplary embodiments further enable supply positions to be checked by more than one person, so as to reduce the risk of errors or deliberate inaccuracies. Of course these approaches are exemplary, and in other embodiments other approaches may be used.

Figure 37:
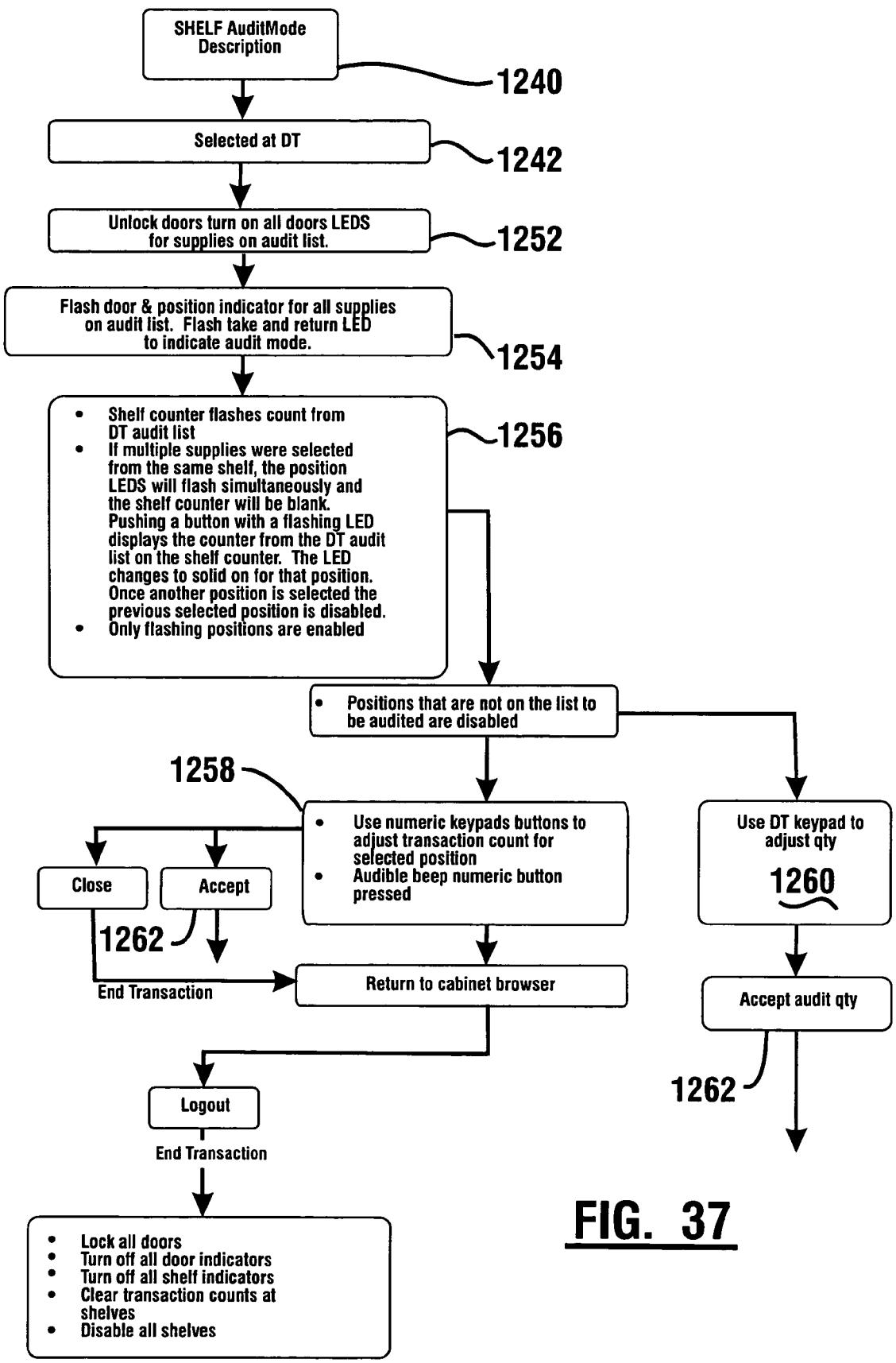
FIG. 37 is a flow chart associated with an audit function carried out through an exemplary embodiment of the system.

An exemplary logic flow associated with the operation of the system in the audit mode is represented in FIG. 37. The logic represented in FIG. 37 represents the logic flow in which medical items are audited. After the audit function is selected by a user touching the audit button 1240, and a cabinet is selected by an input from the cabinet browser screen 1242, the one or more processors associated with the display terminal is operative to output the audit browser screen 1246 and to unlock the doors behind which the medical items to be audited are located. This is represented by logic step 1252. In exemplary embodiments, when a particular listing of items is subject to audit, the indicators associated with the particular buttons for the positions containing the supplies are also activated. This is represented in a logic step 1254. Further, in some exemplary embodiments other indicators such as, for example, the "Take" and "Return" indicators 950, 952 shown in FIG. 5 may be illuminated in a distinctive manner to indicate that the system is in audit mode. Of course these approaches are exemplary, and in other embodiments other approaches may be used.

In the exemplary logic flow, the display on each shelf is operative to output the expected quantity that should be located in the particular location that is subject to audit. Alternatively, if multiple items stored within the same storage shelf or module are on the audit list, the position indicators will be illuminated and the display will not provide an output until the particular push button corresponding to a storage position is selected. As represented in a logic step 1256, in these circumstances the user selects a particular item by pressing the push button associated with the storage location. When this is done, the display on the shelf as well as at the display terminal outputs the indicated quantity for the particular position.

The user then counts the number of items in the position to determine if the count currently held in the system is accurate. If the count is accurate, the user can provide an accept input 1262 for the current count by touching the "Accept" button in the audit quantity screen 1250. This is represented by a logic step 1260. Alternatively, if the quantity currently stored in the system is not correct, the user is enabled to modify the count of the items by inputting a different quantity. This may be done as indicated in a logic step 1258 by using the shelf keypad to input a different quantity and then providing an "Accept" input 1262. Alternatively, in the exemplary embodiment the user is enabled to provide the quantity input through the quantity buttons of the audit quantity screen 1250. In response to the user inputs, the one or more processors in operative connection with the display terminal are operative to update the information in one or more connected data stores. In situations where discrepancies were previously noted or where the audit uncovers a discrepancy, data related to the circumstances may be stored and processed so as to be subject to additional analysis if appropriate, through operation of the processors connected to the display terminal or through other computers connected in the system.

After the particular quantity of medical items in a particular position is audited the system may thereafter either responsive to user inputs or the operation of the iterative selection by the connected computers, to move to another supply position. The process then repeats until completed. It should be understood, however, that although in the exemplary embodiment the user indicates a particular quantity by an input at the display terminal of the "Accept" button, in other embodiments other types of "Accept" inputs may be used. These may include, for example, providing such an input at the particular shelf or module. For example, in some embodiments the system may be structured to treat the actuation of a keypad button on a shelf dedicated for the purpose or pressing of two other keypad buttons on a shelf simultaneously as a "Accept" input. Of course this approach is exemplary, and in other embodiments other approaches may be used.

Figure 38:
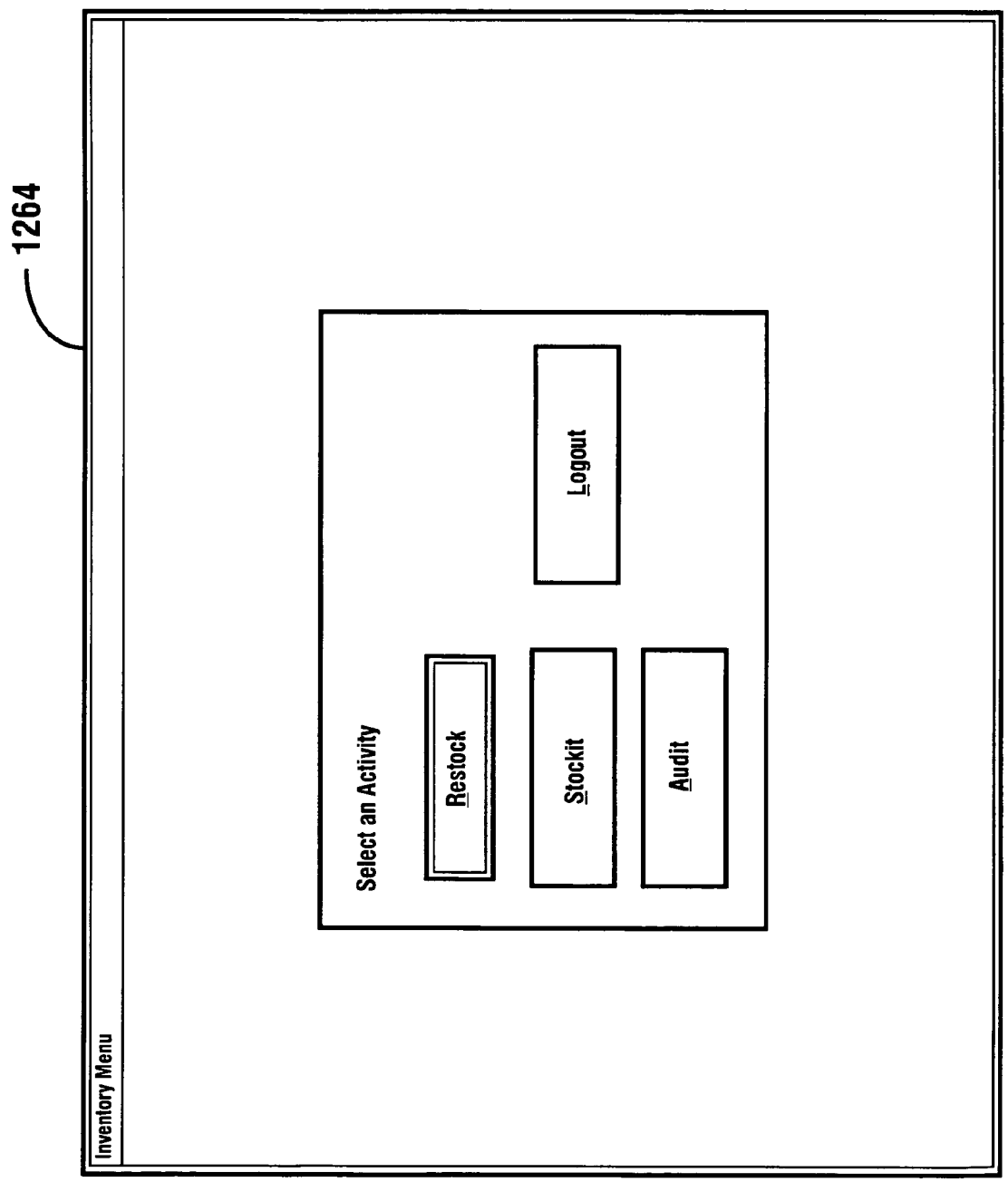

As previously discussed, the exemplary embodiment of the system enables users who are not authorized to have access to patient data to perform the audit function. Similarly, users not authorized to have access to patient data may further perform other functions such as functions associated with stocking medical items in the storage locations. In the logic associated with the alternative embodiment represented in FIG. 35, a user that does not have authorization to access patient information is presented with the inventory menu screen 1264 shown in FIG. 38 when the user logs onto the system, rather than the patient browser screen. The inventory menu screen 1264 provides selections for such a user. In the exemplary embodiment these functions include the audit function as well as the "Stock It" and restock functions. Of course in other embodiments other or different options may be provided.

In the exemplary embodiment the user selecting the audit function from the inventory menu screen 1264 may be presented with a witness log-in screen, as previously discussed, in accordance with the system programming. Further, such a user will be presented with a cabinet browser screen and audit browser screen in the manner previously discussed so as to enable the user to perform the audit function. Likewise, if the user selects one of the other stocking functions, the logic flow is generally similar to that previously described, except that the system is programmed to prevent the user from having access to particular patient information of the type that is enabled to be accessed through selections input through the patient browser screen.

The further aspect of the exemplary embodiment is that a plurality of push buttons on a particular shelf or support module are available, but only those that an operator wishes to have associated with a particular supply are required to be active within the system. It is desirable that push buttons not associated with a particular supply not be active for purposes of carrying out particular transactions. This is accomplished in an exemplary embodiment through the logic flow schematically represented in FIG. 42.

In this exemplary embodiment the logic flow for the display terminal associated with the particular supply cabinet is set to a "Configure-It" mode, as represented schematically in logic step 1266. When the system is in the "Configure-It" mode, the cabinet doors are unlocked, and the "Take" and "Return" LEDs are not operative, as indicated in logic steps 1268 and 1270.

For purposes of selecting certain buttons on a shelf or module interface to be operative, the user selects a particular shelf push button by pressing it, as represented in a logic step 1272. The user then provides a numerical input as represented in a logic step 1274 to indicate the storage location designated relative to the shelf to which the particular button corresponds. As can be appreciated, in the exemplary embodiment these particular locations are labeled with identifiers such as labels having the same color scheme or other indicia so as to indicate that they correspond.

Figure 42:
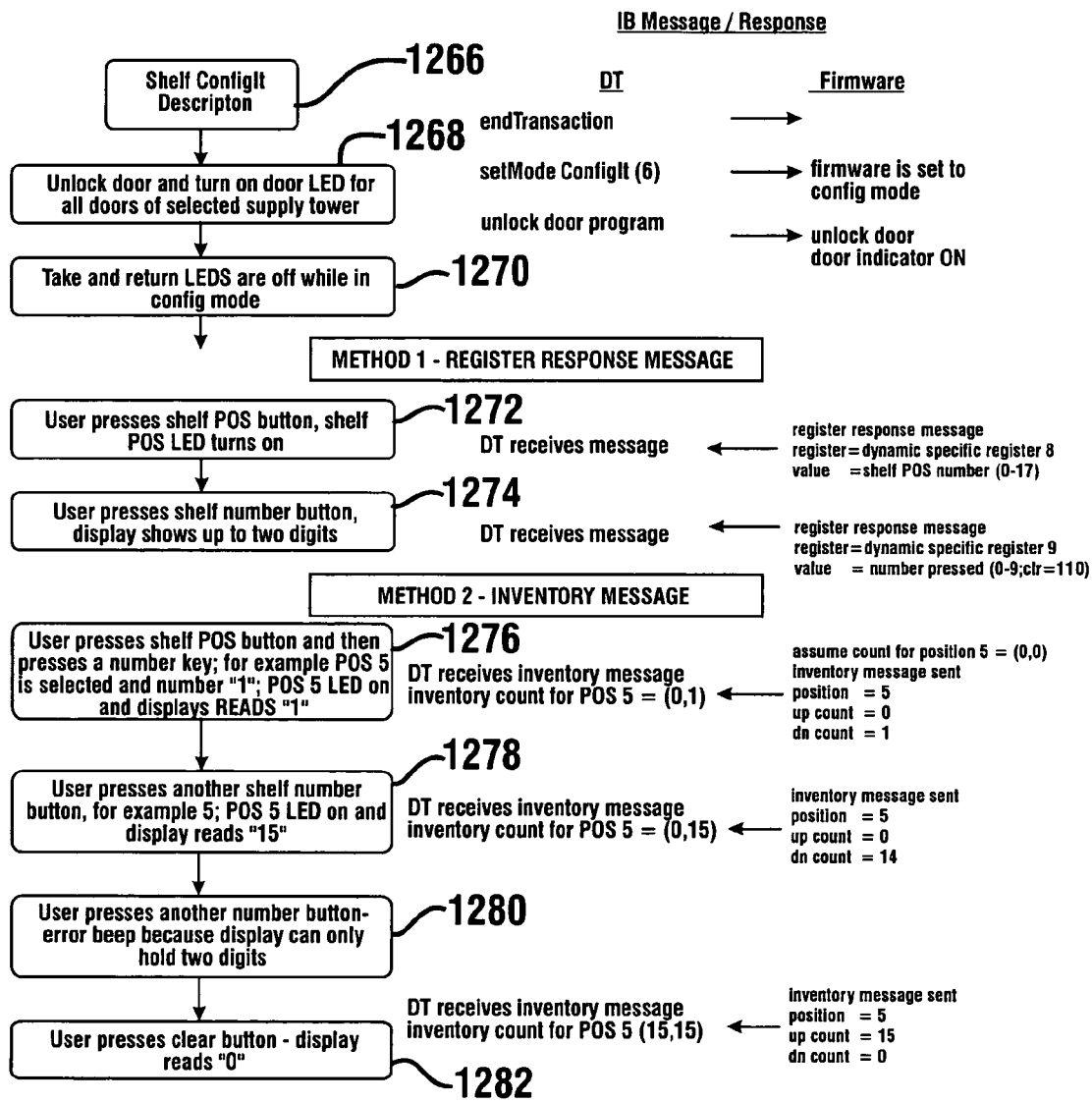
FIG. 42 is an exemplary flow chart associated with configuring an exemplary system with supply information.

Alternatively, locations can be designated by providing particular position inputs as well as numerical inputs to the shelf interface to indicate that the particular location is active. This approach is represented by the logic steps 1276, 1278, 1280, and 1282 in FIG. 42. Again, responsive to registering the particular position and corresponding input button as active in the system, the system can thereafter be programmed to indicate a particular type of medical item associated with the particular position. This can be done, for example, through inputs through a display terminal, at an administrator work station, through scanning indicia with a reading device such as bar code from a report, list or a supply itself, reading an RFID tag with an RFID reader, or other suitable programming methods. Such inputs can be provided by input devices connected to the display terminal. Alternatively, inputs corresponding to medical items can be input through input devices associated with an administrator work station or other computer connected in the system. As indicated in FIG. 42, the quantity of the particular medical item to be stored in a given storage location can be input through the shelf interface. This can be done by actuating a button corresponding to the storage location and providing numerical inputs through the shelf keypad. Alternatively in some embodiments medical item identifying data and/or quantity data may be input through the display terminal. This may be done by highlighting an item on a list to indicate the item is to be stored in a given location. Quantity data can be input through input devices such as the touch screen. One or more processors are operative to cause the data associating data corresponding to the types of medical items, storage locations, shelf buttons and medical item quantities in at least one data store. Of course, it should be understood that these approaches are exemplary, and in other embodiments other approaches may be used.

It should be understood that the transactions mentioned in connection with the supply cabinets and system are exemplary. As can be appreciated from the foregoing discussion, numerous alternatives are available based on the teachings of the present invention that provide advantages in the controlling and tracking of medical items.

Thus the exemplary system and method for controlling and tracking medical items of the exemplary form of the present invention, achieves at least one of the above stated objectives, eliminates difficulties encountered in the use of prior systems and methods, solves problems and attains the desirable results described herein.

In the foregoing description certain terms have been used for brevity, clarity and understanding, however no unnecessary limitations are to be implied therefrom because such terms are used for descriptive purposes and are intended to be broadly construed. Moreover, the descriptions and illustrations given herein are by way of examples and the invention is not limited to the exact details shown and described.

In addition, any feature described in the following claims as a means for performing a function shall be construed as encompassing any means known to those persons having skill in the art as being capable of performing the recited function, and shall not be deemed limited to the particular means disclosed in the foregoing description, or a mere equivalent thereof.

Having described the features, discoveries and principles of the invention, the manner in which it is constructed, operated and utilized, and the advantages and useful results attained; the new and useful structures, devices, elements, arrangements, parts, combinations, systems, equipment, operations, methods and relationships are set forth in the appended claims.

We claim:

1. Apparatus comprising:
    a medical item holding cabinet including at least one electrically controlled lock adapted to control access to an interior area of the cabinet;
    a terminal in operative connection with the at least one lock, wherein the terminal includes a user interface accessible from outside the cabinet, wherein the user interface includes at least one input device operative to receive user-identifying inputs and patient-identifying inputs from users, and wherein the terminal is operative responsive to input data corresponding to an authorized user, to cause a first lock to change from a locked to an unlocked condition, wherein in the unlocked condition a first door is enabled to be opened, wherein the first door controls access to a first area within the interior of the cabinet;
    a movably mounted module,
    wherein the module is removably mounted relative to and supported by a slide mount positioned in the first area, wherein the slide mount includes a longitudinal axis extending in an axial direction,
        wherein when the first door is opened, the module is movable in the axial direction away from the first area to extend outward from the first area, wherein the module is movable from being extended outward to being returned to the first area, enabling the first door to be closed, wherein the module includes a first end and a second end, wherein the module includes a first side and a second side, wherein both the first side and the second side extend in the axial direction, wherein the second side faces opposite the first side, wherein the module comprises a plurality of supports extending therefrom, wherein each support is adapted to support a medical item by engaging a medical item in hanging supported relation, wherein the module includes a module interface extending on the first side of the module, wherein the module interface includes a plurality of finger actuatable buttons corresponding to locations in which medical items may be stored, wherein the buttons are selectively actuatable to indicate the taking of a medical item from a particular support for use in treating a patient identified through at least one input to the terminal, and wherein the terminal is operative responsive to button actuation to cause data to be stored in at least one data store, corresponding to the taking of the medical item for treatment of the patient, wherein the module is selectively reversibly positionable relative to the slide mount, enabling the module interface to be selectively positioned on either a left or a right hand side of the module relative to the cabinet, wherein the module is positionable in a first mounted position relative to the slide mount, wherein in the first mounted position the module interface is positioned on a right hand side of the module relative to the cabinet, wherein in the first mounted position the first end extends further outward than the second end when the module is extended outward from the first area, wherein in the first mounted position the module extends in the axial direction, wherein the module is positionable in a second mounted position relative to the slide mount, wherein in the second mounted position the module interface is positioned on a left hand side of the module relative to the cabinet, wherein in the second mounted position the second end extends further outward than the first end when the module is extended outward from the first area, wherein in the second mounted position the module extends in the axial direction.

2. The apparatus according to claim 1 and further comprising a plurality of self-adhesive labels in overlying relation of at least some but not all of the plurality of buttons on the module, and wherein data is caused to be stored in the at least one data store representative of taking of a medical item, responsive to actuation of at least one button including a label.

3. The apparatus according to claim 2 wherein each of the plurality of medical item supports comprises a hook adapted to engage an aperture in a medical item.

4. The apparatus according to claim 3 and further comprising at least one hinge mounting the door in movable supporting connection with the cabinet, and wherein the hinge is changeable to enable mounting the door to be left or right hand opening relative to the first area, and wherein the module interface is enabled to be positioned on the left hand side of the module when the at least one hinge is positioned on the right hand side of the door, and vice versa.

5. The apparatus according to claim 1 wherein the plurality of supports comprise a plurality of hooks each adapted to engage an aperture of a medical item.

6. The apparatus according to claim 1 and further comprising at least one hinge mounting the door in movable supporting connection with the cabinet, and wherein the at least one hinge is changeable to enable mounting the door in left or right hand opening relation with regard to the first area, and wherein when the module interface is positioned on the left hand side of the module, the hinge is positionable on the right hand side relative to the opening of the door, and vice versa.

7. The apparatus according to claim 1 and further comprising a plurality of label members, wherein each label member is associated with a respective medical item support.

8. The apparatus according to claim 1 and further comprising a plurality of label members, wherein each label member is in supporting connection with a respective medical item support and includes indicia identifying a medical item enabled to be supported on the respective support.

9. The apparatus according to claim 1 wherein each of the plurality of medical item supports includes a hook, and further comprising a plurality of label members, wherein each of the label members includes indicia identifying a medical item, and wherein each label member is releasably movably engaged with a respective hook.

10. The apparatus according to claim 1 and farther comprising a plurality of label members, wherein each label member is in supporting connection with a respective medical item support, and wherein each label member includes machine-readable indicia corresponding to a medical item adapted to be positioned in engagement with a respective medical item support, and further comprising a reading device adapted to read machine-readable indicia, wherein the reading device is in operative connection with the terminal, and wherein reading the indicia with the reading device is operative to cause to be stored in the at least one data store, at least one of data associating a medical item with a respective medical item support, data indicating the taking of a medical item associated with the medical item support, and data associated with positioning a medical item on a medical item support.

11. Apparatus comprising:
a medical item holding cabinet including at least one electrically controlled lock adapted to control access to an interior area of the cabinet;
a terminal in operative connection with the at least one electrically controlled lock, wherein the terminal includes a user interface accessible from outside the cabinet, wherein the user interface includes at least one input device operative to receive user-identifying inputs and patient-identifying inputs from users, and wherein the terminal is operative responsive to input data corresponding to an authorized user, to cause at least one electrically controlled lock to change from a locked to an unlocked condition, wherein in the unlocked condition at least one door including at least one access door is enabled to be opened, wherein the at least one access door controls access to the interior area;
at least one module, wherein each module is movably mounted in supporting connection with a respective slide mount and is enabled to be moved to extend in an outward direction from the interior area when the at least one access door is opened, wherein each module comprises a plurality of supports extending therefrom, wherein each support is adapted to hangingly support a medical item, wherein each support is selectively rotationally positionable relative to the outward direction;

at least one module interface, wherein each module interface is supported by a respective module, wherein each module interface includes a plurality of selectively actuatable buttons corresponding to locations in which medical items may be stored, and wherein the terminal is operative responsive to button actuation to cause data to be stored in at least one data store, corresponding to the taking of a medical item from a particular support;

and wherein each module interface is selectively positionable on either a first or second side of the respective module relative to the outward direction.

12. Apparatus comprising:
a medical item holding cabinet including at least one electrically controlled lock adapted to control access to an interior area of the cabinet;
a terminal in operative connection with the at least one electrically controlled lock, wherein the terminal includes a user interface accessible from outside the cabinet, wherein the user interface includes at least one input device operative to receive user-identifying inputs and patient-identifying inputs from users, and wherein the terminal is operative responsive to input data corresponding to an authorized user, to cause at least one electrically controlled lock to change from a locked to an unlocked condition, wherein in the unlocked condition at least one door including at least one access door is enabled to be opened, wherein the at least one access door controls access to the interior area;
at least one module, wherein each module is movably mounted in supporting connection with a respective slide mount and is enabled to be moved to extend in an outward direction from the interior area when the at least one access door is opened, wherein each module comprises a plurality of supports extending therefrom, wherein each support is adapted to hangingly support a medical item;
a plurality of label members, wherein each label member is in supporting connection with a respective medical item support, and wherein each respective label member is selectively angularly positionable in supporting connection with the medical item support to facilitate viewing from either the left front or the right front of the interior area;
at least one module interface, wherein each module interface is supported by a respective module, wherein each module interface includes a plurality of selectively actuatable buttons corresponding to locations in which medical items may be stored, and wherein the terminal is operative responsive to button actuation to cause data to be stored in at least one data store, corresponding to the taking of a medical item from a particular support;

and wherein each module interface is selectively positionable on either a first or second side of the respective module relative to the outward direction.

13. Apparatus comprising:
a medical item holding cabinet including at least one electrically controlled lock adapted to control access to an interior of the cabinet,
a terminal in operative connection with the at least one lock, wherein the terminal includes a user interface accessible from outside the cabinet, wherein the user interface includes at least one input device operative to receive user-identifying inputs and patient-identifying inputs from users, and wherein the terminal is operative responsive to input data corresponding to an authorized user, to cause a lock to change from a locked to an unlocked condition, wherein in the unlocked condition a door is enabled to be opened, wherein the door controls access to an area within the interior of the cabinet,
a movably mounted module, wherein the module is movably mounted in supporting connection with a slide mount positioned in the area wherein the module is enabled to be moved to extend in an outward direction from the area when the door is opened, and wherein the module comprises a plurality of supports extending therefrom, wherein each support is adapted to support a medical item by engaging a medical item in hanging supported relation,
a plurality of label members, wherein each label member includes indicia corresponding to a medical item, and wherein each label member is movably mounted in supporting connection with a respective medical item support, and wherein each label member and the module each respectively includes at least one of an interengaging projection and recess, and wherein each label member is releasably fixable in a left or right angled position by engagement of the at least one projection and recess,
wherein the module includes a module interface extending on a side of the module in the outward direction, and wherein the module interface includes a plurality of finger actuatable buttons corresponding to locations in which medical items may be stored, and wherein the buttons are selectively actuated to indicate the talking of a medical item from a particular support for use in treating a patient identified through at least one input to the terminal, and wherein the terminal is operative responsive to button actuation to cause data to be stored in at least one data store, corresponding to the taking of the medical item for treatment of the patient,
and wherein the module is selectively positionable relative to the cabinet such that the module interface may be selectively positioned on either a left or a right hand side of the module relative to the outward direction.

14. Apparatus comprising:
a medical item holding cabinet including at least one electrically controlled lock adapted to control access to an interior of the cabinet,
a terminal in operative connection with the at least one lock, wherein the terminal includes a user interface accessible from outside the cabinet, wherein the user interface includes at least one input device operative to receive user-identifying inputs and patient-identifying inputs from users, and wherein the terminal is operative responsive to input data corresponding to an authorized user, to cause a lock to change from a locked to an unlocked condition wherein in the unlocked condition a door is enabled to be opened, wherein the door controls access to an area within the interior of the cabinet,
a movably mounted module, wherein the module is movably mounted in supporting connection with a slide mount positioned in the areas wherein the module is enabled to be moved to extend in an outward direction from the area when the door is opened, and wherein the module comprises a plurality of supports extending therefrom, wherein each support comprises a hook adapted to support a medical item by engaging an aperture in a medical item in hanging supported relation, wherein each hook is selectively rotatably positionable relative to the module,
wherein the module includes a module interface extending on a side of the module in the outward direction, and wherein the module interface includes a plurality of finger actuatable buttons corresponding to locations in which medical items may be stored, and wherein the buttons are selectively actuated to indicate the taking of a medical item from a particular support for use in treating a patient identified through at least one input to the terminal, at least one hinge mounting the door in movable supporting connection with the cabinet, and wherein the hinge is changeable to enable mounting the door to be left or right hand opening relative to the area, and wherein the module interface is enabled to be positioned on the left hand side of the module when the at least one hinge is positioned on the right hand side of the door and vice versa, a plurality of sell-adhesive labels in overlying relation of at least some but not all of the plurality of buttons on the module and wherein the terminal is operative responsive to button actuation to cause data to be stored in at least one data store, representative of a taking of a medical item for treatment of a patient, responsive to actuation of at least one button including a label, and wherein the module interface is selectively positionable relative to the cabinet such that the module interface may be selectively positioned on either a left or a right hand side of the module relative to the outward direction.

15. The apparatus according to claim 14 and further comprising a plurality of label members, wherein each label member is in supporting connection with a respective hook, and wherein each label member includes indicia corresponding to a medical item adapted to be placed in supporting connection with the respective hook.

16. The apparatus according to claim 15 wherein each label member is rotationally movable in supporting connection with the respective hook, wherein each label is enabled to be moved between positions wherein the respective label member is readily viewable from a left front and a right front position relative to the first area.

17. The apparatus according to claim 16 wherein each label member includes a snap-in aperture, and wherein each hook comprises a vertically extending portion, and wherein the snap-in aperture engages a vertically extending portion of a respective hook.

18. The apparatus according to claim 17 and further comprising for each label member, at least one interengaging projection and recess, wherein the respective at least one of the projection and recess is associated with a respective label member and the other of the at least one projection and recess is associated with the module, and wherein engagement of the at least one respective projection and recess releasably holds a respective label member in an angular position relative to the module.

19. The apparatus according to claim 18 and further comprising a bar code reader in operative connection with the terminal, and wherein a plurality of label members each include at least one bar code corresponding to a medical item adapted to be positioned on a respective hook member, wherein the respective medical item corresponds to the bar code on the respective label member.

20. The apparatus according to claim 19 wherein scanning with the bar code reader a respective bar code on a label member on a hook, is operative to cause to be stored in the at least one data store, data corresponding to at least one of a medical item corresponding to the scanned bar code being taken from the respective hook and the medical item corresponding to the scanned bar code being stored on the respective hook.

* * * * *

UNITED STATES PATENT AND TRADEMARK OFFICE
CERTIFICATE OF CORRECTION

PATENT NO. : 7,596,427 B1
APPLICATION NO. : 11/031351
DATED : September 29, 2009
INVENTOR(S) : Frederick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this

Twenty-eighth Day of September, 2010

David J. Kappos
*Director of the United States Patent and Trademark Office*